US008841306B2

(12) United States Patent  (10) Patent No.: US 8,841,306 B2
Jain et al.  (45) Date of Patent: Sep. 23, 2014

(54) ANTIMICROBIALS

(75) Inventors: Rajesh Jain, New Delhi (IN); Sanjay Trehan, New Delhi (IN); Jagattaran Das, New Delhi (IN); Sandeep Kanwar, New Delhi (IN); Sitaram Kumar Magadi, New Delhi (IN); Sudhir Kumar Sharma, New Delhi (IN)

(73) Assignee: Panacea Biotec Ltd., New Delhi (IN)

( * ) Notice: Subject to any disclaimer, the term of this patent is extended or adjusted under 35 U.S.C. 154(b) by 393 days.

(21) Appl. No.: 13/130,440
(22) PCT Filed: Nov. 18, 2009
(86) PCT No.: PCT/IN2009/000658
§ 371 (c)(1), (2), (4) Date: May 20, 2011
(87) PCT Pub. No.: WO2010/058423
PCT Pub. Date: May 27, 2010

(65) Prior Publication Data
US 2011/0245258 A1    Oct. 6, 2011

(30) Foreign Application Priority Data
Nov. 20, 2008 (IN) ............................ 2623/DEL/2008

(51) Int. Cl.
A61K 31/33 (2006.01)
C07D 413/14 (2006.01)
C07D 417/12 (2006.01)
C07D 487/04 (2006.01)
C07D 413/12 (2006.01)
C07D 263/20 (2006.01)

(52) U.S. Cl.
CPC ............ *C07D 487/04* (2013.01); *C07D 417/12* (2013.01); *C07D 413/14* (2013.01); *C07D 413/12* (2013.01); *C07D 263/20* (2013.01)
USPC ................................. 514/253.09; 544/364

(58) Field of Classification Search
None
See application file for complete search history.

(56) References Cited

U.S. PATENT DOCUMENTS

| 5,565,571 | A | 10/1996 | Barbachyn et al. |
| 5,654,428 | A | 8/1997 | Barbachyn et al. |
| 5,654,435 | A | 8/1997 | Barbachyn et al. |
| 5,756,732 | A | 5/1998 | Barbachyn et al. |
| 5,801,246 | A | 9/1998 | Barbachyn et al. |
| 6,051,716 | A | 4/2000 | Hutchinson et al. |
| 6,689,779 | B2 | 2/2004 | Lee et al. |
| 2007/0155798 | A1 | 7/2007 | Rhee et al. |

FOREIGN PATENT DOCUMENTS

| CN | 1510032 | 7/2004 |
| CN | 101434584 | 5/2009 |
| EP | 1130016 | 9/2001 |
| WO | WO 93/09103 | 5/1993 |
| WO | WO 93/23384 | 11/1993 |
| WO | WO 95/07272 | 3/1995 |
| WO | WO 96/35691 | 11/1996 |
| WO | WO 97/30995 | 8/1997 |
| WO | WO 99/64417 | 12/1999 |
| WO | WO 00/29396 | 5/2000 |
| WO | WO 00/73301 | 12/2000 |
| WO | WO 01/94342 | 12/2001 |
| WO | WO 02/02095 | 1/2002 |
| WO | WO 02/064547 | 8/2002 |
| WO | WO 02/081469 | 10/2002 |
| WO | WO 02/081470 | 10/2002 |
| WO | WO 03/006447 | 1/2003 |
| WO | WO 03/007870 | 1/2003 |
| WO | WO 03/008389 | 1/2003 |
| WO | WO 03/064415 | 8/2003 |
| WO | WO 03/072553 | 9/2003 |
| WO | WO 03/097059 | 11/2003 |

(Continued)

OTHER PUBLICATIONS

"Metabolite", http://www.encyclopedia.com/doc/1E1-metabolit.html, accessed Jan. 25, 2008.*
"Treatment", http://medical-dictionary.thefreedictionary.com/treatment, accessed Aug. 28, 2013.*
Jantzen and Robinson (Modern Pharmaceutics, 1996, p. 596.*
"Hand Washing", http://www.mayoclinic.com/print/hand-washing/HQ00407/METHOD=print, accessed Jun. 1, 2009.*

(Continued)

*Primary Examiner* — Noble Jarrell
(74) *Attorney, Agent, or Firm* — Lowe Hauptman & Ham, LLP

(57) ABSTRACT

The present invention relates to novel phenyl oxazolidinone compounds of formula I, their pharmaceutically acceptable analogs, tautomeric forms, stereoisomers, polymorphs, prodrugs, metabolites, salts or solvates thereof. The invention also relates to the processes for the synthesis of novel compounds of formula I or their pharmaceutically acceptable analogs, tautomeric forms, stereoisomers, polymorphs, prodrugs, metabolites, salts or solvates thereof. The present invention also provides pharmaceutical compositions comprising novel compounds of formula I and methods of using them. The compounds of the present invention are useful as antimicrobial agents, effective against a number of aerobic and/or anaerobic Gram positive and/or Gram negative pathogens such as multi drug resistant species of *Staphylococcus, Streptococcus, Enterococcus, Bacterioides, Clostridia, H. influenza, Moraxella*, acid-fast organisms such as *Mycobacterium tuberculosis* as well as Linezolid resistant species of *Staphylococcus* and *Enterococcus*.

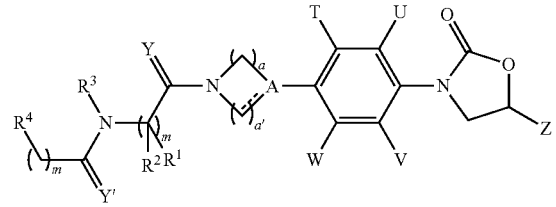

Formula I

14 Claims, No Drawings

(56) References Cited

FOREIGN PATENT DOCUMENTS

| | | | | |
|---|---|---|---|---|
| WO | WO 03/097640 | 11/2003 | | |
| WO | WO 2004/009587 | 1/2004 | | |
| WO | WO 2004/014392 | 2/2004 | | |
| WO | WO 2004/018439 | 3/2004 | | |
| WO | WO 2004/033451 | 4/2004 | | |
| WO | WO 2004/045616 | 6/2004 | | |
| WO | WO 2004/056817 | 7/2004 | | |
| WO | WO 2004/056818 | 7/2004 | | |
| WO | WO 2004/089943 | 10/2004 | | |
| WO | WO 2004/113329 | 12/2004 | | |
| WO | WO 2005/003087 | 1/2005 | | |
| WO | WO 2005/005399 | 1/2005 | | |
| WO | WO 2005/005422 | 1/2005 | | |
| WO | 2005036169 | * | 4/2005 | ............. G01N 33/53 |
| WO | WO 2005/058886 | 6/2005 | | |
| WO | WO 2005/082897 | 9/2005 | | |
| WO | WO 2005/082900 | 9/2005 | | |
| WO | WO 2005/116021 | 12/2005 | | |
| WO | WO 2005/116024 | 12/2005 | | |
| WO | WO 2006/035283 | 4/2006 | | |
| WO | WO 2006/043121 | 4/2006 | | |
| WO | WO 2006/109056 | 10/2006 | | |
| WO | WO 2007/000432 | 1/2007 | | |
| WO | WO 2007/004037 | 1/2007 | | |
| WO | WO 2007/040326 | 4/2007 | | |
| WO | WO 2007/082910 | 7/2007 | | |
| WO | WO 2007/093904 | 8/2007 | | |
| WO | WO 2007/095784 | 8/2007 | | |
| WO | WO 2007/114326 | 10/2007 | | |
| WO | WO 2009/001192 | 12/2008 | | |

OTHER PUBLICATIONS

Hutchinson, Douglas, "Recent Advances in Oxazolidinone Antibacterial Agent Research", Expert. Opin. Ther. Patents (2004) 14(9):1309-1328.

Armarego, W.L.F., et al., "Purification of Laboratory Chemicals", Fourth Edition, 1996.

Wang, Xiao-Jun et al., "Synthesis and Antibacterial Activities of Eperezolid Analogs with Glycinyl Substitutions", Arch. Pharm. Chem. Life Sci. 2009, 342, 377-385.

Han, Hyo-Kyung, et al., "Targeted Prodrug Design to Optimize Drug Delivery", AAPS Pharmsci 2000; 2 (1) article 6 (http://www.pharmsci.org/).

Miller, Keith et al., "Delayed Development of Linezolid Resistance in *Staphylococcus aureus* following Exposure to Low Levels of Antimicrobial Agents", Antimicrobial Agents and Chemotherapy, Jun. 2008, vol. 52, No. 6, pp. 1940-1944.

Walsh, Christopher T., et al., "Chemical Reviews Introduction: Antibiotic Resistance", vol. 105, No. 2, 2005 American Chemical Society.

Wilker, Matthew D., "Methods for Dilution Antimicrobial Susceptibility Tests for Bacteria That Grow Aerobically; Approved Standard—Eighth Edition", vol. 29, No. 2, Clinical and Laboratory Standards Institute, Jan. 2009.

Mutnick, Alan H., et al., "Linezolid Resistance Since 2001: SENTRY Antimicrobial Surveillance Program", The Annals of Pharmacotherapy, Jun. 2002, vol. 37, pp. 769-774.

Greene, Theodora W., et al., Protective Groups in Organic Synthesis, Third Edition, 2002.

International Search Report from corresponding application No. PCT/IN2009/000658.

\* cited by examiner

ANTIMICROBIALS

CROSS-REFERENCE TO RELATED APPLICATIONS

The present Application is the U.S. National Stage of International Application No. PCT/IN2009/000658, filed on Nov. 18, 2009, published in English; which Application claims priority benefit of Indian Application No. 2623/DEL/2008, filed on Nov. 20, 2008.

FIELD OF THE INVENTION

The present invention relates to novel phenyl oxazolidinone compounds of formula I, their pharmaceutically acceptable derivatives, tautomeric forms, stereoisomers including R and S isomers, polymorphs, prodrugs, metabolites, salts or solvates thereof. The invention also relates to the processes for the synthesis of novel compounds of formula I or their pharmaceutically acceptable derivatives, tautomeric forms, stereoisomers including R and S isomers, polymorphs, prodrugs, metabolites, salts or solvates thereof. The present invention also provides pharmaceutical compositions comprising novel compounds of formula I and methods of using them. The compounds of the present invention are useful as antimicrobial agents, effective against a number of aerobic and/or anaerobic Gram positive and/or Gram negative pathogens such as multi drug resistant species of *Staphylococcus, Streptococcus, Enterococcus, Bacterioides, Clostridia, H. influenza, Moraxella*, acid-fast organisms such as *Mycobacterium tuberculosis* as well as Linezolid resistant species of *Staphylococcus* and *Enterococcus*.

BACKGROUND OF THE INVENTION

Antibacterial resistance has increased alarmingly in the recent years resulting in bacterial strains against which currently available antimicrobial agents are ineffective. In particular, Gram positive bacteria are presenting a formidable treatment problem. Methicillin Resistant *Staphylococcus aureus* (MRSA), Vancomycin Resistant *Enterococci* (VRE) and Glycopeptide Resistant *Staphylococcus aureus* (GRSA) are no longer objects of scientific curiosity but a life threatening proposition that is confronting physicians all over the world. The 'super-bugs' are here to stay and in addition to the several measures to control the spread of drug resistance, a concerted effort is still needed to develop new antibiotics to control life threatening bacterial infections. This growing multidrug resistance has recently rekindled interest in the search for new structural class of antibiotics that kill or inhibit the growth of these bacteria. See, *Chemical Reviews*, "Antibiotic Resistance", 105 (2), February 2005.

Oxazolidinones are a class of antibacterial agents with a unique mechanism of inhibiting bacterial protein synthesis. They inhibit the formation of ribosomal initiation complex involving 30S and 50S ribosomes leading to prevention of initiation complex formation at the stage of protein synthesis. Due to their unique mechanism of action, these compounds are active against pathogens resistant to other clinically useful antibiotics.

Several patent publications disclose oxazolidinones as antimicrobial agents. For example, PCT publications bearing numbers WO 93/09103, WO 00/29396, WO 01/94342, WO 02/81469, WO 02/81470, WO 02/02095W0 03/072553, WO 03/006447, WO 03/07870, WO 03/08389, WO 03/97059, WO 04/056817, WO 04/056818, WO 04/14392, WO 04/009587, WO 04/018439A1, WO 05/058886, WO 05/082897, WO 05/116024, WO 05/116021, WO 05/082900, WO 05/003087, WO 06/043121 and US patents having numbers U.S. Pat. Nos. 6,689,779, 5,565,571, 5,801,246, 5,756,732, 5,654,435 and 5,654,428 disclose oxazolidinone compounds having antibacterial activity and useful as antimicrobial agents.

Some recent publications such as WO 07/114326, US 07/0155798, WO 07/040326, WO 07/095784, WO 07/000432, WO 07/004037 and WO 07/093904 disclose phenyl oxazolidinone derivatives as antibacterial agents. WO 06/109056, WO 06/035283, WO 03/072553, WO 03/064415 disclose heterobicyclic substituted phenyl oxazolidinones as antibacterial agents. WO 96/35691 and WO 00/073301 disclose bicyclic oxazolidinones as antibacterial agents. WO 02/064547 discloses pyridoarylphenyl oxazolidinones as antibacterial agents. WO 04/033451, WO 04/089943, WO 05/005422 and WO 05/005399 disclose bicyclo[3.1.0]hexyl-phenyl-oxazolidinone derivatives useful for treating bacterial infections. PCT publication WO 07/082910 discloses dicarbonyl compounds having antibacterial activity. A recent Chinese patent application CN 101434584 discloses phenyl oxazolidinones with glycinyl substitutions having antibacterial activity.

Linezolid (sold under the trade name Zyvox®), the first oxazolidinone to receive regulatory approval, has become an important clinical option in the treatment of serious Gram-positive bacterial infections, including those caused by multidrug resistant pathogens such as MRSA and VRE (see WO 95/07272). Inspite of its high potential as an antibiotic and its unique mode of action, no other molecule from oxazolidinone class, except for linezolid, could make it to the clinic. Moreover, development of resistance to an antibiotic is inevitable, and linezolid has been no exception. (See, Mutnick, A. H.; Enne, V.; Jones, R. N. *Ann. Pharmacother.*, 2003, 37, 769-774). Further, due to myelosuppression, linezolid is not suitable for long duration therapy, although there are cases where patients receiving linezolid for more than two years are without serious side effects. (See, Hutchinson, D. K. *Expert Opin. Ther. Patents* 2004, 14, 1309-1328). Linezolid and its analogs (first generation oxazolidinones) are generally limited in their antimicrobial spectrum to Gram-positive pathogens only. An expanded spectrum and enhanced potency of newer second generation oxazolidinones with activity against Gram-negative pathogens could expand the utility of this class beyond the hospital setting into the treatment of community acquired infections. Thus, there is an ongoing need to develop more effective and safe compounds. The compounds of the present invention are novel, none of them having been previously reported in the prior art. The novel compounds of formula I according to the present invention possess improved efficacy, particularly enhanced activity against bacterial infections, appreciable bioavailability, reduced associated side effects, good solubility and can be made into formulations with ease.

SUMMARY OF THE INVENTION

The present invention relates to novel phenyl oxazolidinones of formula I,

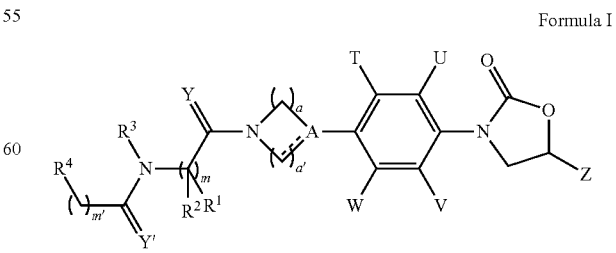

Formula I their pharmaceutically acceptable derivatives, tautomeric forms, stereoisomers including R and S isomers, polymorphs, prodrugs, metabolites, salts or solvates thereof, wherein: '___' is independently a single bond or absent;

when '___' is a single bond, 'A' represents carbon atom and when '___' is absent, 'A' is CH or N;

Y and Y' are same or different and independently represent O or S;

$R^1$ and $R^2$ are same or different and independently represent hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{1-12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-20}$cycloalkyl, heterocyclyl, aryl, heteroaryl, $-(CH_2)_n$-cycloalkyl, $-(CH_2)_n$-heterocyclyl, $-(CH_2)_n$-aryl, $-(CH_2)_n$-heteroaryl, $-(CH_2)_nC(=Y)NR^5R^6$, $-(CH_2)_nC(=Y)OR^5$, $-(CH_2)_nNR^5R^6$, $-(CH_2)_nOC(=Y)R^5$, $-(CH_2)_nOC(=Y)OR^5$, $-(CH_2)_nOC(=Y)NR^5R^6$, $-(CH_2)_nN(R^5)C(=Y)OR^6$, $-(CH_2)_nN(R^5)C(=Y)NR^5R^6$, $-(CH_2)_nNR^5C(=Y)R^6$, $-(CH_2)_nC(=Y)R^5$, $-(CH_2)_nYR^5$ (wherein each methylene group may be substituted by one or more halogen atoms), $-C(=Y)NR^5R^6$, $-OC(=Y)R^5$, $-OC(=Y)NR^5R^6$, $-C(=Y)OR^5$, $-OR^5$, $-OC(=Y)OR^5$, $-SR^5$, $-NO_2$, $-NR^5R^6$, $-N(R^5)C(=Y)R^6$, $-N(R^5)-C(=Y)OR^6$, or $-N(R^5)C(=Y)NR^5R^6$, each of which may be optionally substituted at any available position by one or more substituents $R^a$; or $R^1$ and $R^2$ can together with the carbon atom to which they are attached form a 3 to 10 membered monocyclic ring, partially unsaturated or saturated, which may contain from one to three heteroatoms independently selected from O, S or N; the ring thus formed may be fused with one or two rings independently selected from the group comprising an aryl ring, a cycloalkyl ring, a heterocyclyl ring or monocyclic heteroaryl ring; the ring thus formed can be optionally substituted at any available position by one or more substituents $R^a$;

$R^3$ represents hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_6$alkoxy$C_1$-$C_6$alkyl, $C_1$-$C_6$alkoxy$C_1$-$C_6$alkoxy$C_1$-$C_3$alkyl, $C_{3-20}$cycloalkyl, heterocyclyl, aryl, heteroaryl, $-(CH_2)_n$-cycloalkyl, $-(CH_2)_n$-heterocyclyl, $-(CH_2)_n$-aryl, $-(CH_2)_n$-heteroaryl, $-(CH_2)_nYR^5$, $-(CH_2)_nC(=Y)R^5$, $-(CH_2)_nNR^5R^6$, $-(CH_2)_nC(=Y)NR^5R^6$, $-(CH_2)_nC(=Y)OR^5$, $-(CH_2)_nOC(=Y)R^5$, $-(CH_2)_nOC(=Y)OR^5$, $-(CH_2)_nNR^5C(=Y)R^6$, $-(CH_2)_nN(R^5)C(=Y)OR^6$, $-(CH_2)_nN(R^5)C(=Y)NR^5R^6$, $-(CH_2)_nOC(=Y)NR^5R^6$, or $-(Ch_2)_nN(R^5)C(=Y)NR^5R^6$, (wherein each methylene group may be substituted by one or more halogen atoms), each of which may be optionally substituted at any available position by one or more substituents $R^a$;

$R^4$ represents hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-20}$cycloalkyl, heterocyclyl, aryl, heteroaryl, $-C(=Y)NR^5R^6$, $-C(=Y)OR^5$, $-NR^5R^6$, $-NR^5C(=Y)R^6$, $-C(=Y)R^5$, $-OC(=Y)R^5$, $-OC(=Y)OR^5$, $-OC(=Y)NR^5R^6$, $-OR^5$, $-(CH_2)_nOR^5$, $-SR^5$, $-NO_2$, $-N(R^5)C(=Y)OR^6$, or $-N(R^5)C(=Y)NR^5R^6$, each of which may be optionally substituted at any available position by one or more substituents $R^a$;

Z represents $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-20}$cycloalkyl, heterocyclyl, aryl, heteroaryl, $-(CH_2)_n$-cycloalkyl, $-(CH_2)_n$-heterocyclyl, $-(CH_2)_n$-aryl, $-(CH_2)_n$-heteroaryl, $-(CH_2)_n-N_3$, $-(CH_2)_n-NCS$, $-C(=Y)R^5$, $-C(=Y)OR^6$, $-C(=Y)NR^5R^6$, $-OC(=Y)OR^5$, $-(CH_2)_nYR^5$, $-(CH_2)_nOP(=O)R^5R^6$, $-(CH_2)_nNHP(=O)R^5R^6$, $-(CH_2)_nOC(=Y)R^5$, $-(CH_2)_nOC(=Y)OR^5$, $-(CH_2)_nC(=Y)R^5$, $-(CH_2)_nC(=Y)NR^5R^6$, $-(CH_2)_nOC(=Y)NR^5R^6$, $-(CH_2)_nC(=Y)OR^5$, $-(CH_2)_nNR^5R^6$, $-(CH_2)_nNR^5C(=Y)R^6$, $-(CH_2)_nNR^5C(=Y)OR^6$, $-(CH_2)_nNR^5C(=Y)NR^5R^6$, or $-(CH_2)_nNR^5S(O)_dR^6$ (wherein each methylene group may be substituted by one or more halogen atoms), each of which may be optionally substituted at any available position by one or more substituents $R^a$;

T, U, V and W are same or different and independently represent hydrogen or halogen;

$R^5$ and $R^6$ are same or different and are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-8}$ cycloalkyl, heterocyclyl, aryl, heteroaryl, aryloxy, $-(CH_2)_n$-cycloalkyl, $-(CH_2)_n$-heterocyclyl, $-(CH_2)_n$-aryl, $-(CH_2)_n$-heteroaryl, each of which may be optionally substituted at any available position with halogen, hydroxyl, $C_{1-12}$ alkyl, $C_{2-12}$ alkenyl, $C_{2-12}$ alkynyl, $C_{1-12}$ alkoxy, $C_{1-12}$ alkylcarbonyl, $C_{1-12}$ alkoxycarbonyl, $C_{3-8}$ cycloalkyl, $C_{1-12}$ haloalkyl, $C_{1-12}$ haloalkoxy, $C_{2-12}$ haloalkenyl, aryl, heterocyclyl, heteroaryl, $-(CH_2)_n$-aryl, $-(CH_2)_n$-heterocyclyl, $-(CH_2)_n$-heteroaryl, $-(CH_2)_n$-cycloalkyl, $-CN$, $-NO_2$, $-NR^7R^8$, $-N(R^7)C(=Y)R^8$, $-N(R^7)C(=Y)OR^8$, $-N(R^7)C(=Y)NR^7R^8$, $-C(=Y)R^7$, $-C(=Y)NR^7R^8$, $-OC(=Y)R^7$, $-OC(=Y)NR^7R^8$, $-C(=Y)OR^7$, $-OC(=Y)OR^7$, $-SR^7$, $-S(O)_dR^7$, $-SO_2NR^7R^8$, $-NR^7SO_2R^8$, $-OP(=O)R^7R^8$, $-NHP(=O)R^7R^8$, or $-P(=O)R^7R^8$; or $R^5$ and $R^6$ may be joined together along with the heteroatom to which they are joined to form a heterocyclic or heteroaryl ring which may additionally contain from one to three heteroatoms independently selected from O, S or N, the ring formed may optionally be substituted with one or more substituents selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-8}$ cycloalkyl, heterocyclyl, aryl, heteroaryl, $-(CH_2)_n$-cycloalkyl, $-(CH_2)_n$-heterocyclyl, $-(CH_2)_n$-aryl, $-(CH_2)_n$-heteroaryl, $-C_{1-12}$ alkylcarbonyl, $-C_{1-12}$ alkoxycarbonyl, $-CN$, $-OR^7$, $-CF_3$, $-OCF_2CH_2CF_3$, $-CF_2CF_3$, $-NO_2$, $-NR^7R^8$, $-N(R^7)C(=Y)R^8$, $-N(R^7)C(=Y)OR^8$, $-N(R^7)C(=Y)NR^7R^8$, $-C(=Y)R^7$, $-C(=Y)NR^7R^8$, $-OC(=Y)R^7$, $-OC(=Y)NR^7R^8$, $-OC(=Y)OR^7$, $-C(=Y)OR^7$, $-SR^7$, $-S(O)_dR^7$, $-SO_2NR^7R^8$; $-NR^7SO_2R^8$, $-OP(=O)R^7R^8$, $-NHP(=O)R^7R^8$, or $-P(O)R^7R^8$; the ring thus formed may further be fused with 3 to 7 membered unsaturated or saturated ring, which may contain from one to three heteroatoms independently selected from O, S or N, the fused ring may optionally be substituted at any available position by one or more substituents $R^a$;

$R^a$ is independently selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, oxo, $C_{1-12}$ alkoxy, $C_1$-$C_6$alkoxy$C_1$-$C_6$alkyl, $C_1$-$C_6$alkoxy$C_1$-$C_6$alkoxy$C_1$-$C_3$alkyl, $C_{1-12}$ haloalkoxy, $C_{3-8}$ cycloalkyl, heterocyclyl, aryl, heteroaryl, $-(CH_2)_n$-cycloalkyl, $-(CH_2)_n$-heterocyclyl, $-(CH_2)_n$-aryl, $-(CH_2)_n$-heteroaryl, $-C_{1-12}$ alkylcarbonyl, $-C_{1-12}$ alkoxycarbonyl, $-CN$, $-YR^7$, $-(CH_2)_nYR^7$, $-NO_2$, $=NOR^7$, $-NR^7R^8$, $-N(R^7)C(=Y)R^8$, $-N(R^7)C(=Y)OR^8$, $-N(R^7)C(=Y)NR^7R^8$, $-C(=Y)R^7$, $-C(=Y)NR^7R^8$, $-OC(=Y)R^7$, $-OC$ (=Y)NR⁷R⁸, —C(=Y)OR⁷, —OC(=Y)OR⁷, —SR⁷, —S(O)_dR⁷, —SO₂NR⁷R⁸, —OP(=O)R⁷R⁸, —NHP(=O)R⁷R⁸, —P(O)R⁷R⁸, —(CH₂)_nCN, —YR⁷, —(CH₂)_nYR⁷, —NO₂, =NOR⁷, —(CH₂)_nNR⁷R⁸, —(CH₂)_nN(R⁷)C(=Y)R⁸, —(CH₂)_nN(R⁷)C(=Y)OR⁸, —(CH₂)_nN(R⁷)C(=Y)NR⁷R⁸, —(CH₂)_nC(=Y)R⁷, —(CH₂)_nC(=Y)NR⁷R⁸, —(CH₂)_nOC(=Y)R⁷, -(CH₂)_nOC(=Y)NR⁷R⁸, —(CH₂)_nC(=Y)OR⁷, —(CH₂)_nOC(=Y)OR⁷, —(CH₂)_nSR⁷, —(CH₂)_nS(O)_dR⁷, —(CH₂)_nSO₂NR⁷R⁸, —(CH₂)_nOP(=O)R⁷R⁸, —(CH₂)_nNHP(=O)R⁷R⁸, or —(CH₂)_nP(O)R⁷R⁸; each of which may optionally be substituted at any available position by one or more substituents selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, oxo, $C_1-C_{12}$alkoxy, $C_{1-12}$ haloalkoxy, $C_1-C_6$alkoxyC₁-C₆alkyl, $C_1-C_6$alkoxyC₁-C₆alkoxyC₁-C₃alkyl, $C_{3-8}$ cycloalkyl, heterocyclyl, aryl, heteroaryl, —(CH₂)_n-cycloalkyl, —(CH₂)_n-heterocyclyl, —(CH₂)_n-aryl, —(CH₂)_n -heteroaryl, —$C_{1-12}$ alkylcarbonyl, —$C_{1-12}$ alkoxycarbonyl, —CN, —OR⁹, —(CH₂)_nOR⁹, —CF₃, —NO₂, —NR⁹R¹⁰, —N(R⁹)C(=Y)R¹⁰, —N(R⁹)C(=Y)OR¹⁰, —N(R⁹)C(=Y)NR⁹R¹⁰, —C(=Y)R⁹, —C(=Y)NR⁹R¹⁰, —OC(=Y)R⁹, —OC(=Y)NR⁹R¹⁰, —OC(=Y)OR⁹, —C(=Y)OR⁹, —SR⁹, —S(O)_dR⁹, —SO₂NR⁹R¹⁰; —NR⁹SO₂R¹⁰, —OP(=O)R⁹R¹⁰, —NHP(=O)R⁹R¹⁰, —P(O)R⁹R¹⁰, —(CH₂)_nCN, —OR⁹, —(CH₂)_nOR⁹, —CF₃, —NO₂, —(CH₂)_nNR⁹R¹⁰, —(CH₂)_nN(R⁹)C(=Y)R¹⁰, —(CH₂)_nN(R⁹)C(=Y)OR¹⁰, —(CH₂)_nN(R⁹)C(=Y)NR⁹R¹⁰, —(CH₂)_nC(=Y)R⁹, —(CH₂)_nC(=Y)NR⁹R¹⁰, —(CH₂)_nOC(=Y)R⁹, —(CH₂)_nOC(=Y)NR⁹R¹⁰, —(CH₂)_nOC(=Y)OR⁹, —(CH₂)_nC(=Y)OR⁹, —(CH₂)_nSR⁹, —(CH₂)_nS(O)_dR⁹, —(CH₂)_nSO₂NR⁹R¹⁰; —(CH₂)_nNR⁹SO₂R¹⁰, —(CH₂)_nOP(=O)R⁹R¹⁰, —(CH₂)_nNHP(=O)R⁹R¹⁰, or —(CH₂)_nP(O)R⁹R¹⁰;

$R^7$ and $R^8$ are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{3-8}$ cycloalkyl, heterocyclyl, aryl, heteroaryl, —(CH₂)_n-cycloalkyl, —(CH₂)_n-heterocyclyl, —(CH₂)_n-aryl, or —(CH₂)_n-heteroaryl, each of which may be optionally substituted with halogen, hydroxyl or $C_{1-6}$ alkoxy, or $R^7$ and $R^8$ may be joined together along with the heteroatom to which they are attached to form a heterocyclic or heteroaryl ring which may contain from one to three heteroatoms independently selected from O, S or N, each of which may be optionally substituted with halogen, hydroxyl, $C_{1-6}$ alkyl or $C_{1-6}$ alkoxy.

$R^9$ and $R^{10}$ are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{3-8}$ cycloalkyl, heterocyclyl, aryl, heteroaryl, —(CH₂)_n-cycloalkyl, —(CH₂)_n-heterocyclyl, —(CH₂)_n-aryl, or —(CH₂)_n-heteroaryl, each of which may be optionally substituted with halogen, hydroxyl or $C_{1-6}$ alkoxy, or $R^9$ and $R^{10}$ may be joined together along with the heteroatom to which they are attached to form a heterocyclic or heteroaryl ring which may contain from one to three heteroatoms independently selected from O, S or N, each of which may be optionally substituted with halogen, hydroxyl, $C_{1-6}$ alkyl or $C_{1-6}$ alkoxy.

a and a' are same or different and independently represent 1,2,3 or 4;
m is 1, 2, 3 or 4;
m' is 0, 1, 2, 3 or 4;
n is 1, 2, 3 or 4;
d is 1 or 2.
with the proviso that when both $R^1$ and $R^2$ are hydrogen, Y and Y' are oxygen, $R^3$ is hydrogen, A is nitrogen, '___' is absent, a and a' are both 2, T is fluorine, W, U and V are hydrogen, m is 1 and m' is 0, then Z does not represent

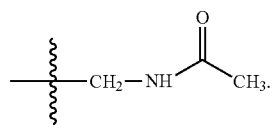

Another aspect of the invention provides the processes for the preparation of the novel compounds of formula I or their pharmaceutically acceptable derivatives, tautomeric forms, stereoisomers including R and S isomers, polymorphs, prodrugs, metabolites, salts or solvates thereof.

A further aspect of the present invention provides pharmaceutical compositions, containing compounds of formula I or their pharmaceutically acceptable derivatives, tautomeric forms, stereoisomers including R and S isomers, polymorphs, prodrugs, metabolites, salts or solvates thereof in combination with one or more pharmaceutically acceptable carrier(s).

Another aspect of the invention is to provide methods of using the compounds of formula I of the present invention or compositions comprising the compounds of formula I for the management such as prophylaxis, amelioration and/or treatment of disease(s)/disorder(s) especially caused by microbial infections which comprises administering to a subject in need thereof the compounds of formula I or compositions comprising a pharmaceutically effective amount of the compounds of formula I.

Yet another aspect of the invention is the use of the compounds of formula I as antimicrobial agents, effective against a number of aerobic and/or anaerobic Gram positive and/or Gram negative pathogens such as multi drug resistant species of *Staphylococcus, Streptococcus, Enterococcus, Bacterioides, Clostridia, H. influenza, Moraxella*, acid-fast organisms such as *Mycobacterium tuberculosis* as well as Linezolid resistant species of *Staphylococcus* and *Enterococcus*.

In another aspect, the present invention provides a method for treating Gram positive and/or Gram negative pathogens in a mammal by administering a therapeutically effective amount of a compound of formula I or a pharmaceutically acceptable salt.

The present invention also encompasses prodrugs and active metabolites of the compounds of the formula I.

Other aspects of the invention will be set forth in the description which follows, and in part will be apparent from the description, or may be learnt by the practice of the invention.

DETAILED DESCRIPTION OF THE INVENTION

The present invention relates to novel phenyl oxazolidinones of Formula I,

Formula I

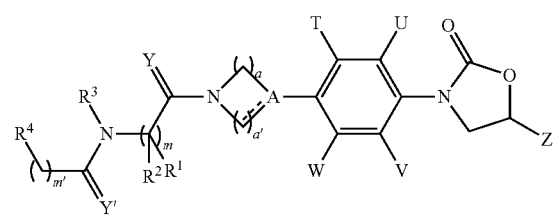

their pharmaceutically acceptable derivatives, tautomeric forms, stereoisomers including R and S isomers, polymorphs, prodrugs, metabolites, salts or solvates thereof, wherein:

'---' is independently a single bond or absent;

when '---' is a single bond, 'A' represents carbon atom and when '---' is absent, 'A' is CH or N;

Y and Y' are same or different and independently represent O or S;

$R^1$ and $R^2$ are same or different and independently represent hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-20}$cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, —$(CH_2)_nC(=Y)NR^5R^6$, —$(CH_2)_nC(=Y)OR^5$, —$(CH_2)_nNR^5R^6$, —$(CH_2)_n$—$C(=Y)R^5$, —$(CH_2)_nOC(=Y)OR^5$, —$(CH_2)_nOC(=Y)NR^5R^6$, —$(CH_2)_nN(R^5)C(=Y)OR^6$, —$(CH_2)_nN(R^5)C(=Y)NR^5R^6$, —$(CH_2)_nNR^5C(=Y)R^6$, —$(CH_2)_nC(=Y)R^5$, —$(CH_2)_nYR^5$ (wherein each methylene group may be substituted by one or more halogen atoms), —$C(=Y)NR^5R^6$, —$OC(=Y)R^5$, —$OC(=Y)NR^5R^6$, —$C(=Y)OR^5$, —$OR^5$, —$OC(=Y)OR^5$, —$SR^5$, —$NO_2$, —$NR^5R^6$, —$N(R^5)C(=Y)R^6$, —$N(R^5)$—$C(=Y)OR^6$, or —$N(R^5)C(=Y)NR^5R^6$, each of which may be optionally substituted at any available position by one or more substituents $R^a$; or $R^1$ and $R^2$ can together with the carbon atom to which they are attached form a 3 to 10 membered monocyclic ring, partially unsaturated or saturated, which may contain from one to three heteroatoms independently selected from O, S or N; the ring thus formed may be fused with one or two rings independently selected from the group comprising an aryl ring, a cycloalkyl ring, a heterocyclyl ring or monocyclic heteroaryl ring; the ring thus formed can be optionally substituted at any available position by one or more substituents $R^a$;

$R^3$ represents hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_6$alkoxy$C_1$-$C_6$alkyl, $C_1$-$C_6$alkoxy$C_1$-$C_6$alkoxy$C_1$-$C_3$alkyl, $C_{3-20}$cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, —$(CH_2)_nYR^5$, —$(CH_2)_nC(=Y)R^5$, —$(CH_2)_nNR^5R^6$, —$(CH_2)_nC(=Y)NR^5R^6$, —$(CH_2)_nC(=Y)OR^5$, —$(CH_2)_nOC(=Y)R^5$, —$(CH_2)_nOC(=Y)OR^5$, —$(CH_2)_nNR^5C(=Y)R^6$, —$(CH_2)_nN(R^5)C(=Y)OR^6$, —$(CH_2)_nN(R^5)C(=Y)NR^5R^6$, —$(CH_2)_nOC(=Y)NR^5R^6$, or —$(CH_2)_nN(R^5)C(=Y)NR^5R^6$, (wherein each methylene group may be substituted by one or more halogen atoms), each of which may be optionally substituted at any available position by one or more substituents $R^a$;

$R^4$ represents hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-20}$cycloalkyl, heterocyclyl, aryl, heteroaryl, —$C(=Y)NR^5R^6$, —$C(=Y)OR^5$, —$NR^5R^6$, —$NR^5C(=Y)R^6$, —$C(=Y)R^5$, —$OC(=Y)R^5$, —$OC(=Y)OR^5$, —$OC(=Y)NR^5R^6$, —$OR^5$, —$(CH_2)_nOR^5$, —$SR^5$, —$NO_2$, —$N(R^5)C(=Y)OR^6$, or —$N(R^5)C(=Y)NR^5R^6$, each of which may be optionally substituted at any available position by one or more substituents $R^a$;

Z represents $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, —$C_{3-20}$cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, —$(CH_2)_n$—$N_3$, —$(CH_2)_n$—NCS, —$C(=Y)R^5$, —$C(=Y)OR^6$, —$C(=Y)NR^5R^6$, —$OC(=Y)OR^5$, —$(CH_2)_nYR^5$, —$(CH_2)_nOP(=O)R^5R^6$, —$(CH_2)_nNHP(=O)R^5R^6$, —$(CH_2)_nOC(=Y)R^5$, —$(CH_2)_nOC(=Y)OR^5$, —$(CH_2)_nC(=Y)R^5$, —$(CH_2)_nC(=Y)NR^5R^6$, —$(CH_2)_nOC(=Y)NR^5R^6$, —$(CH_2)_nC(=Y)OR^5$, —$(CH_2)_nNR^5R^6$, —$(CH_2)_nNR^5C(=Y)R^6$, —$(CH_2)_nNR^5C(=Y)OR^6$, —$(CH_2)_nNR^5C(=Y)NR^5R^6$, or —$(CH_2)_nNR^5S(O)_dR^6$ (wherein each methylene group may be substituted by one or more halogen atoms), each of which may be optionally substituted at any available position by one or more substituents $R^a$;

T, U, V and W are same or different and independently represent hydrogen or halogen;

$R^5$ and $R^6$ are same or different and are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-8}$ cycloalkyl, heterocyclyl, aryl, heteroaryl, aryloxy, —$(CH_2)_n$-cycloalkyl, —$(CH_2)_n$-heterocyclyl, —$(CH_2)_n$-aryl, —$(CH_2)_n$-heteroaryl, each of which may be optionally substituted at any available position with halogen, hydroxyl, $C_{1-12}$ alkyl, $C_{2-12}$ alkenyl, $C_{2-12}$ alkynyl, $C_{1-12}$ alkoxy, $C_{1-12}$ alkylcarbonyl, $C_{1-12}$ alkoxycarbonyl, $C_{3-8}$ cycloalkyl, $C_{1-12}$ haloalkyl, $C_{1-12}$ haloalkoxy, $C_{1-12}$ haloalkenyl, aryl, heterocyclyl, heteroaryl, —$(CH_2)_n$-aryl, —$(CH_2)_n$-heterocyclyl, —$(CH_2)_n$-heteroaryl, —$(CH_2)_n$-cycloalkyl, —CN, —$OR^7$, —$NO_2$, —$NR^7R^8$, —$N(R^7)C(=Y)R^8$, —$N(R^7)C(=Y)OR^8$, —$N(R^7)C(=Y)NR^7R^8$, —$C(=Y)R^7$, —$C(=Y)NR^7R^8$, —$OC(=Y)R^7$, —$OC(=Y)NR^7R^8$, —$C(=Y)OR^7$, —$OC(=Y)OR^7$, —$SR^7$, —$S(O)_dR^7$, —$SO_2NR^7R^8$, —$NR^7SO_2R^8$, —$OP(=O)R^7R^8$, —$NHP(=O)R^7R^8$, or —$P(=O)R^7R^8$; or $R^5$ and $R^6$ may be joined together along with the heteroatom to which they are joined to form a heterocyclic or heteroaryl ring which may additionally contain from one to three heteroatoms independently selected from O, S or N, the ring formed may optionally be substituted with one or more substituents selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-8}$ cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, —$C_{1-12}$ alkylcarbonyl, —$C_{1-12}$ alkoxycarbonyl, —CN, —$OR^7$, —$CF_3$, —$OCF_3$—$CH_2CF_3$, —$CF_2CF_3$, —$NO_2$, —$NR^7R^8$, —$N(R^7)C(=Y)R^8$, —$N(R^7)C(=Y)OR^8$, —$N(R^7)C(=Y)NR^7R^8$, —$C(=Y)R^7$, —$C(=Y)NR^7R^8$, —$OC(=Y)R^7$, —$OC(=Y)NR^7R^8$, —$OC(=Y)OR^7$, —$C(=Y)OR^7$, —$SR^7$, —$S(O)_dR^7$, —$SO_2NR^7R^8$; —$NR^7SO_2R^8$, —$OP(=O)R^7R^8$, —$NHP(=O)R^7R^8$, or —$P(O)R^7R^8$; the ring thus formed may further be fused with 3 to 7 membered unsaturated or saturated ring, which may contain from one to three heteroatoms independently selected from O, S or N, the fused ring may optionally be substituted at any available position by one or more substituents $R^a$;

$R^a$ is independently selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, oxo, $C_{1-12}$ alkoxy, $C_1$-$C_6$alkoxy$C_1$-$C_6$alkyl, $C_1$-$C_6$alkoxy$C_1$-$C_6$alkoxy$C_1$-$C_3$alkyl, $C_{1-12}$ haloalkoxy, $C_{3-8}$ cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, —$C_{1-12}$ alkylcarbonyl, —$C_{1-12}$ alkoxycarbonyl, —CN, —$YR^7$, —$(CH_2)_nYR^7$, —$NO_2$, =$NOR^7$, —$NR^7R^8$, —$N(R^7)C$ (=Y)R⁸, —N(R⁷)C(=Y)OR⁸, —N(R⁷)C(=Y)NR⁷R⁸, —C(=Y)R⁷, —C(=Y)NR⁷R⁸, —OC(=Y)R⁷, —OC(=Y)NR⁷R⁸, —C(=Y)OR⁷, —OC(=Y)OR⁷, —SR⁷, —S(O)$_d$R⁷, —SO₂NR⁷R⁸, —OP(=O)R⁷R⁸, —NHP(=O)R⁷R⁸, —P(O)R⁷R⁸, —(CH₂)$_n$CN, —YR⁷, —(CH₂)$_n$YR⁷, —NO₂, =NOR⁷, —(CH₂)$_n$NR⁷R⁸, —(CH₂)$_n$N(R⁷)C(=Y)R⁸, —(CH₂)$_n$N(R⁷)C(=Y)OR⁸, —(CH₂)$_n$N(R⁷)C(=Y)NR⁷R⁸, —(CH₂)$_n$C(=Y)R⁷, —(CH₂)$_n$C(=Y)NR⁷R⁸, —(CH₂)$_n$OC(=Y)R⁷, —(CH₂)$_n$OC(=Y)NR⁷R⁸, —(CH₂)$_n$C(=Y)OR⁷, —(CH₂)$_n$OC(=Y)OR⁷, —(CH₂)$_n$SR⁷, —(CH₂)$_n$S(O)$_d$R⁷, —(CH₂)$_n$SO₂NR⁷R⁸, —(CH₂)$_n$OP(=O)R⁷R⁸, —(CH₂)$_n$NHP(=O)R⁷R⁸, or —(CH₂)$_n$P(O)R⁷R⁸; each of which may optionally be substituted at any available position by one or more substituents selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, oxo, $C_1$-$C_{12}$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-8}$ cycloalkyl, heterocyclyl, aryl, heteroaryl, —(CH₂)$_n$-cycloalkyl, —(CH₂)$_n$-heterocyclyl, —(CH₂)$_n$-aryl, —(CH₂)$_n$-heteroaryl, —$C_{1-12}$ alkylcarbonyl, —$C_{1-12}$ alkoxycarbonyl, —CN, —OR⁹, —(CH₂)$_n$OR⁹, —CF₃, —NO₂, —NR⁹R¹⁰, —N(R⁹)C(=Y)R¹⁰, —N(R⁹)C(=Y)OR¹⁰, —N(R⁹)C(=Y)NR⁹R¹⁰, —C(=Y)R⁹, —C(=Y)NR⁹R¹⁰, —OC(=Y)R⁹, —OC(=Y)NR⁹R¹⁰, —OC(=Y)OR⁹, —C(=Y)OR⁹, —SR⁹, —S(O)$_d$R⁹, —SO₂NR⁹R¹⁰, —NR⁹SO₂R¹⁰, —OP(=O)R⁹R¹⁰, —NHP(=O)R⁹R¹⁰, —P(O)R⁹R¹⁰, —(CH₂)$_n$CN, —OR⁹, —(CH₂)$_n$OR⁹, —CF₃, —NO₂, -(CH₂)$_n$NR⁹R¹⁰, —(CH₂)$_n$N(R⁹)C(=Y)R¹⁰, —(CH₂)$_n$N(R⁹)C(=Y)OR¹⁰, —(CH₂)$_n$N(R⁹)C(=Y)NR⁹R¹⁰, -(CH₂)$_n$C(=Y)R⁹, —(CH₂)$_n$C(=Y)NR⁹R¹⁰, —(CH₂)$_n$OC(=Y)R⁹, —(CH₂)$_n$OC(=Y)NR⁹R¹⁰, —(CH₂)$_n$OC(=Y)OR⁹, —(CH₂)$_n$C(=Y)OR⁹, —(CH₂)$_n$SR⁹, —(CH₂)$_n$S(O)$_d$R⁹, —(CH₂)$_n$SO₂NR⁹R¹⁰; —(CH₂)$_n$NR⁹SO₂R¹⁰, —(CH₂)$_n$OP(=O)R⁹R¹⁰, —(CH₂)$_n$NHP(=O)R⁹R¹⁰, or —(CH₂)$_n$P(O)R⁹R¹⁰;

R⁷ and R⁸ are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{3-8}$ cycloalkyl, heterocyclyl, aryl, heteroaryl, —(CH₂)$_n$-cycloalkyl, —(CH₂)$_n$-heterocyclyl, —(CH₂)$_n$-aryl, or —(CH₂)$_n$-heteroaryl, each of which may be optionally substituted with halogen, hydroxyl or $C_{1-6}$ alkoxy, or R⁷ and R⁸ may be joined together along with the heteroatom to which they are attached to form a heterocyclic or heteroaryl ring which may contain from one to three heteroatoms independently selected from O, S or N, each of which may be optionally substituted with halogen, hydroxyl, $C_{1-6}$ alkyl or $C_{1-6}$ alkoxy.

R⁹ and R¹⁰ are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{3-8}$ cycloalkyl, heterocyclyl, aryl, heteroaryl, —(CH₂)$_n$-cycloalkyl, —(CH₂)$_n$-heterocyclyl, —(CH₂)$_n$-aryl, or —(CH₂)$_n$-heteroaryl, each of which may be optionally substituted with halogen, hydroxyl or $C_{1-6}$ alkoxy, or R⁹ and R¹⁰ may be joined together along with the heteroatom to which they are attached to form a heterocyclic or heteroaryl ring which may contain from one to three heteroatoms independently selected from O, S or N, each of which may be optionally substituted with halogen, hydroxyl, $C_{1-6}$ alkyl or $C_{1-6}$ alkoxy.

a and a' are same or different and independently represent 1,2,3 or 4;
m is 1, 2, 3 or 4;
m' is 0, 1, 2, 3 or 4;
n is 1, 2, 3 or 4;
d is 1 or 2.

with the proviso that when both R¹ and R² are hydrogen, Y and Y' are oxygen, R³ is hydrogen, A is nitrogen, '___' is absent, a and a' are both 2, T is fluorine, W, U and V are hydrogen, m is 1 and m' is 0, then Z does not represent

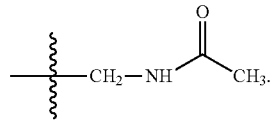 [SMILES: *CNC(C)=O]

One embodiment of the present invention provides compounds of Formula Ia, wherein

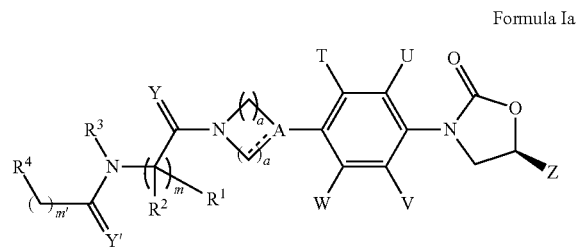

Formula Ia

R¹, R², R³, R⁴, Y, Y', A, T, U, V, W, Z, m, m', a and a' are as defined herein;
their pharmaceutically acceptable derivatives, tautomeric forms, stereoisomers including R and S isomers, polymorphs, prodrugs, metabolites, salts or solvates thereof.

Another embodiment of the present invention provides compounds of Formula Ib, wherein

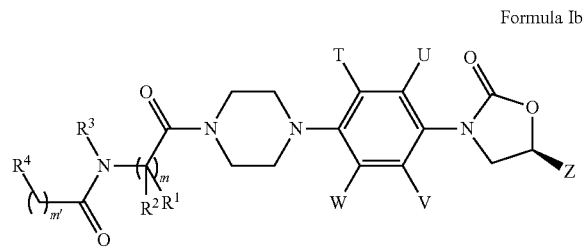

Formula Ib

R¹, R², R³, R⁴, T, U, V, W, Z, m, m' are as defined herein;
their pharmaceutically acceptable derivatives, tautomeric forms, stereoisomers including R and S isomers, polymorphs, prodrugs, metabolites, salts or solvates thereof.

In another embodiment of the compounds of the present invention, R¹ and R² are independently selected from hydrogen, $C_{1-12}$ alkyl, $C_{2-12}$ alkenyl, $C_{2-12}$ alkynyl, $C_{3-8}$ cycloalkyl or aryl, each of which may optionally be substituted at any available position by one or more substituents $R^a$ or R¹ and R² together with the carbon atom to which they are attached form a 3 to 10 membered monocyclic ring, partially unsaturated or saturated, which may contain from one to three heteroatoms independently selected from O, S or N, the ring thus formed may be fused with one or two rings independently selected from the group comprising an aryl ring, a cycloalkyl ring, a heterocyclyl ring or monocyclic heteroaryl ring; the ring thus formed can be optionally substituted at any available position by one or more substituents $R^a$;

In another embodiment of the compounds of the present invention R³ is selected from hydrogen, $C_{1-12}$ alkyl, $C_{2-12}$ alkenyl or $C_{2-12}$ alkynyl, each of which may be optionally substituted at any available position by one or more substituents $R^a$.

In another embodiment of the compounds of the present invention, $R^4$ is selected from hydrogen, halogen, $C_{1-12}$ alkyl, $C_{2-12}$ alkenyl, $C_{2-12}$ alkynyl, $C_{3-20}$cycloalkyl, heterocyclyl, aryl or heteroaryl, each of which may be optionally substituted at any available position by one or more substituents $R^a$.

In a further embodiment of the compounds of the present invention, it is preferred that $R^4$ is selected from hydrogen, $C_{1-12}$ alkyl, —CH$_2$OH, aryl, $C_{3-8}$ cycloalkyl,

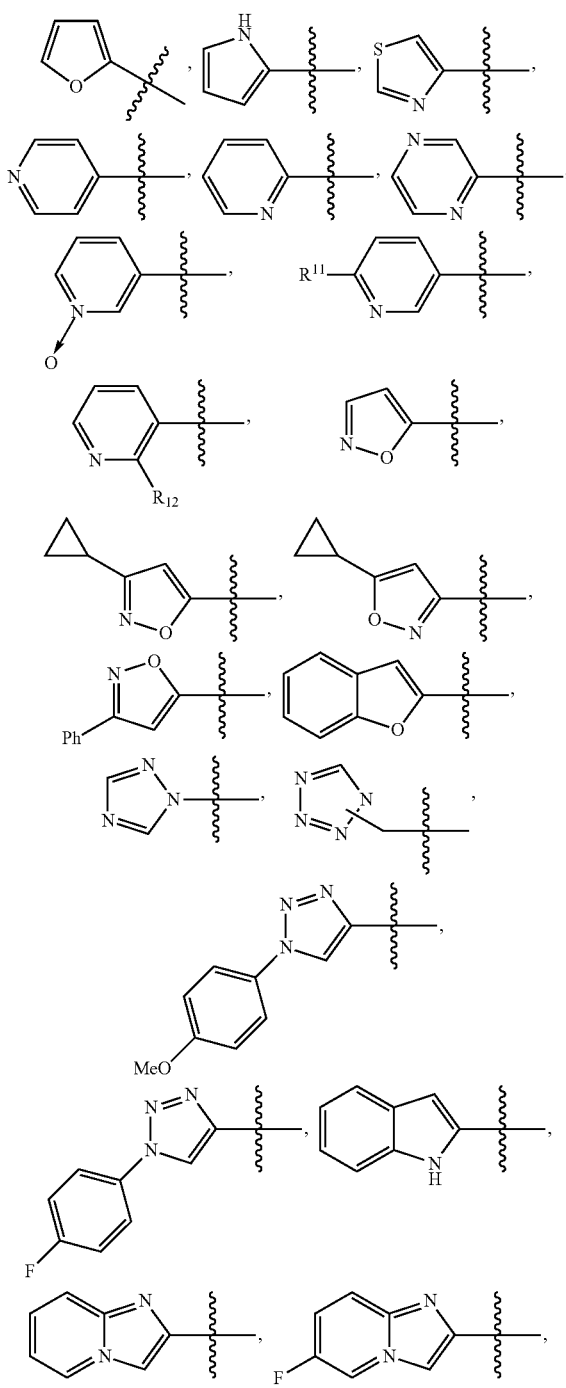

wherein $R^{11}$ is selected from —H, —CH$_3$, —OH, —F, —Cl, or —N(morpholine)

wherein $R^{12}$ is selected from —H, —CH$_3$, —OH, —Cl, or —F

In a further embodiment of the compounds of the present invention, it is preferred that T, U, V and W are same or different and represent fluorine or hydrogen.

In another embodiment of the compounds of the present invention, it is further preferred that T and W independently represent fluorine and U and V both represent hydrogen.

In another embodiment of the compounds of the present invention, m is selected from 1 or 2 and m' is selected from 0 or 1.

In another embodiment of the compounds of the present invention, Z is selected from $C_{1-12}$ alkyl, $C_{1-12}$ haloalkyl, heterocyclyl, heteroaryl, —(CH$_2$)$_n$-heterocyclyl, —(CH$_2$)$_n$-heteroaryl, —OC(=O)OR$^5$, —(CH$_2$)$_n$OR$^5$, —(CH$_2$)$_n$OP (=O)R$^5$R$^6$, —(CH$_2$)$_n$OC(=O)R$^5$, —(CH$_2$)$_n$OC(=O)OR$^5$, —(CH$_2$)$_n$C(=O)R$^5$, —(CH$_2$)$_n$C(=O)NR$^5$R$^6$, —(CH$_2$)$_n$OC (=O)NR$^5$R$^6$, —(CH$_2$)$_n$C(=O)OR$^5$, —(CH$_2$)$_n$NR$^5$R$^6$, —(CH$_2$)$_n$NR$^5$C(=O)R$^6$, —(CH$_2$)$_n$NR$^5$C(=O)OR$^6$, —(CH$_2$)$_n$NR$^5$C(=S)R$^6$, —(CH$_2$)$_n$NR$^5$C(=S)OR$^6$ (wherein each methylene group may be substituted by one or more halogen atoms), each of which may be optionally substituted at any available position by one or more substituents $R^a$.

In a further embodiment of the compounds of the present invention, it is preferred that Z is selected from —CH₂OH, —CH₂F, —CHF₂,
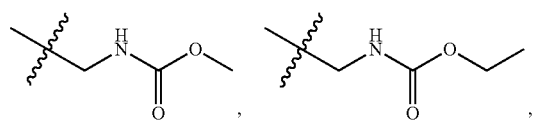
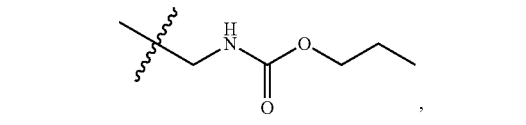
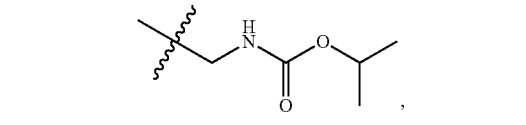
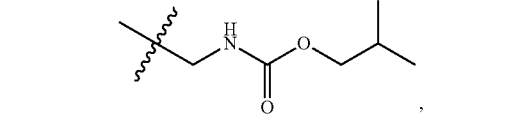
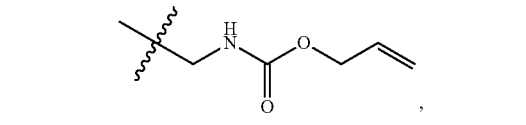
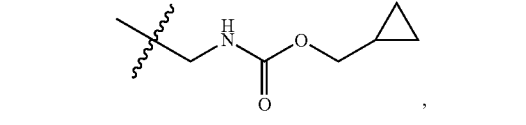
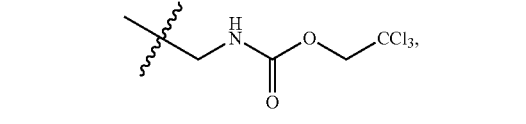
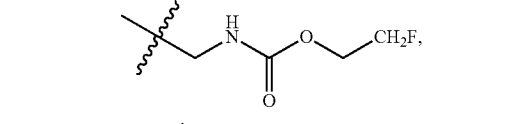
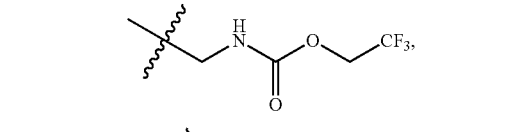
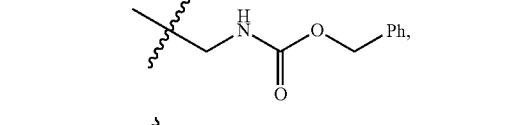
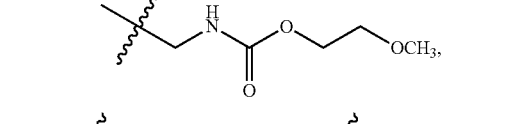
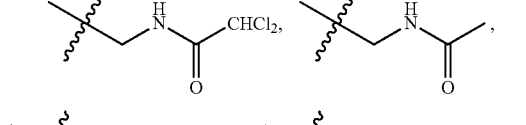
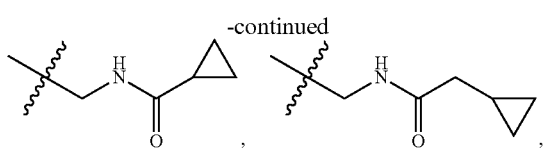
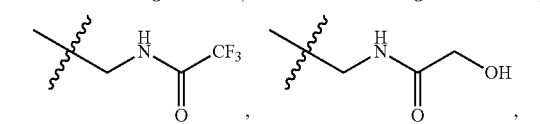
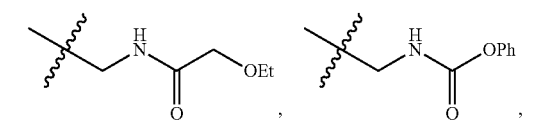
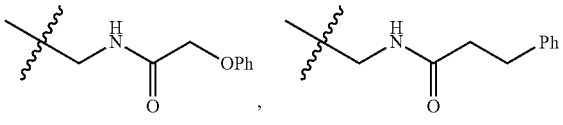
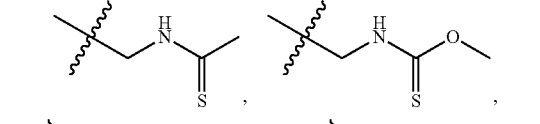
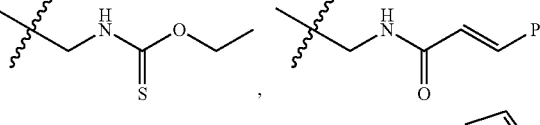
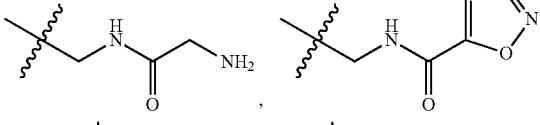
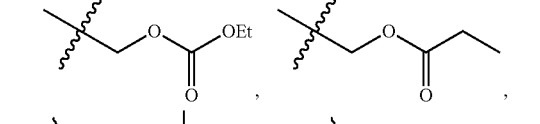
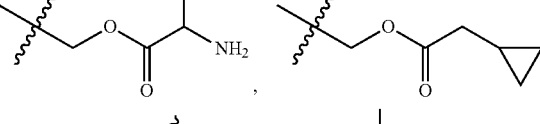
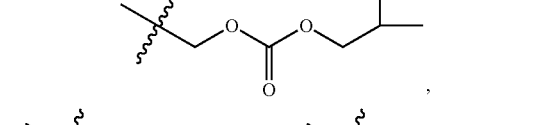
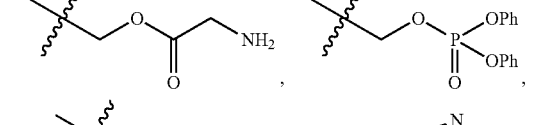
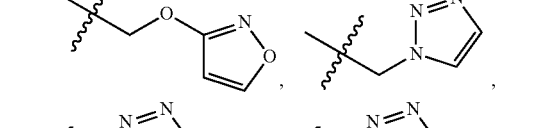
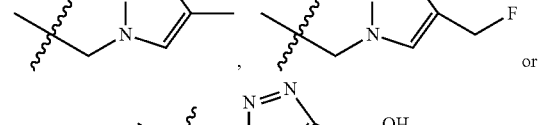
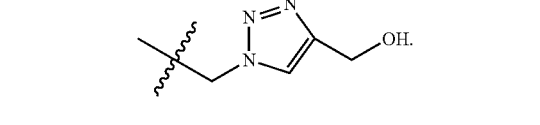

Definitions

Relative to the above description of the oxazolidinone compounds of the present invention, the following definitions apply.

The term "alkyl" as used herein refers to a straight or branched hydrocarbon chain, having from 1 to 12 carbon atoms. Examples of alkyl include, but are not limited to, for example, methyl, ethyl, n-propyl, isoprppyl, n-butyl, n-pentyl, t-butyl and the like. These groups may further be substituted with one or more substituents selected from but not limited to, for example, halogen, hydroxyl, oxo, carboxyl, carboxyalkyl, azido, cyano, amino, nitro, alkenyl, alkynyl, alkoxy, cycloalkyl, acyl acyloxy, aryl, heterocyclyl and heteroaryl.

The term "alkenyl" as used herein refers to an aliphatic hydrocarbon group containing at least one carbon-carbon double bond and which may be straight or branched hydrocarbon chain having from 1 to 12 carbon atoms. Examples of alkenyl include, but are not limited to, for example, ethenyl, 1-propenyl, 2-propenyl, iso-propenyl, 1-butenyl, 2-butenyl, and the like.

These groups may further be substituted with one or more substituents selected from but not limited to, for example, halogen, hydroxyl, oxo, carboxyl, carboxyalkyl, azido, cyano, amino, nitro, alkenyl, alkynyl, alkoxy, cycloalkyl, acyl acyloxy, aryl, heterocyclyl and heteroaryl.

The term "alkynyl" as used herein refers to a straight or branched hydrocarbon group containing at least one carbon-carbon triple bond and which may be straight or branched chain having from 1 to 12 carbon atoms. . Examples of alkynyl include, but are not limited to, for example, ethynyl, propynyl, and butynyl. These groups may further be substituted with one or more substituents selected from but not limited to, for example, halogen, hydroxyl, oxo, carboxyl, carboxyalkyl, azido, cyano, amino, nitro, alkenyl, alkynyl, alkoxy, cycloalkyl, acyl acyloxy, aryl, heterocyclyl and heteroaryl.

The term "alkoxy" refers to an above defined alkyl group attached via an oxygen linkage to the rest of the molecule. Non-limiting examples of such groups include —$OCH_3$, —$OC_2H_5$ and the like.

"Halogen" refers to fluorine, chlorine, bromine or iodine.

The term "haloalkyl" refers to an above-defined "alkyl" group, which is substituted with one or more "halogen" groups, as defined herein, at any one or more of the 1 to 12 carbon atoms of the alkyl group. Representative examples of haloalkyl include, but are not limited to, chloromethyl, fluoromethyl, trifluoromethyl, trichloromethyl, difluoroethyl, trifluoroethyl, dichloroethyl, and the like.

The term "haloalkenyl" refers to an above-defined "alkenyl" group, which is substituted with one or more "halogen" groups, as defined herein, at any one or more of the carbon atoms of the alkenyl group. Representative examples of haloalkenyl include, but are not limited to, chloroethenyl, 2-fluroethenyl, triflurobutenyl and dichloropropenyl.

The term "haloalkynyl" refers to an above-defined "alkynyl" group, which is substituted with one or more "halogen" groups, as defined herein, at any one or more of the carbon atoms of the alkynyl group. Representative examples of haloalkynyl include, but are not limited to, 2-fluroethynyl, triflurobutynyl and dichloropropynyl.

The term "haloalkoxy" refers to an above defined "haloalkyl" group, appended to the parent molecular moiety through an oxygen atom.

The term "cycloalkyl" refers to cyclic alkyl groups constituting of 3 to 20 carbon atoms having a single cyclic ring or multiple condensed rings, for example, fused or spiro systems, unless otherwise constrained by the definition. Such cycloalkyl groups include, by way of example, single ring structures, for example, cyclopropyl, cyclobutyl, cyclopentenyl, cyclohexyl, cyclooctyl, and the like, or multiple ring structures, for example, adamantyl, and bicyclo[2.2.1]heptane, or cyclic alkyl groups to which is fused an aryl group, for example, indane and the like.

Cycloalkyl groups may further be substituted with one or more substituents selected from but not limited to, for example, halogen, hydroxyl, oxo, carboxy, carboxyalkyl, azido, alkenyl, alkynyl, alkoxy, cycloalkyl, acyl acyloxy, aryl, heterocyclyl, heteroaryl.

The term "aryl" herein refers to a mono- or poly-carbocyclic aromatic group, for example phenyl or naphthyl ring and the like optionally substituted with one or more substituents selected from but not limited to, for example, halogen, hydroxyl, alkyl, alkenyl, alkynyl, cycloalkyl, alkoxy, acyl, amino, aryloxy, $CF_3$, $COOR_d$ (wherein $R_d$ can be hydrogen, alkyl, alkenyl, cycloalkyl, aralkyl, heterocyclylalkyl or heteroarylalkyl), cyano, nitro, carboxy, heterocyclyl, heteroaryl, heterocyclylalkyl or heteroarylalkyl. The aryl group may optionally be fused with cycloalkyl group, heteroaryl group, heterocyclyl group or another aryl group. The fused group may be further substituted at any available position with one or more substituents selected from but not limited to, for example, halogen, hydroxyl, oxo, carboxy, amino, nitro, cyano, carboxyalkyl, azido, alkenyl, alkynyl, alkoxy, cycloalkyl, acyl, acyloxy, aryl, heterocyclyl, heteroaryl.

The term "aryloxy" refers to an above defined aryl group attached via an oxygen linkage to the rest of the molecule, for example —OPh and the like.

The term "heteroaryl" unless and otherwise specified refers to an aromatic monocyclic or polycyclic ring structure, fully or partially unsaturated, containing one to four heteroatoms independently selected from N, O or S. The nitrogen heteroatoms may optionally be oxidized. The nitrogen atoms may optionally be quaternerized. "Heteroaryl" also includes, but is not limited to, bicyclic or tricyclic rings, wherein the heteroaryl ring is fused to one or two rings independently selected from the group consisting of an aryl ring, a cycloalkyl ring, a heterocyclyl ring and another monocyclic heteroaryl ring. Examples of heteroaryl groups include, but not limited to, oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, thienyl, isoxazolyl, triazinyl, furanyl, benzofuranyl, indolyl, benzothiazolyl, benzoxazolyl, imidazo[1,2-a]pyrimidine, imidazo[1,2-a]pyrazine, and the like. The bicyclic or tricyclic heteroaryl rings can be attached either through the heteroaryl group itself or the aryl, cycloalkyl or heterocyclyl group to which it is fused. The heteroaryl group may be further substituted at any available position with one or more substituents selected from but not limited to, for example, halogen, hydroxyl, oxo, carboxy, amino, nitro, cyano, carboxyalkyl, azido, alkenyl, alkynyl, alkoxy, cycloalkyl, cycloalkynyl, acyl acyloxy, aryl, heterocyclyl, heteroaryl.

The term "heterocyclyl" unless otherwise specified refers to a non-aromatic monocyclic or polycyclic cycloalkyl group, fully or partially unsaturated, containing one or more heteroatom(s) independently selected from N, O or S. The heterocyclyl ring may be fused with another cycloalkyl, aryl, heterocyclyl or heteroaryl ring and are optionally benzofused or fused heteroaryl of 5-6 ring members and/or are optionally substituted wherein the substituents are selected from but not limited to halogen, hydroxyl, alkyl, alkenyl, alkynyl, cycloalkyl, acyl, carboxy, aryl, alkoxy, aralkyl, cyano, nitro, amino, heterocyclyl, or heteroaryl. Examples of heterocyclyl groups include but are not limited to, morpholinyl, oxazolidinyl, tetrahydrofuranyl, dihydrofuranyl, dihydropyridinyl, dihydroisooxazolyl, dihydrobenzofuryl, azabicyclohexyl, dihydroindonyl, piperidinyl or piperazinyl. The fused group may be further substituted at any available position with one or more substituents selected from but not limited to, for example, halogen, hydroxyl, oxo, carboxy, amino, nitro, cyano, carboxyalkyl, azido, alkenyl, alkynyl, alkoxy, cycloalkyl, acyl acyloxy, aryl, heterocyclyl, heteroaryl. The nitrogen and sulphur heteroatoms may optionally be oxidized. The nitrogen atoms may optionally be quaternerized.

"Hydroxy" or "hydroxyl" refers to the group —OH.

The term "Protecting Group" or "PG" refers to a group which is in a modified form to preclude undesired side reactions at the protected site. The term protecting group, unless otherwise specified, may be used with groups, for example, hydroxyl, amino, carboxyl and examples of such groups are found in T. W. Greene. et al. *"Protecting Groups in Organic Synthesis,"* 3$^{rd}$ Ed, Wiley, New York, which is incorporated herein by reference. The species of the carboxylic protecting groups, amino protecting groups or hydroxyl protecting groups employed are not critical, as long as the derivatised moieties/moiety is/are stable to conditions of subsequent reactions and can be removed without disrupting the remainder of the molecule. Examples of suitable hydroxyl and amino protecting groups include but are not limited to trimethylsilyl, triethylsilyl, o-nitrobenzyloxycarbonyl, p-nitrobenzyloxycarbonyl, t-butyldiphenylsilyl, t-butyldimethylsilyl, acetyl, trifluoroacetyl, benzyloxycarbonyl (CBz), t-butoxycarbonyl (Boc), 9-fluorenylethylenoxycarbonyl (Fmoc), 2,2,2-trichloroethyloxycarbonyl, allyloxycarbonyl and the like. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl, t-butyl and the like.

"Subject" includes humans, non-human mammals (e.g., dogs, cats, rabbits, cattle, horses, sheep and the like) or non-mammals (e.g., birds and the like).

The term "therapeutically effective amount" means the amount of a compound that, when administered to a subject for treating a disease, is sufficient to effect such treatment for the disease. The "therapeutically effective amount" will vary depending on the compound, the disease and its severity, weight, physical condition and responsiveness of the subject to be treated, among other factors.

A "pharmaceutically acceptable salt" encompasses any compound according to the present invention that is utilized in the form of a salt thereof, especially where the salt confers on a compound improved pharmacokinetic properties as compared to the free form of compound or a different salt form of the compound.

Asymmetric centres may exist in the compounds of the present invention. The compounds of Formula I may have one or more stereogenic centres and so can exhibit optical isomerism. All such isomers including enantiomers, diastereomers, and epimers are included within the scope of this invention. Furthermore, the invention includes such compounds as single isomers (R and/or S) and as mixtures, including racemates. If desired, racemic mixtures of the compounds may be separated so that the individual enantiomers are isolated. The separation may be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Starting materials of particular stereochemistry may either be commercially available or may be made by the methods described herein and resolved by techniques well known in the art. The independent syntheses of these diastereomers or their chromatographic separations may be achieved as known in the art by appropriate modifications.

Certain compounds according to Formula I, can also exist as tautomers, which have different points of attachment of hydrogen accompanied by one or more double bond shifts. These tautomers, either separately or as mixtures, are also considered to be within the scope of the invention.

Certain compounds according to Formula I, may also exist as polymorphs.

The present invention also encompasses geometrical isomers of compounds of Formula I and the mixtures thereof.

Particularly useful examples of the present invention include but are not limited to the compounds selected from Table 1:

TABLE 1

| Compound No. | Structure |
|---|---|
| 1 | 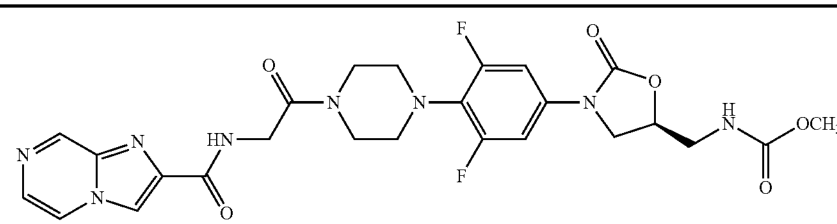 |
| 2 | 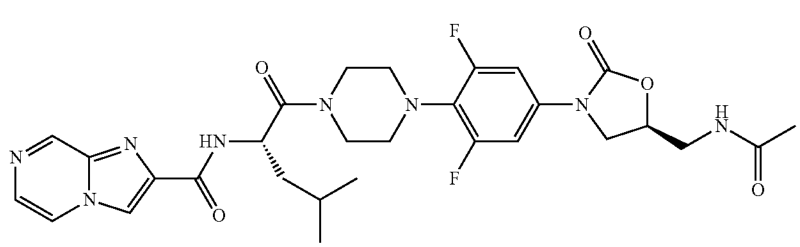 [SMILES: CC(=O)NC[C@H]1CN(c2cc(F)c(N3CCN(C(=O)[C@H](CC(C)C)NC(=O)c4cn5ccncc5n4)CC3)c(F)c2)C(=O)O1] |

TABLE 1-continued

| Compound No. | Structure |
|---|---|
| 3 | 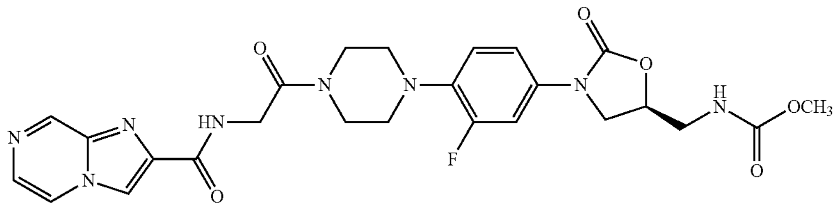 [SMILES: COC(=O)NC[C@H]1CN(c2ccc(N3CCN(C(=O)CNC(=O)c4cn5ccncc5n4)CC3)c(F)c2)C(=O)O1] |
| 4 | 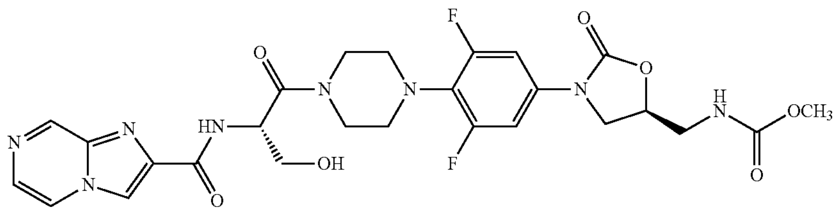 [SMILES: COC(=O)NC[C@H]1CN(c2cc(F)c(N3CCN(C(=O)[C@H](CO)NC(=O)c4cn5ccncc5n4)CC3)c(F)c2)C(=O)O1] |
| 5 | 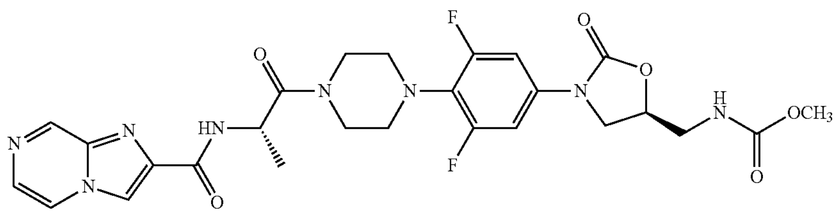 [SMILES: COC(=O)NC[C@H]1CN(c2cc(F)c(N3CCN(C(=O)[C@H](C)NC(=O)c4cn5ccncc5n4)CC3)c(F)c2)C(=O)O1] |
| 6 | 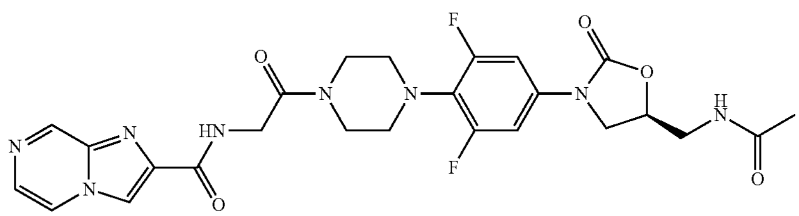 [SMILES: CC(=O)NC[C@H]1CN(c2cc(F)c(N3CCN(C(=O)CNC(=O)c4cn5ccncc5n4)CC3)c(F)c2)C(=O)O1] |
| 7 | 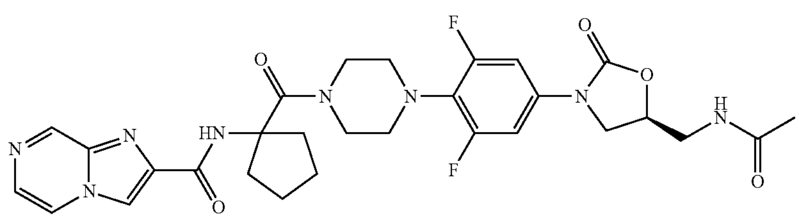 [SMILES: CC(=O)NC[C@H]1CN(c2cc(F)c(N3CCN(C(=O)C4(NC(=O)c5cn6ccncc6n5)CCCC4)CC3)c(F)c2)C(=O)O1] |
| 8 | 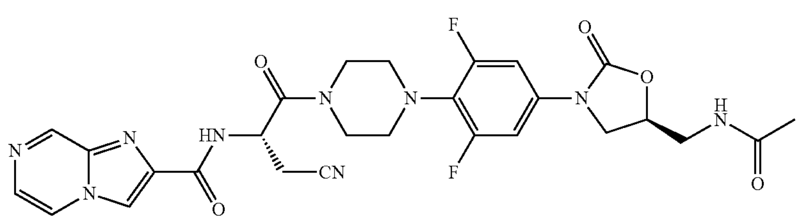 [SMILES: CC(=O)NC[C@H]1CN(c2cc(F)c(N3CCN(C(=O)[C@H](CC#N)NC(=O)c4cn5ccncc5n4)CC3)c(F)c2)C(=O)O1] |
| 9 | 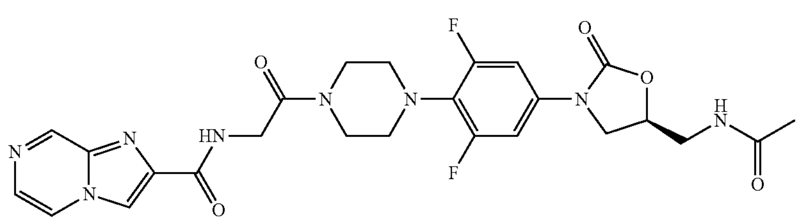 [SMILES: CC(=O)NC[C@H]1CN(c2cc(F)c(N3CCN(C(=O)CNC(=O)c4cn5ccncc5n4)CC3)c(F)c2)C(=O)O1] |

TABLE 1-continued

| Compound No. | Structure |
|---|---|
| 10 | 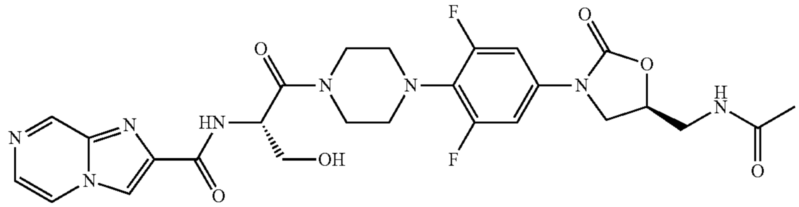 |
| 11 | 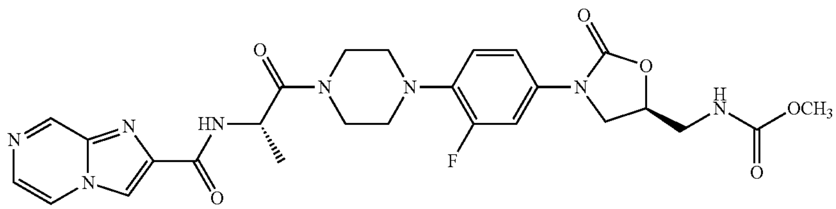 |
| 12 | 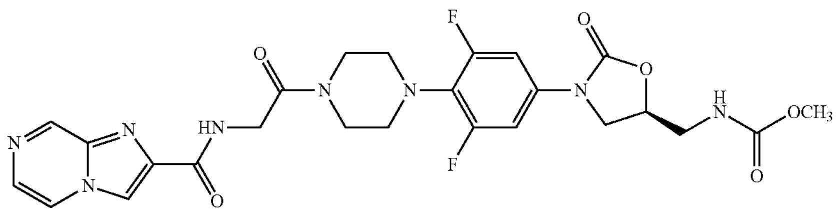 [SMILES: COC(=O)NC[C@H]1CN(c2cc(F)c(N3CCN(C(=O)CNC(=O)c4cn5ccncc5n4)CC3)c(F)c2)C(=O)O1] |
| 13 | 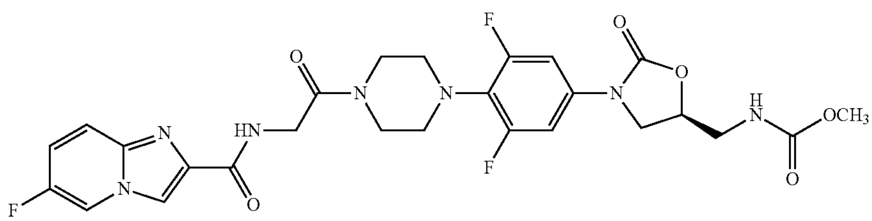 [SMILES: COC(=O)NC[C@H]1CN(c2cc(F)c(N3CCN(C(=O)CNC(=O)c4cn5cc(F)ccc5n4)CC3)c(F)c2)C(=O)O1] |
| 14 | 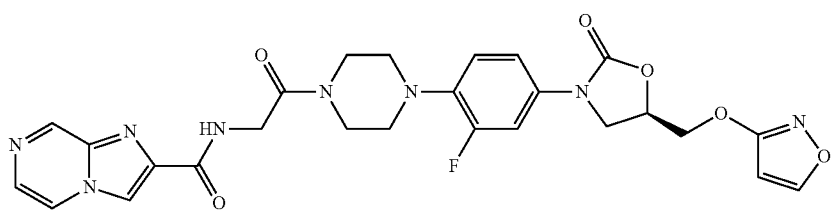 [SMILES: O=C(NCC(=O)N1CCN(c2ccc(N3C[C@H](COc4ccon4)OC3=O)cc2F)CC1)c1cn2ccncc2n1] |
| 15 | 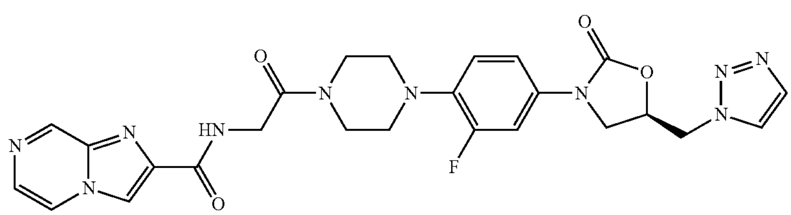 [SMILES: O=C(NCC(=O)N1CCN(c2ccc(N3C[C@H](Cn4ccnn4)OC3=O)cc2F)CC1)c1cn2ccncc2n1] |
| 16 | 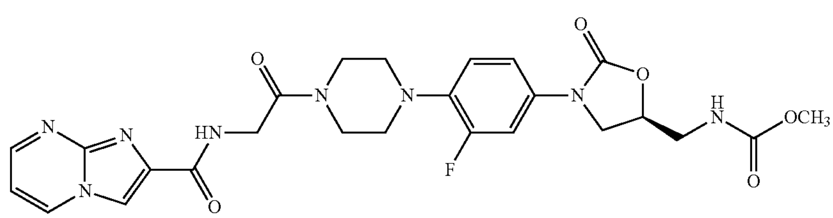 [SMILES: COC(=O)NC[C@H]1CN(c2ccc(N3CCN(C(=O)CNC(=O)c4cn5cccnc5n4)CC3)c(F)c2)C(=O)O1] |

TABLE 1-continued
| Compound No. | Structure |
|---|---|
| 17 | 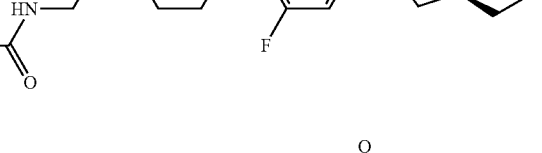 |
| 18 | 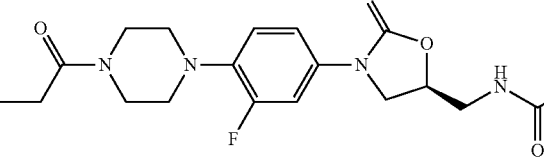 |
| 19 | 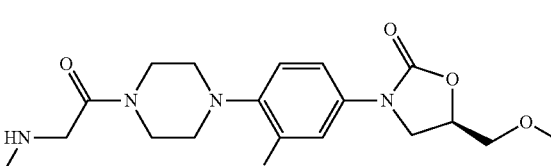 |
| 20 | 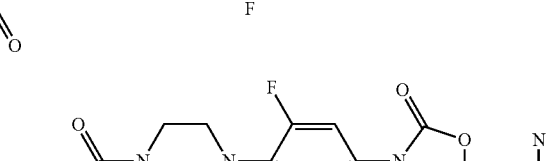 |
| 21 | 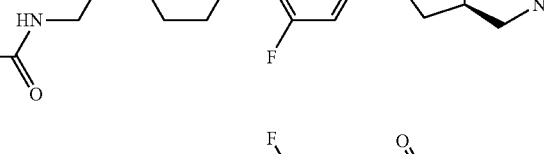 |
| 22 | 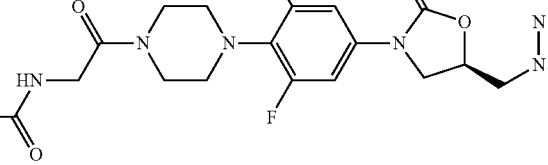 |
| 23 | 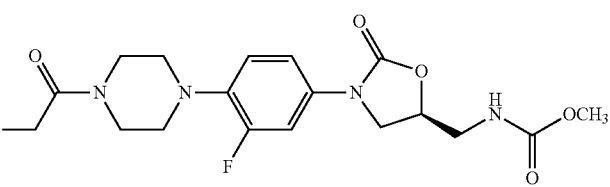 |

TABLE 1-continued

| Compound No. | Structure |
|---|---|
| 24 | 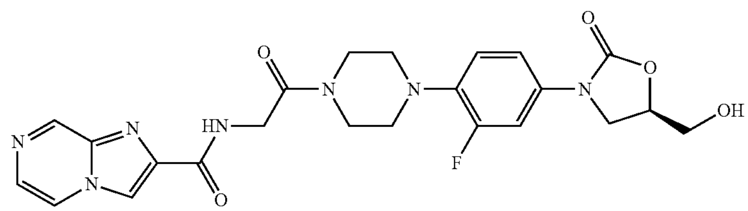 [SMILES: O=C(NCC(=O)N1CCN(c2ccc(N3C[C@H](CO)OC3=O)cc2F)CC1)c1cn2ccncc2n1] |
| 25 | 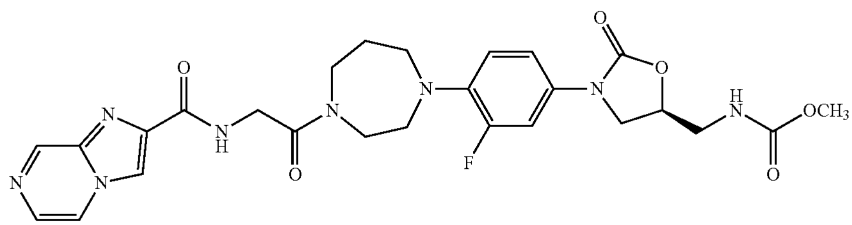 [SMILES: COC(=O)NC[C@H]1CN(c2ccc(N3CCCN(C(=O)CNC(=O)c4cn5ccncc5n4)CC3)c(F)c2)C(=O)O1] |
| 26 | 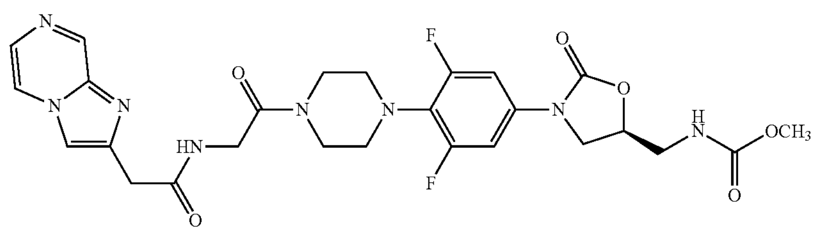 [SMILES: COC(=O)NC[C@H]1CN(c2cc(F)c(N3CCN(C(=O)CNC(=O)Cc4cn5ccncc5n4)CC3)c(F)c2)C(=O)O1] |
| 27 | 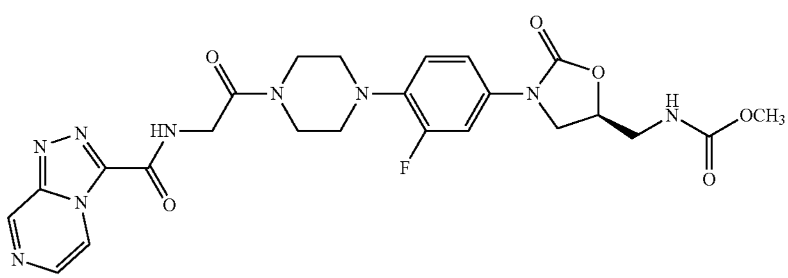 [SMILES: COC(=O)NC[C@H]1CN(c2ccc(N3CCN(C(=O)CNC(=O)c4nnc5cnccn45)CC3)c(F)c2)C(=O)O1] |
| 28 | 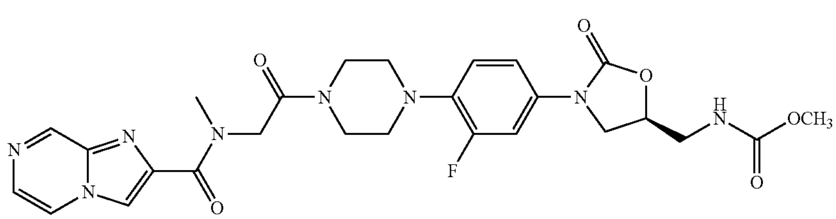 [SMILES: COC(=O)NC[C@H]1CN(c2ccc(N3CCN(C(=O)CN(C)C(=O)c4cn5ccncc5n4)CC3)c(F)c2)C(=O)O1] |
| 29 | 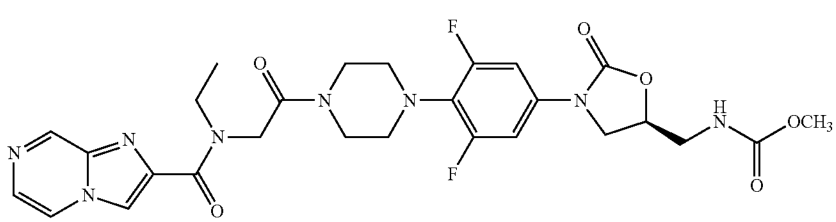 [SMILES: CCN(CC(=O)N1CCN(c2c(F)cc(N3C[C@H](CNC(=O)OC)OC3=O)cc2F)CC1)C(=O)c1cn2ccncc2n1] |

TABLE 1-continued

| Compound No. | Structure |
|---|---|
| 30 | 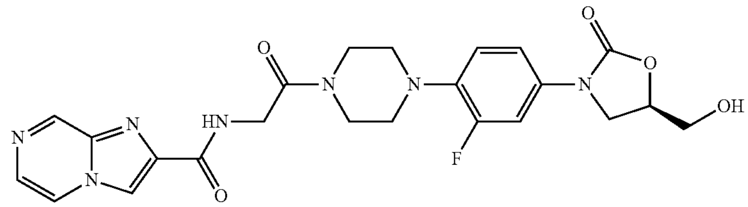 [SMILES: O=C(NCC(=O)N1CCN(c2ccc(N3C[C@H](CO)OC3=O)cc2F)CC1)c1cn2ccncc2n1] |
| 31 | 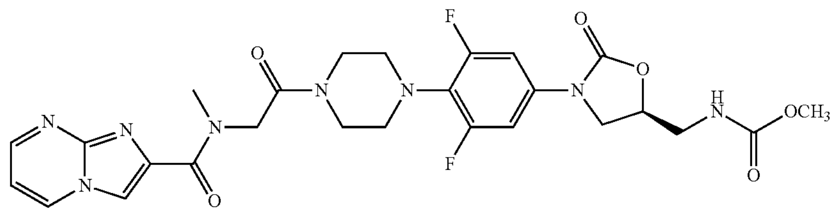 [SMILES: COC(=O)NC[C@H]1CN(c2cc(F)c(N3CCN(C(=O)CN(C)C(=O)c4cn5cccnc5n4)CC3)c(F)c2)C(=O)O1] |
| 32 | 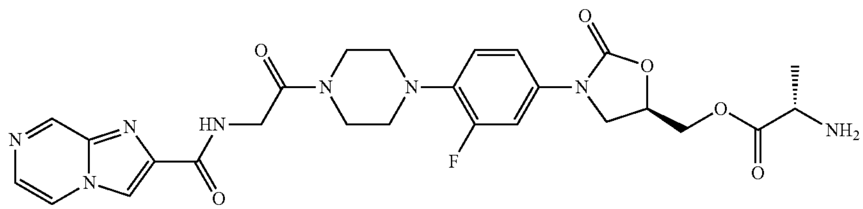 [SMILES: C[C@H](N)C(=O)OC[C@H]1CN(c2ccc(N3CCN(C(=O)CNC(=O)c4cn5ccncc5n4)CC3)c(F)c2)C(=O)O1] |
| 33 | 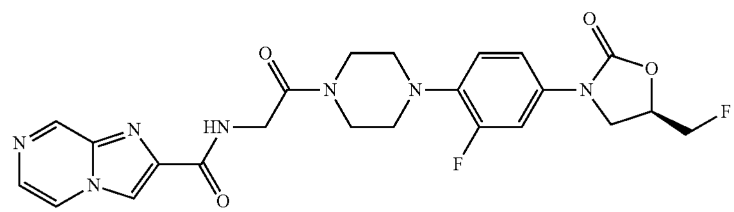 [SMILES: O=C(NCC(=O)N1CCN(c2ccc(N3C[C@H](CF)OC3=O)cc2F)CC1)c1cn2ccncc2n1] |
| 34 | 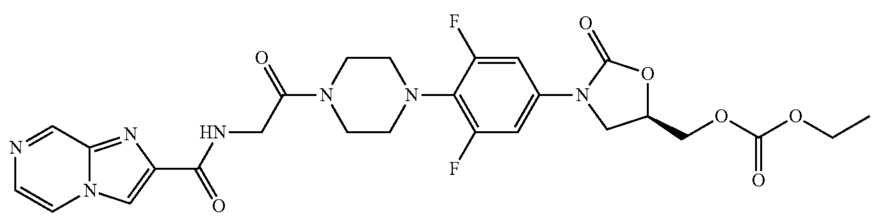 [SMILES: CCOC(=O)OC[C@H]1CN(c2cc(F)c(N3CCN(C(=O)CNC(=O)c4cn5ccncc5n4)CC3)c(F)c2)C(=O)O1] |
| 35 | 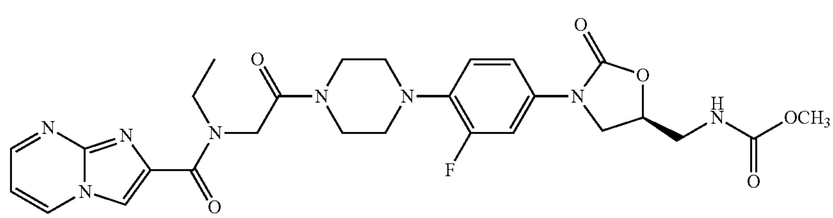 [SMILES: CCN(CC(=O)N1CCN(c2ccc(N3C[C@H](CNC(=O)OC)OC3=O)cc2F)CC1)C(=O)c1cn2cccnc2n1] |
| 36 | 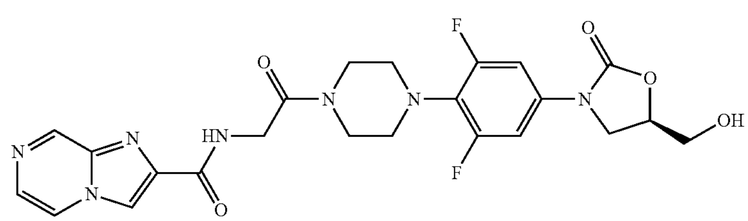 [SMILES: O=C(NCC(=O)N1CCN(c2c(F)cc(N3C[C@H](CO)OC3=O)cc2F)CC1)c1cn2ccncc2n1] |

TABLE 1-continued

| Compound No. | Structure |
|---|---|
| 37 | 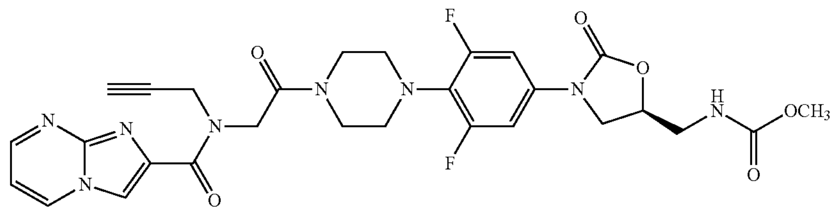 [SMILES: C#CCN(CC(=O)N1CCN(c2c(F)cc(N3C[C@H](CNC(=O)OC)OC3=O)cc2F)CC1)C(=O)c1cn2cccnc2n1] |
| 38 | 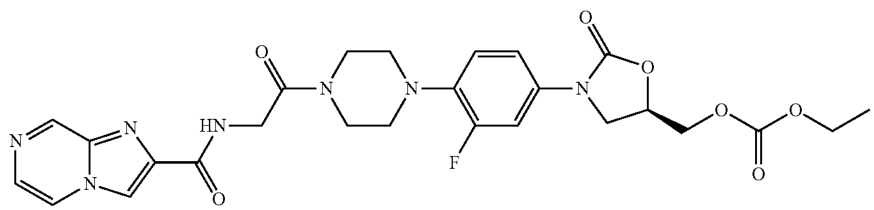 [SMILES: CCOC(=O)OC[C@H]1CN(c2ccc(N3CCN(C(=O)CNC(=O)c4cn5ccncc5n4)CC3)c(F)c2)C(=O)O1] |
| 39 | 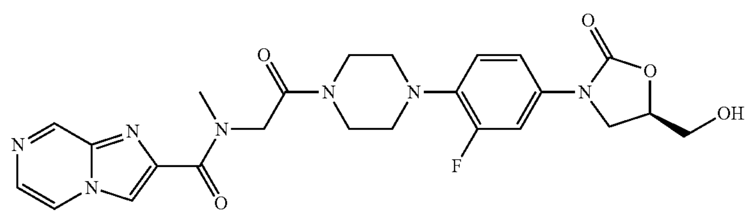 [SMILES: CN(CC(=O)N1CCN(c2ccc(N3C[C@H](CO)OC3=O)cc2F)CC1)C(=O)c1cn2ccncc2n1] |
| 40 | 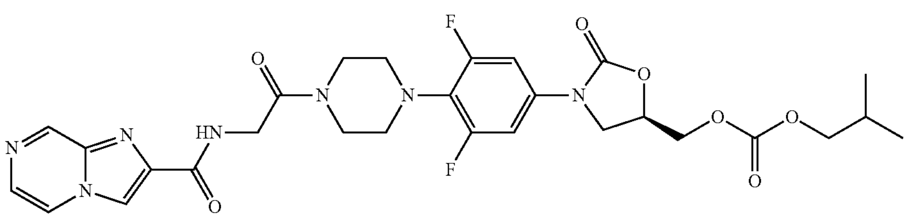 [SMILES: CC(C)COC(=O)OC[C@H]1CN(c2cc(F)c(N3CCN(C(=O)CNC(=O)c4cn5ccncc5n4)CC3)c(F)c2)C(=O)O1] |
| 41 | 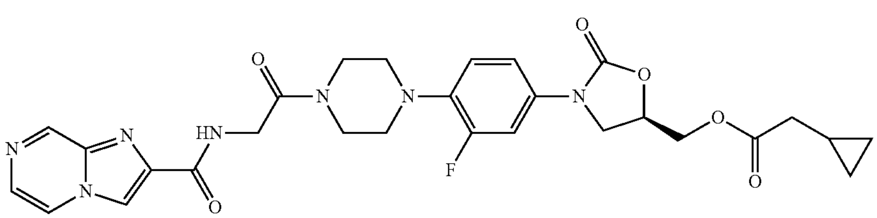 [SMILES: O=C(CC1CC1)OC[C@H]1CN(c2ccc(N3CCN(C(=O)CNC(=O)c4cn5ccncc5n4)CC3)c(F)c2)C(=O)O1] |
| 42 | 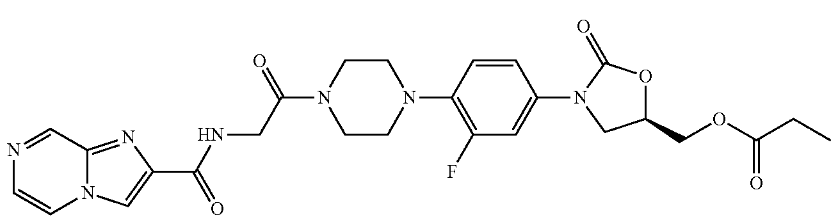 [SMILES: CCC(=O)OC[C@H]1CN(c2ccc(N3CCN(C(=O)CNC(=O)c4cn5ccncc5n4)CC3)c(F)c2)C(=O)O1] |
| 43 | 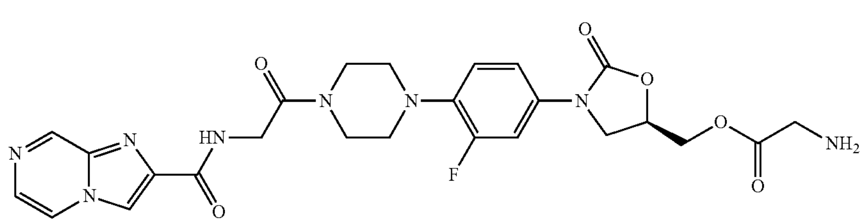 |

TABLE 1-continued

| Compound No. | Structure |
| --- | --- |
| 44 | 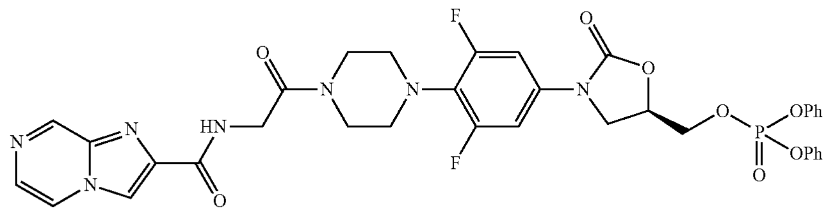 [SMILES: O=C(NCC(=O)N1CCN(c2c(F)cc(N3C[C@H](COP(=O)(Oc4ccccc4)Oc4ccccc4)OC3=O)cc2F)CC1)c1cn2ccncc2n1] |
| 45 | 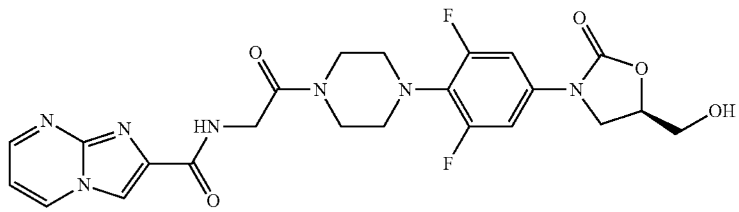 [SMILES: O=C(NCC(=O)N1CCN(c2c(F)cc(N3C[C@H](CO)OC3=O)cc2F)CC1)c1cn2cccnc2n1] |
| 46 | 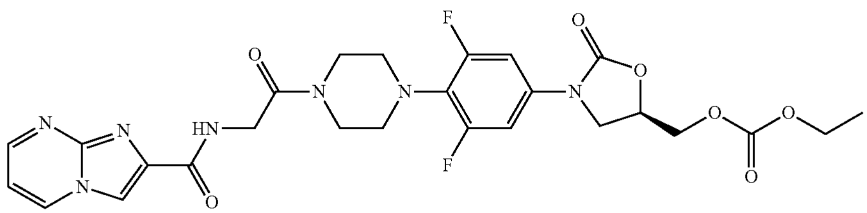 [SMILES: CCOC(=O)OC[C@H]1CN(c2cc(F)c(N3CCN(C(=O)CNC(=O)c4cn5cccnc5n4)CC3)c(F)c2)C(=O)O1] |
| 47 | 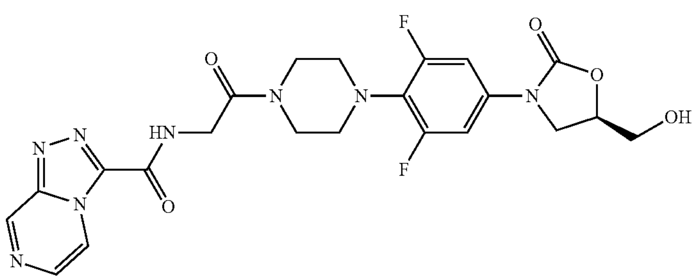 [SMILES: O=C(NCC(=O)N1CCN(c2c(F)cc(N3C[C@H](CO)OC3=O)cc2F)CC1)c1nnc2cnccn12] |
| 48 | 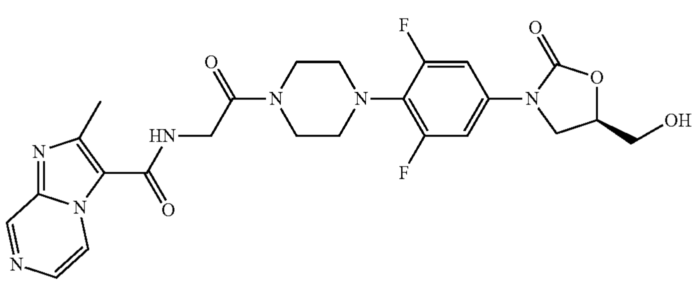 [SMILES: Cc1nc2cnccn2c1C(=O)NCC(=O)N1CCN(c2c(F)cc(N3C[C@H](CO)OC3=O)cc2F)CC1] |
| 49 | 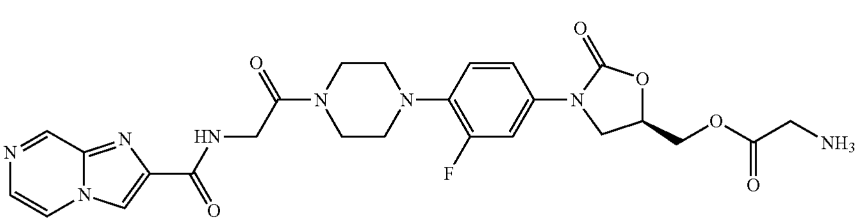 [SMILES: NCC(=O)OC[C@H]1CN(c2ccc(N3CCN(C(=O)CNC(=O)c4cn5ccncc5n4)CC3)c(F)c2)C(=O)O1] |

TABLE 1-continued

| Compound No. | Structure |
|---|---|
| 50 | [chemical structure] |
| 51 | [chemical structure] |
| 52 | [chemical structure] |
| 53 | [chemical structure] |
| 54 | [chemical structure] |
| 55 | [chemical structure] |
| 56 | [chemical structure] |

TABLE 1-continued
| Compound No. | Structure |
|---|---|
| 57 | 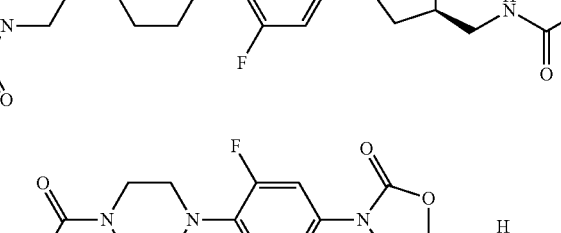 |
| 58 | 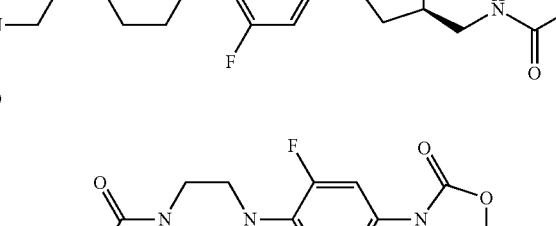 |
| 59 | 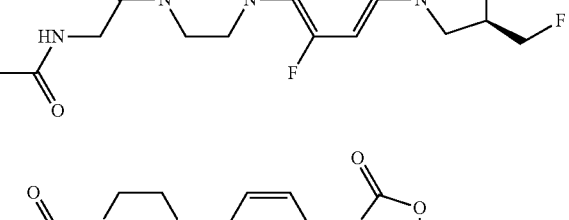 |
| 60 | 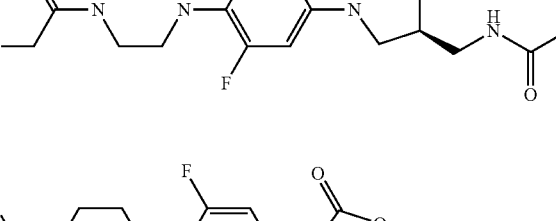 |
| 61 | 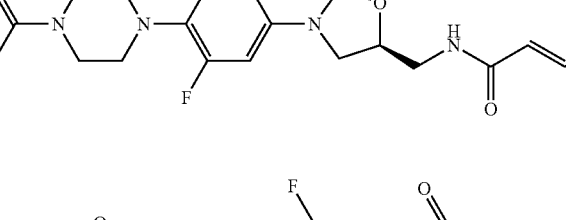 |
| 62 | 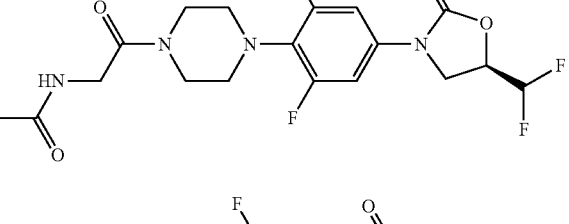 |
| 63 | 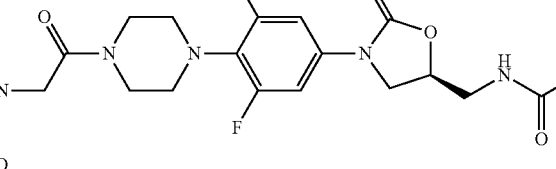 |

TABLE 1-continued

| Compound No. | Structure |
|---|---|
| 64 | 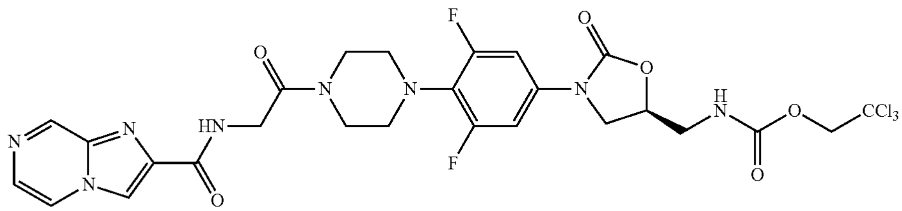 |
| 65 | 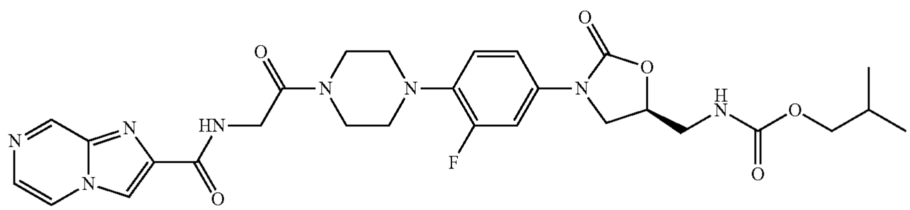 [SMILES: CC(C)COC(=O)NC[C@H]1CN(c2ccc(N3CCN(C(=O)CNC(=O)c4cn5ccncc5n4)CC3)c(F)c2)C(=O)O1] |
| 66 | 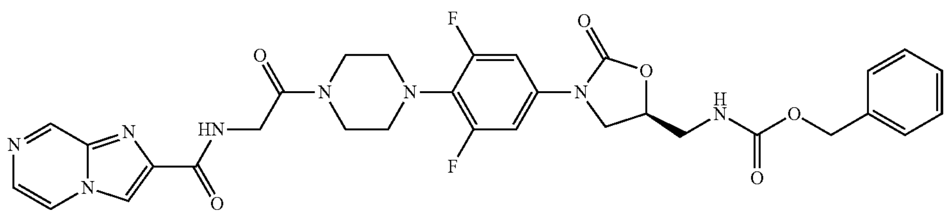 [SMILES: O=C(NC[C@H]1CN(c2cc(F)c(N3CCN(C(=O)CNC(=O)c4cn5ccncc5n4)CC3)c(F)c2)C(=O)O1)OCc1ccccc1] |
| 67 | 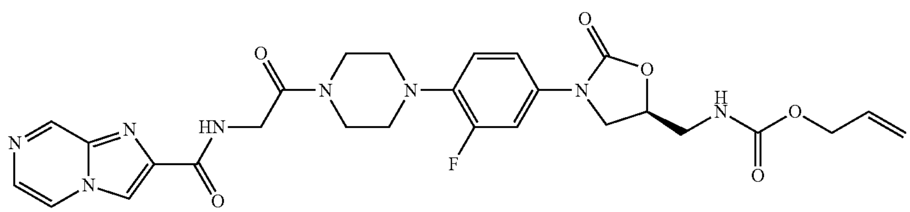 [SMILES: C=CCOC(=O)NC[C@H]1CN(c2ccc(N3CCN(C(=O)CNC(=O)c4cn5ccncc5n4)CC3)c(F)c2)C(=O)O1] |
| 68 | 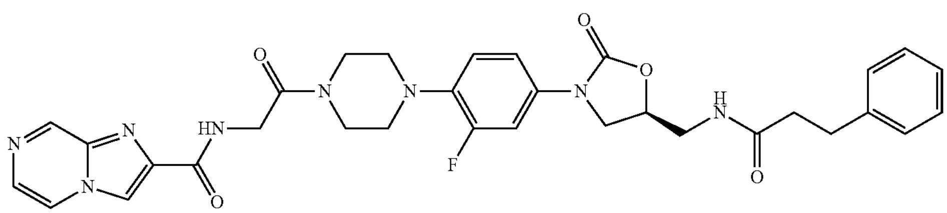 [SMILES: O=C(CCc1ccccc1)NC[C@H]1CN(c2ccc(N3CCN(C(=O)CNC(=O)c4cn5ccncc5n4)CC3)c(F)c2)C(=O)O1] |
| 69 | 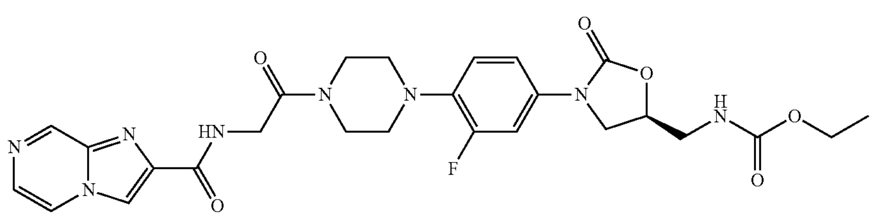 [SMILES: CCOC(=O)NC[C@H]1CN(c2ccc(N3CCN(C(=O)CNC(=O)c4cn5ccncc5n4)CC3)c(F)c2)C(=O)O1] |
| 70 | 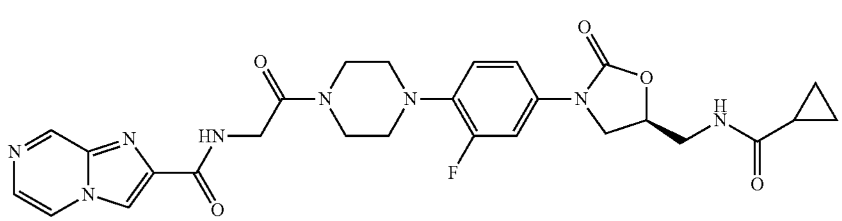 [SMILES: O=C(NCC(=O)N1CCN(c2ccc(N3C[C@H](CNC(=O)C4CC4)OC3=O)cc2F)CC1)c1cn2ccncc2n1] |

TABLE 1-continued

| Compound No. | Structure |
|---|---|
| 71 | 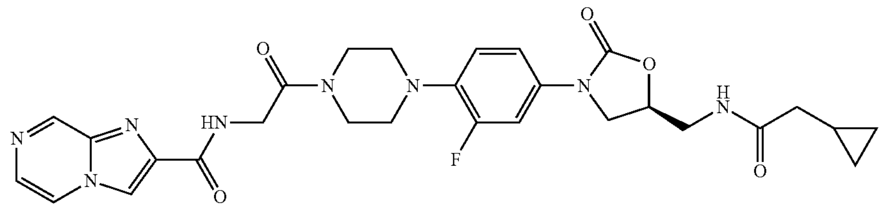 [SMILES: O=C(CC1CC1)NC[C@H]1CN(c2ccc(N3CCN(C(=O)CNC(=O)c4cn5ccncc5n4)CC3)c(F)c2)C(=O)O1] |
| 72 | 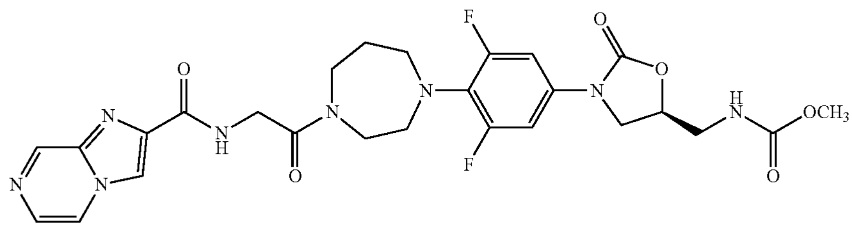 [SMILES: COC(=O)NC[C@H]1CN(c2cc(F)c(N3CCCN(C(=O)CNC(=O)c4cn5ccncc5n4)CC3)c(F)c2)C(=O)O1] |
| 73 | 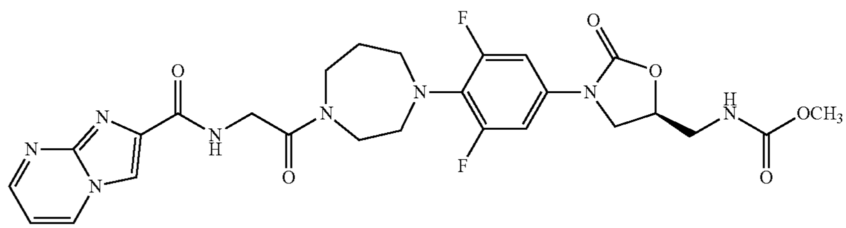 [SMILES: COC(=O)NC[C@H]1CN(c2cc(F)c(N3CCCN(C(=O)CNC(=O)c4cn5cccnc5n4)CC3)c(F)c2)C(=O)O1] |
| 74 | 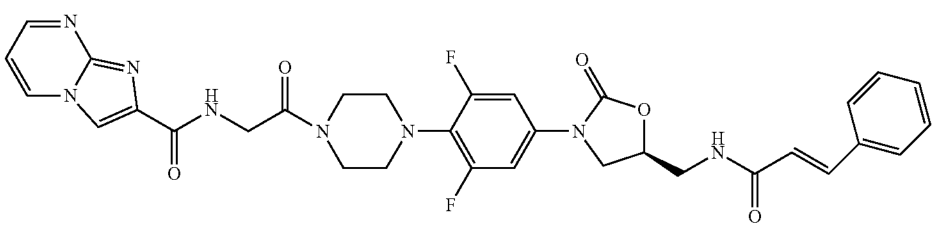 [SMILES: O=C(/C=C/c1ccccc1)NC[C@H]1CN(c2cc(F)c(N3CCN(C(=O)CNC(=O)c4cn5cccnc5n4)CC3)c(F)c2)C(=O)O1] |
| 75 | 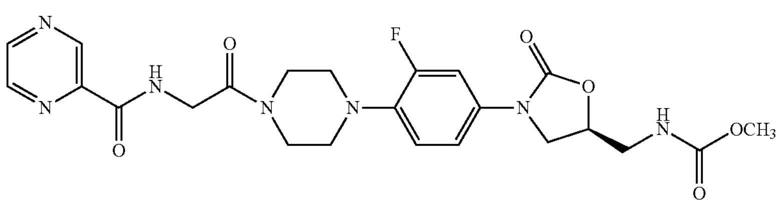 [SMILES: COC(=O)NC[C@H]1CN(c2ccc(N3CCN(C(=O)CNC(=O)c4cnccn4)CC3)c(F)c2)C(=O)O1] |
| 76 | 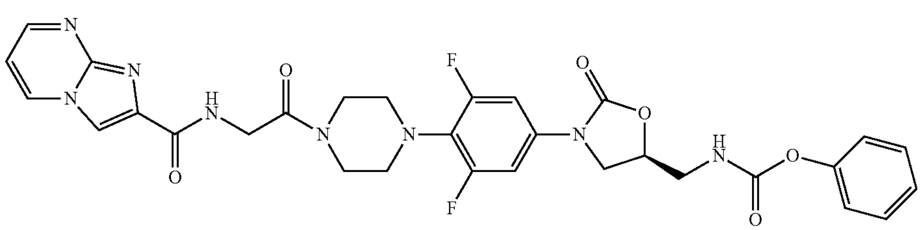 [SMILES: O=C(NC[C@H]1CN(c2cc(F)c(N3CCN(C(=O)CNC(=O)c4cn5cccnc5n4)CC3)c(F)c2)C(=O)O1)Oc1ccccc1] |
| 77 | 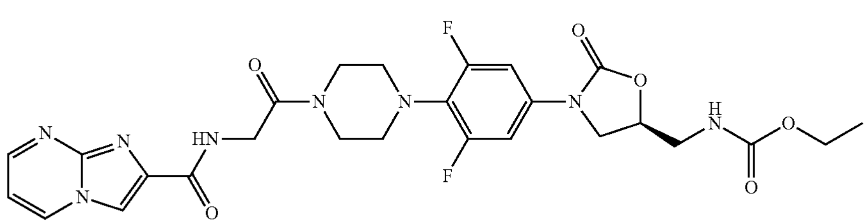 |

TABLE 1-continued

| Compound No. | Structure |
|---|---|
| 78 | 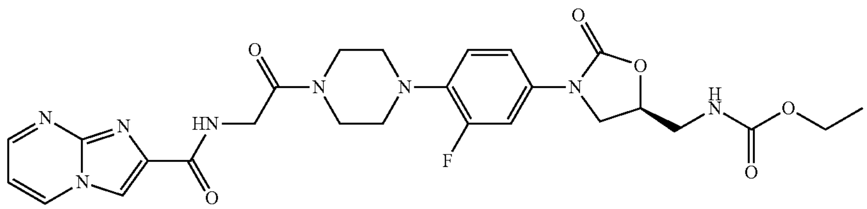 |
| 79 | 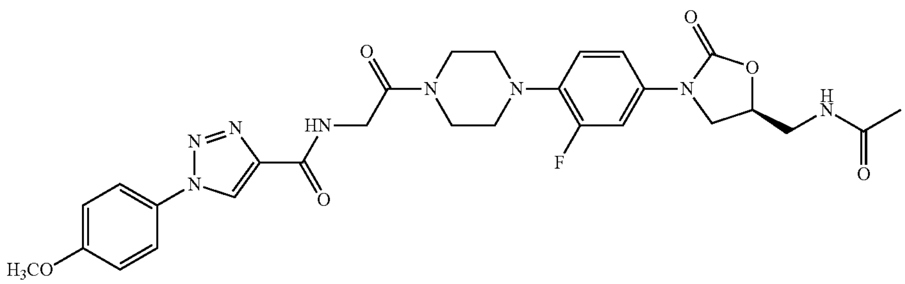 [SMILES: COc1ccc(-n2cc(C(=O)NCC(=O)N3CCN(c4ccc(N5C[C@H](CNC(C)=O)OC5=O)cc4F)CC3)nn2)cc1] |
| 80 | 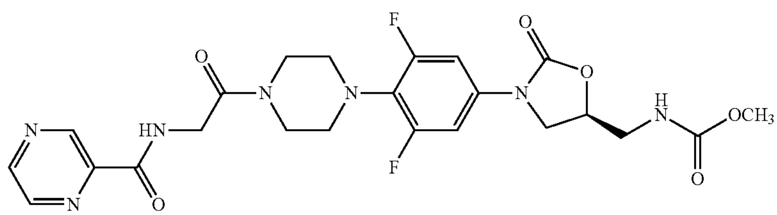 [SMILES: COC(=O)NC[C@H]1CN(c2cc(F)c(N3CCN(C(=O)CNC(=O)c4cnccn4)CC3)c(F)c2)C(=O)O1] |
| 81 | 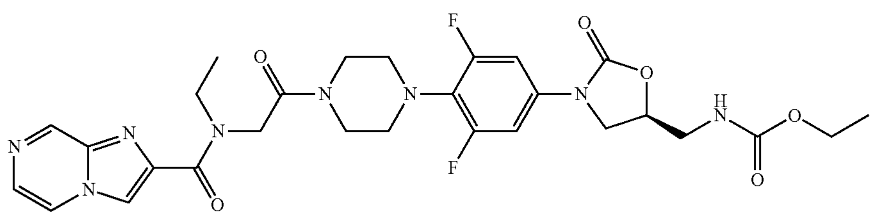 [SMILES: CCOC(=O)NC[C@H]1CN(c2cc(F)c(N3CCN(C(=O)CN(CC)C(=O)c4cn5ccncc5n4)CC3)c(F)c2)C(=O)O1] |
| 82 | 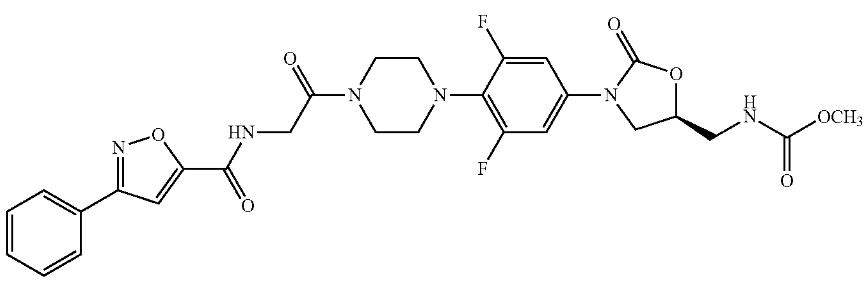 [SMILES: COC(=O)NC[C@H]1CN(c2cc(F)c(N3CCN(C(=O)CNC(=O)c4cc(-c5ccccc5)no4)CC3)c(F)c2)C(=O)O1] |
| 83 | 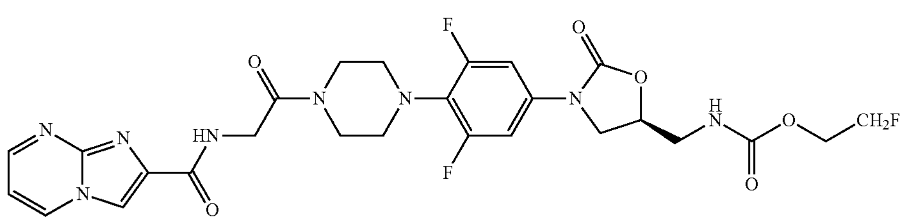 |

TABLE 1-continued

| Compound No. | Structure |
|---|---|
| 84 | 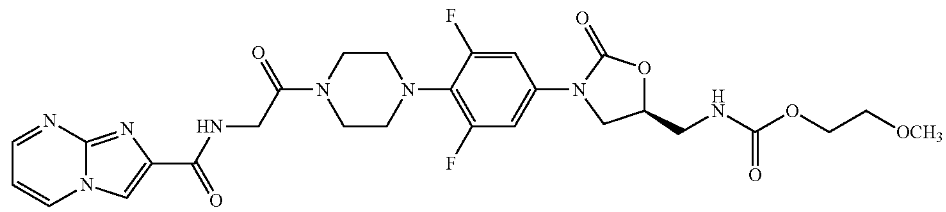 [SMILES: COCCOC(=O)NC[C@H]1CN(c2cc(F)c(N3CCN(C(=O)CNC(=O)c4cn5cccnc5n4)CC3)c(F)c2)C(=O)O1] |
| 85 | 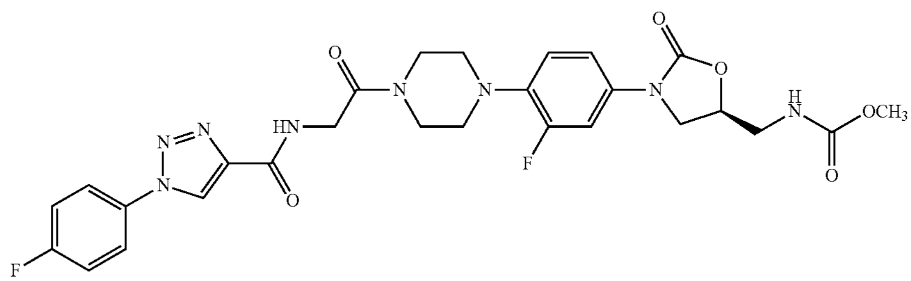 [SMILES: COC(=O)NC[C@H]1CN(c2ccc(N3CCN(C(=O)CNC(=O)c4cn(-c5ccc(F)cc5)nn4)CC3)c(F)c2)C(=O)O1] |
| 86 | 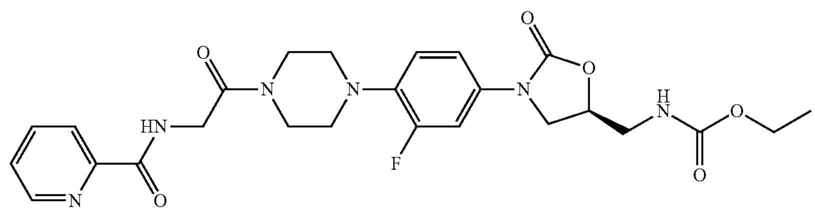 [SMILES: CCOC(=O)NC[C@H]1CN(c2ccc(N3CCN(C(=O)CNC(=O)c4ccccn4)CC3)c(F)c2)C(=O)O1] |
| 87 | 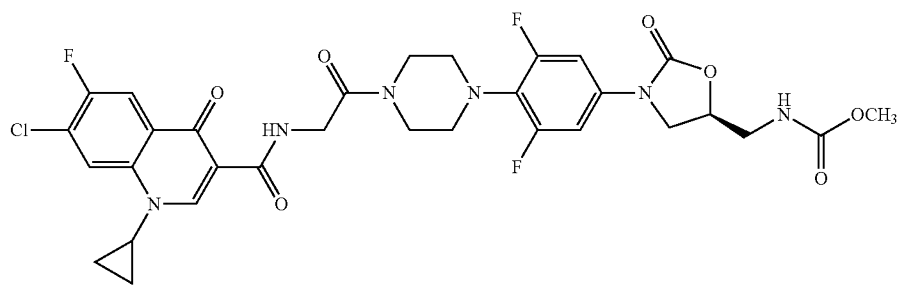 [SMILES: COC(=O)NC[C@H]1CN(c2cc(F)c(N3CCN(C(=O)CNC(=O)c4cn(C5CC5)c5cc(Cl)c(F)cc5c4=O)CC3)c(F)c2)C(=O)O1] |
| 88 | 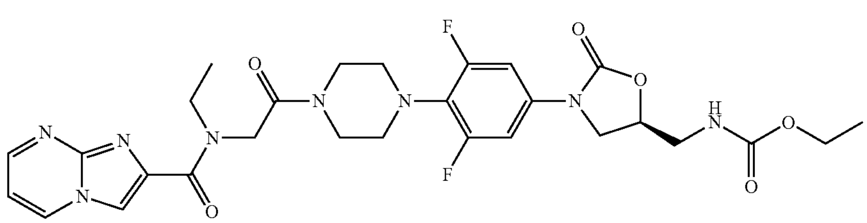 [SMILES: CCOC(=O)NC[C@H]1CN(c2cc(F)c(N3CCN(C(=O)CN(CC)C(=O)c4cn5cccnc5n4)CC3)c(F)c2)C(=O)O1] |
| 89 | 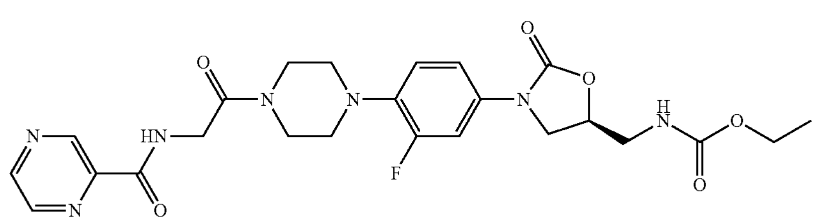 [SMILES: CCOC(=O)NC[C@H]1CN(c2ccc(N3CCN(C(=O)CNC(=O)c4cnccn4)CC3)c(F)c2)C(=O)O1] |

TABLE 1-continued
| Compound No. | Structure |
|---|---|
| 90 | 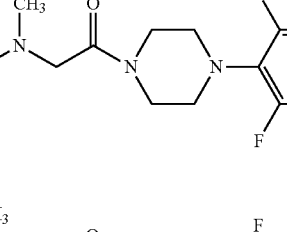 |
| 91 | 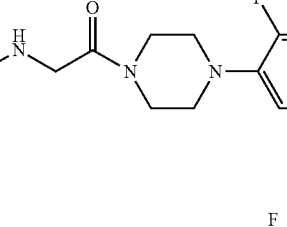 |
| 92 | 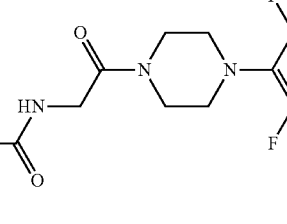 |
| 93 | 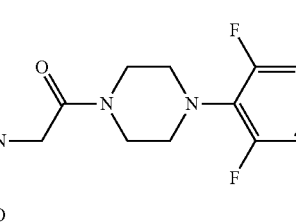 |
| 94 | 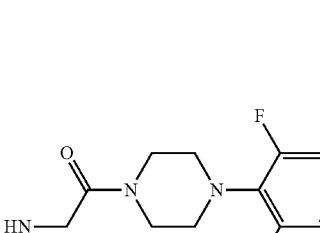 |
| 95 | 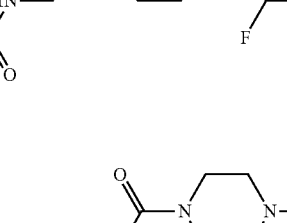 |

TABLE 1-continued

| Compound No. | Structure |
|---|---|
| 96 | 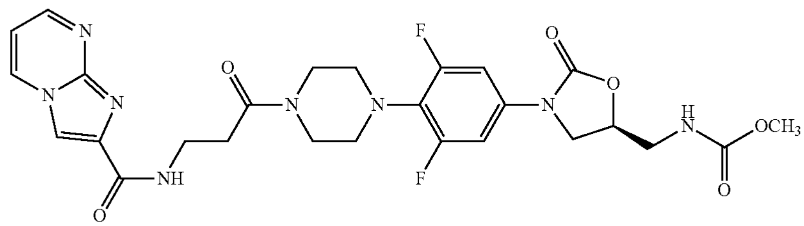 [SMILES: COC(=O)NC[C@H]1CN(c2cc(F)c(N3CCN(C(=O)CCNC(=O)c4cn5cccnc5n4)CC3)c(F)c2)C(=O)O1] |
| 97 | 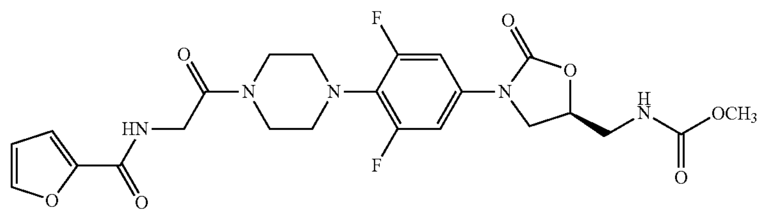 [SMILES: COC(=O)NC[C@H]1CN(c2cc(F)c(N3CCN(C(=O)CNC(=O)c4ccco4)CC3)c(F)c2)C(=O)O1] |
| 98 | 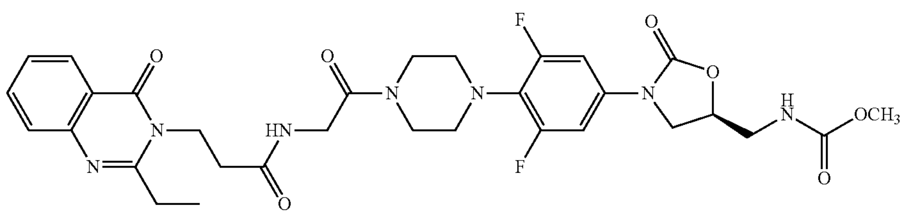 [SMILES: CCc1nc2ccccc2c(=O)n1CCC(=O)NCC(=O)N1CCN(c2c(F)cc(N3C[C@H](CNC(=O)OC)OC3=O)cc2F)CC1] |
| 99 | 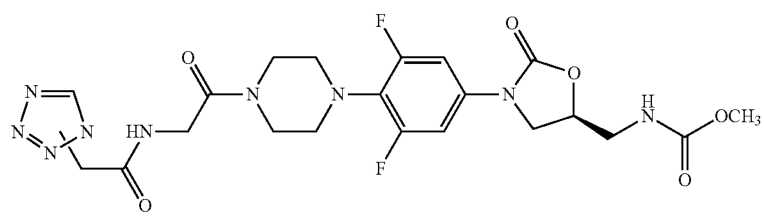 |
| 100 | 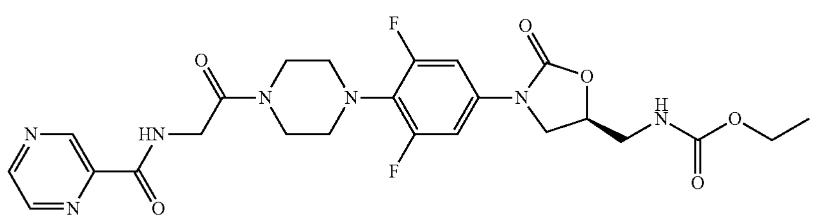 [SMILES: CCOC(=O)NC[C@H]1CN(c2cc(F)c(N3CCN(C(=O)CNC(=O)c4cnccn4)CC3)c(F)c2)C(=O)O1] |
| 101 | 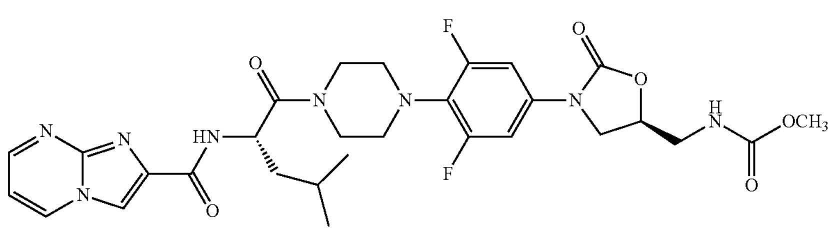 [SMILES: COC(=O)NC[C@H]1CN(c2cc(F)c(N3CCN(C(=O)[C@H](CC(C)C)NC(=O)c4cn5cccnc5n4)CC3)c(F)c2)C(=O)O1] |
| 102 | 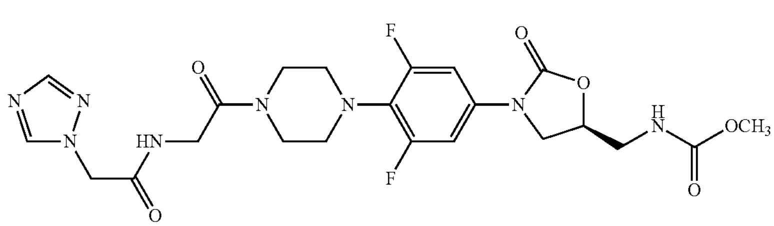 [SMILES: COC(=O)NC[C@H]1CN(c2cc(F)c(N3CCN(C(=O)CNC(=O)Cn4cncn4)CC3)c(F)c2)C(=O)O1] |

TABLE 1-continued

| Compound No. | Structure |
| --- | --- |
| 103 | 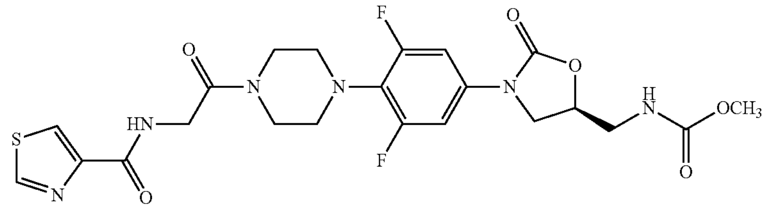 [SMILES: COC(=O)NC[C@H]1CN(c2cc(F)c(N3CCN(C(=O)CNC(=O)c4cscn4)CC3)c(F)c2)C(=O)O1] |
| 104 | 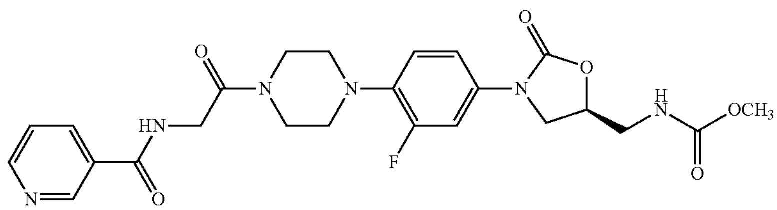 [SMILES: COC(=O)NC[C@H]1CN(c2ccc(N3CCN(C(=O)CNC(=O)c4cccnc4)CC3)c(F)c2)C(=O)O1] |
| 105 | 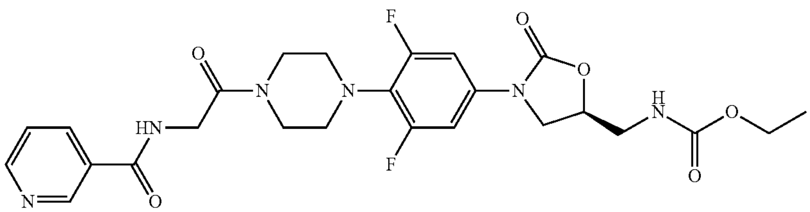 [SMILES: CCOC(=O)NC[C@H]1CN(c2cc(F)c(N3CCN(C(=O)CNC(=O)c4cccnc4)CC3)c(F)c2)C(=O)O1] |
| 106 | 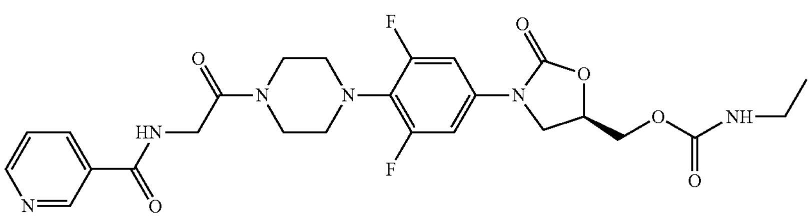 [SMILES: CCNC(=O)OC[C@H]1CN(c2cc(F)c(N3CCN(C(=O)CNC(=O)c4cccnc4)CC3)c(F)c2)C(=O)O1] |
| 107 | 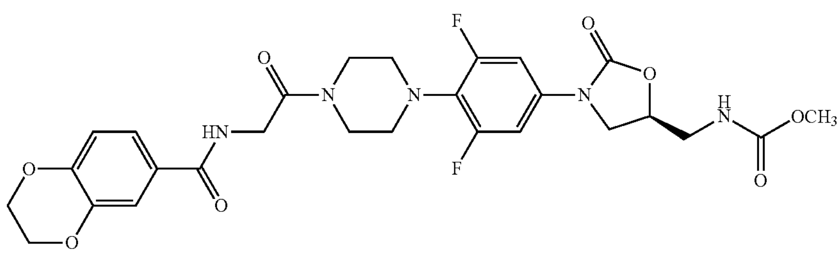 [SMILES: COC(=O)NC[C@H]1CN(c2cc(F)c(N3CCN(C(=O)CNC(=O)c4ccc5c(c4)OCCO5)CC3)c(F)c2)C(=O)O1] |
| 108 | 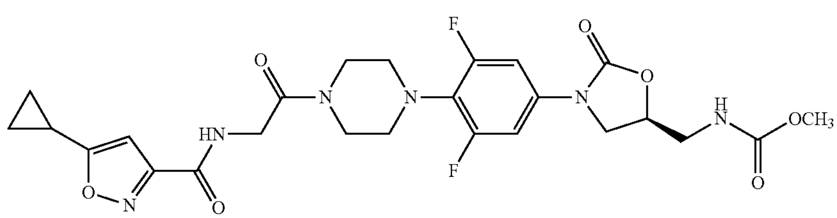 [SMILES: COC(=O)NC[C@H]1CN(c2cc(F)c(N3CCN(C(=O)CNC(=O)c4cc(C5CC5)on4)CC3)c(F)c2)C(=O)O1] |
| 109 | 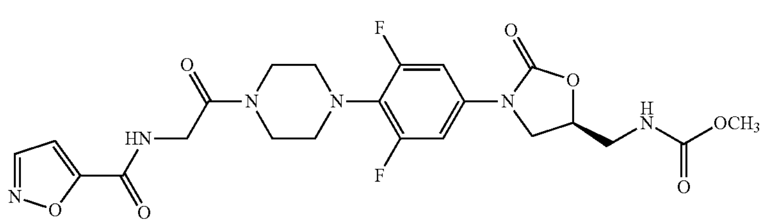 [SMILES: COC(=O)NC[C@H]1CN(c2cc(F)c(N3CCN(C(=O)CNC(=O)c4ccno4)CC3)c(F)c2)C(=O)O1] |

TABLE 1-continued

| Compound No. | Structure |
|---|---|
| 110 | 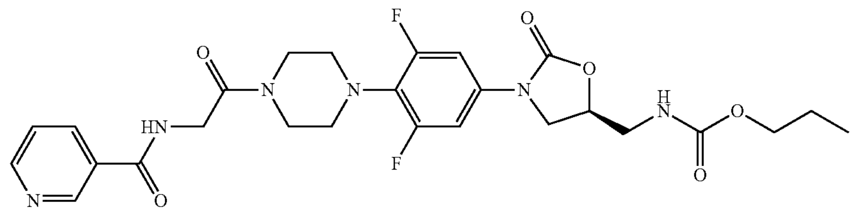 [SMILES: CCCOC(=O)NC[C@H]1CN(c2cc(F)c(N3CCN(C(=O)CNC(=O)c4cccnc4)CC3)c(F)c2)C(=O)O1] |
| 111 | 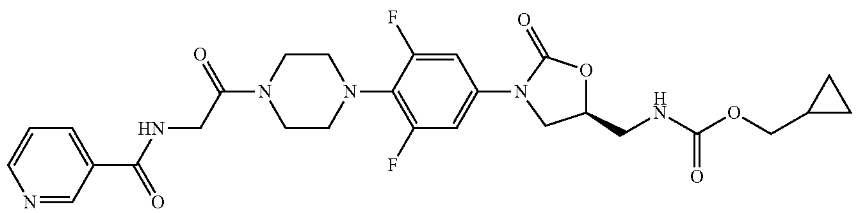 [SMILES: O=C(NC[C@H]1CN(c2cc(F)c(N3CCN(C(=O)CNC(=O)c4cccnc4)CC3)c(F)c2)C(=O)O1)OCC1CC1] |
| 112 | 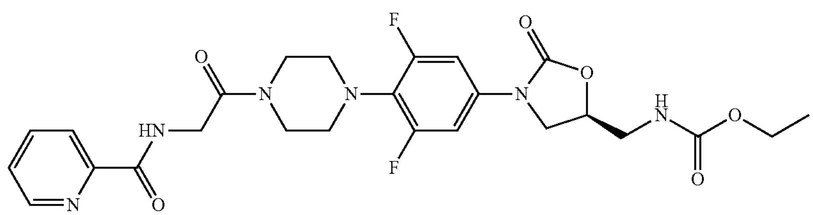 [SMILES: CCOC(=O)NC[C@H]1CN(c2cc(F)c(N3CCN(C(=O)CNC(=O)c4ccccn4)CC3)c(F)c2)C(=O)O1] |
| 113 | 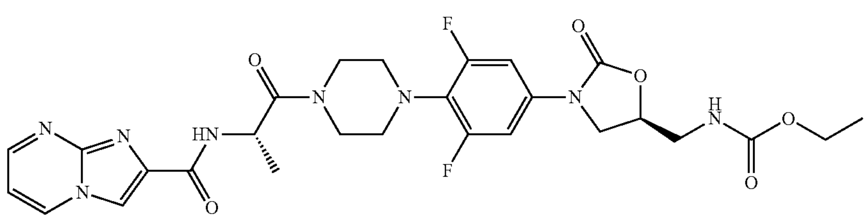 [SMILES: CCOC(=O)NC[C@H]1CN(c2cc(F)c(N3CCN(C(=O)[C@H](C)NC(=O)c4cn5cccnc5n4)CC3)c(F)c2)C(=O)O1] |
| 114 | 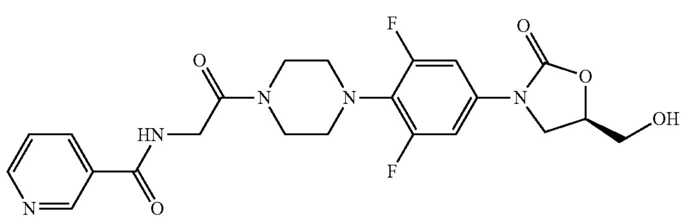 [SMILES: O=C(NCC(=O)N1CCN(c2c(F)cc(N3C[C@H](CO)OC3=O)cc2F)CC1)c1cccnc1] |
| 115 | 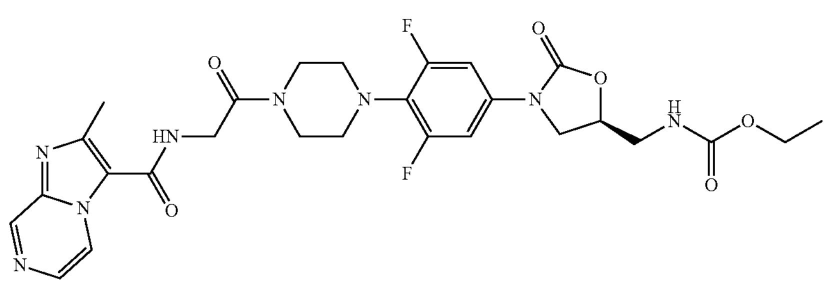 [SMILES: CCOC(=O)NC[C@H]1CN(c2cc(F)c(N3CCN(C(=O)CNC(=O)c4c(C)nc5cnccn45)CC3)c(F)c2)C(=O)O1] |
| 116 | 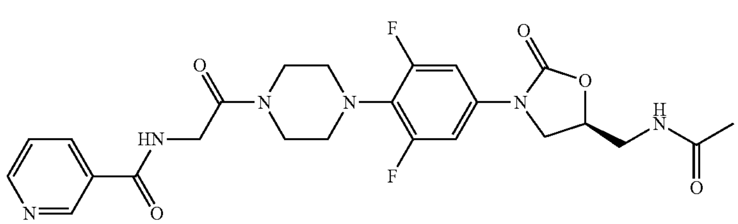 |

TABLE 1-continued

| Compound No. | Structure |
|---|---|
| 117 | (structure) |
| 118 | (structure) |
| 119 | (structure) |
| 120 | (structure) |
| 121 | (structure) |
| 122 | (structure) |
| 123 | (structure) |

TABLE 1-continued

| Compound No. | Structure |
|---|---|
| 124 | 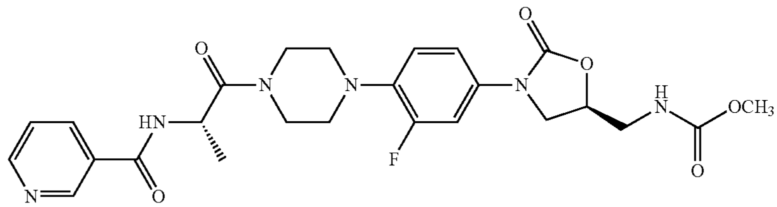 [SMILES: COC(=O)NC[C@H]1CN(c2ccc(N3CCN(C(=O)[C@H](C)NC(=O)c4cccnc4)CC3)c(F)c2)C(=O)O1] |
| 125 | 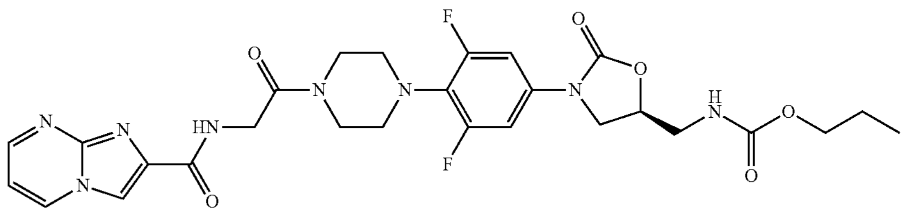 [SMILES: CCCOC(=O)NC[C@H]1CN(c2cc(F)c(N3CCN(C(=O)CNC(=O)c4cn5cccnc5n4)CC3)c(F)c2)C(=O)O1] |
| 126 | 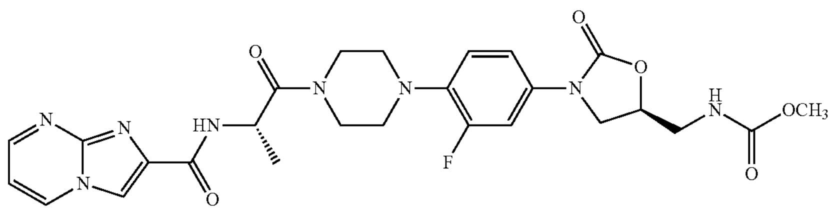 |
| 127 | 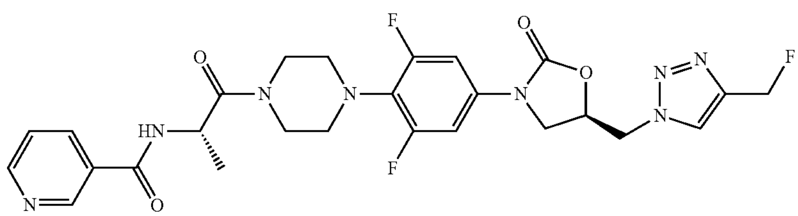 [SMILES: C[C@H](NC(=O)c1cccnc1)C(=O)N1CCN(c2c(F)cc(N3C[C@H](Cn4cc(CF)nn4)OC3=O)cc2F)CC1] |
| 128 | 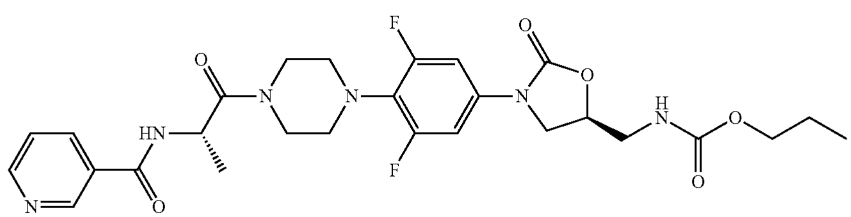 [SMILES: CCCOC(=O)NC[C@H]1CN(c2cc(F)c(N3CCN(C(=O)[C@H](C)NC(=O)c4cccnc4)CC3)c(F)c2)C(=O)O1] |
| 129 | 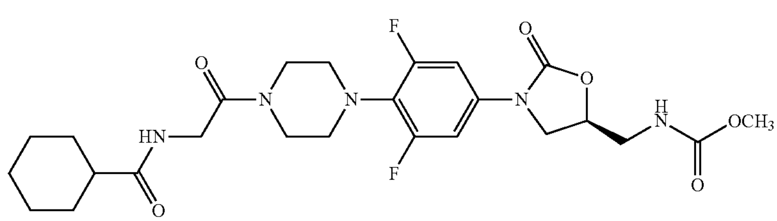 |
| 130 | 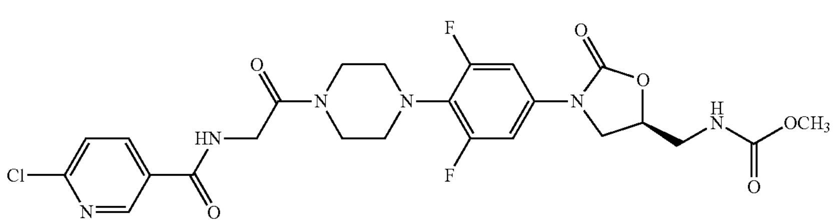 [SMILES: COC(=O)NC[C@H]1CN(c2cc(F)c(N3CCN(C(=O)CNC(=O)c4ccc(Cl)nc4)CC3)c(F)c2)C(=O)O1] |

TABLE 1-continued
| Compound No. | Structure |
|---|---|
| 131 | 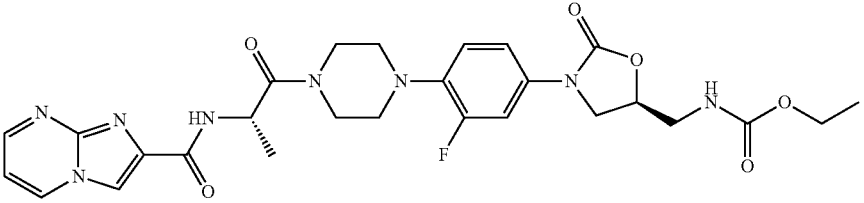 [SMILES: CCOC(=O)NC[C@H]1CN(c2ccc(N3CCN(C(=O)[C@H](C)NC(=O)c4cn5cccnc5n4)CC3)c(F)c2)C(=O)O1] |
| 132 | 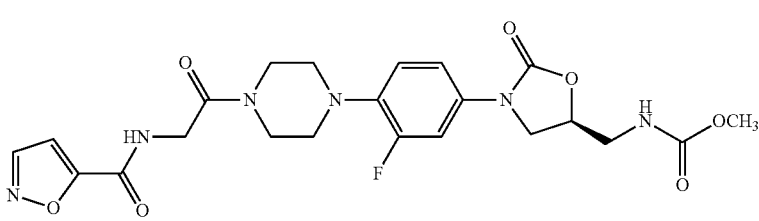 [SMILES: COC(=O)NC[C@H]1CN(c2ccc(N3CCN(C(=O)CNC(=O)c4ccno4)CC3)c(F)c2)C(=O)O1] |
| 133 | 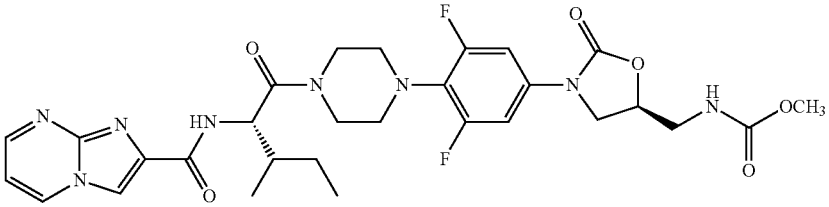 [SMILES: CCC(C)[C@H](NC(=O)c1cn2cccnc2n1)C(=O)N1CCN(c2c(F)cc(N3C[C@H](CNC(=O)OC)OC3=O)cc2F)CC1] |
| 134 | 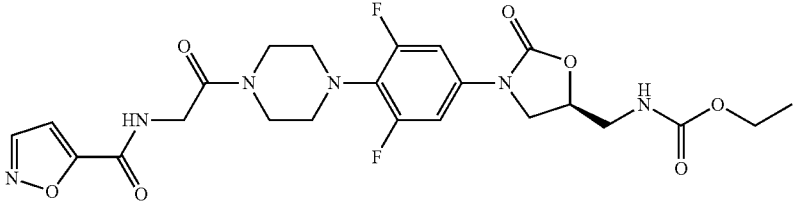 |
| 135 | 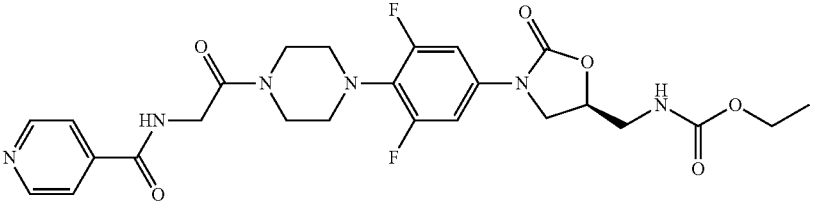 [SMILES: CCOC(=O)NC[C@H]1CN(c2cc(F)c(N3CCN(C(=O)CNC(=O)c4ccncc4)CC3)c(F)c2)C(=O)O1] |
| 136 | 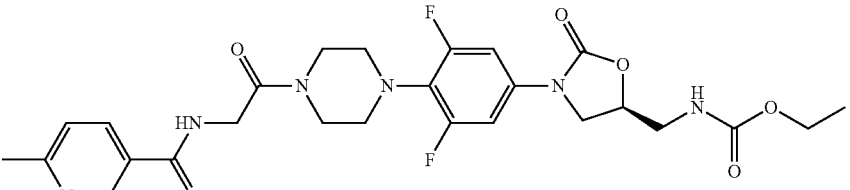 |
| 137 | 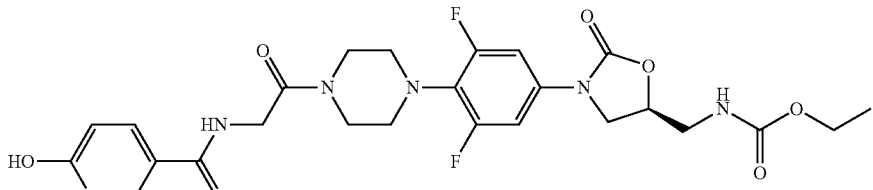 |

TABLE 1-continued

| Compound No. | Structure |
|---|---|
| 138 | 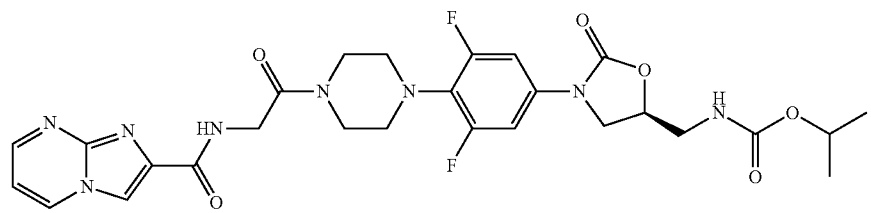 [SMILES: CC(C)OC(=O)NC[C@H]1CN(c2cc(F)c(N3CCN(C(=O)CNC(=O)c4cn5cccnc5n4)CC3)c(F)c2)C(=O)O1] |
| 139 | 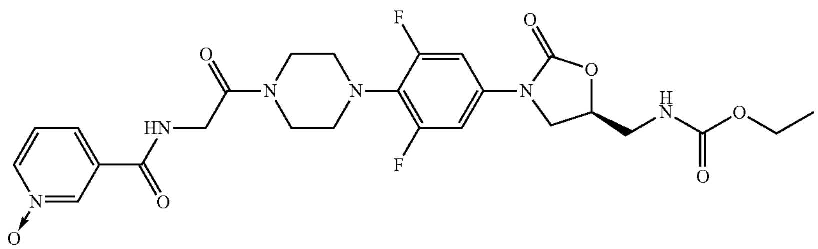 [SMILES: CCOC(=O)NC[C@H]1CN(c2cc(F)c(N3CCN(C(=O)CNC(=O)c4ccc[n+]([O-])c4)CC3)c(F)c2)C(=O)O1] |
| 140 | 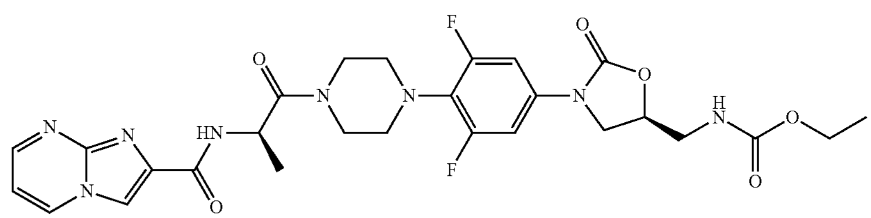 [SMILES: CCOC(=O)NC[C@H]1CN(c2cc(F)c(N3CCN(C(=O)[C@@H](C)NC(=O)c4cn5cccnc5n4)CC3)c(F)c2)C(=O)O1] |
| 141 | 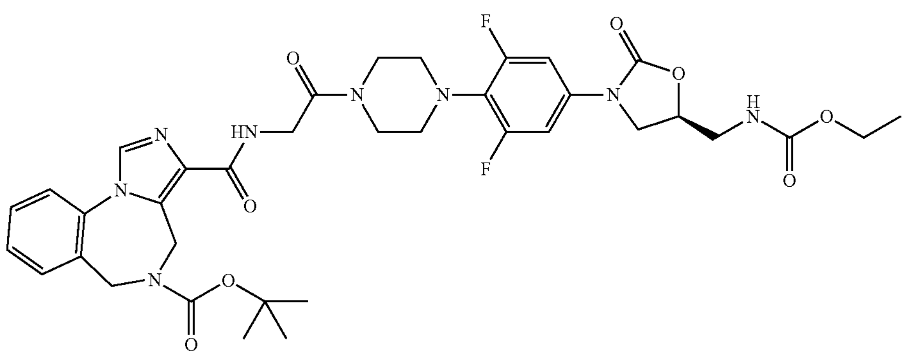 [SMILES: CCOC(=O)NC[C@H]1CN(c2cc(F)c(N3CCN(C(=O)CNC(=O)c4ncn5c4CN(C(=O)OC(C)(C)C)Cc4ccccc4-5)CC3)c(F)c2)C(=O)O1] |
| 142 | 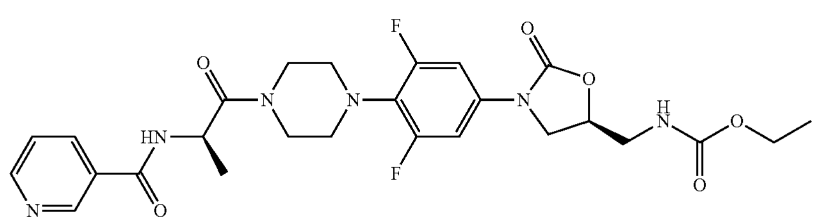 [SMILES: CCOC(=O)NC[C@H]1CN(c2cc(F)c(N3CCN(C(=O)[C@@H](C)NC(=O)c4cccnc4)CC3)c(F)c2)C(=O)O1] |
| 143 | 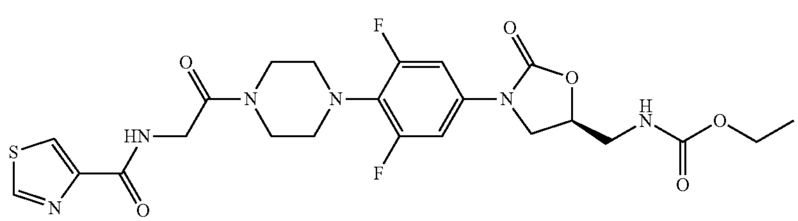 [SMILES: CCOC(=O)NC[C@H]1CN(c2cc(F)c(N3CCN(C(=O)CNC(=O)c4cscn4)CC3)c(F)c2)C(=O)O1] |

TABLE 1-continued

| Compound No. | Structure |
|---|---|
| 144 | 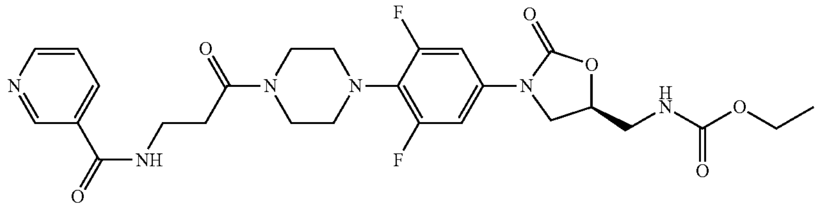 [SMILES: CCOC(=O)NC[C@H]1CN(c2cc(F)c(N3CCN(C(=O)CCNC(=O)c4cccnc4)CC3)c(F)c2)C(=O)O1] |
| 145 | 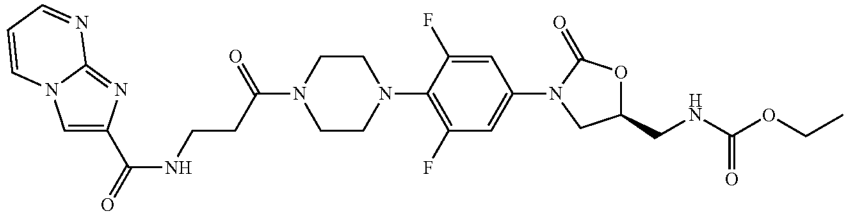 [SMILES: CCOC(=O)NC[C@H]1CN(c2cc(F)c(N3CCN(C(=O)CCNC(=O)c4cn5cccnc5n4)CC3)c(F)c2)C(=O)O1] |
| 146 | 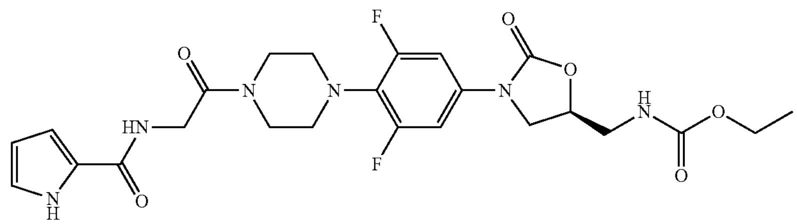 [SMILES: CCOC(=O)NC[C@H]1CN(c2cc(F)c(N3CCN(C(=O)CNC(=O)c4ccc[nH]4)CC3)c(F)c2)C(=O)O1] |
| 147 | 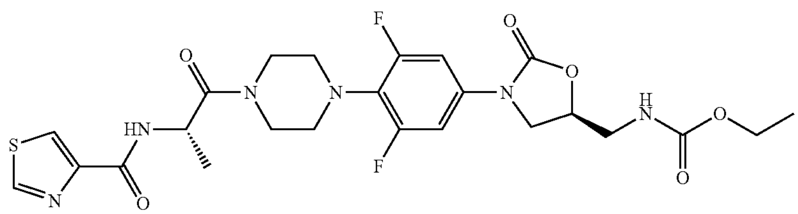 |
| 148 | 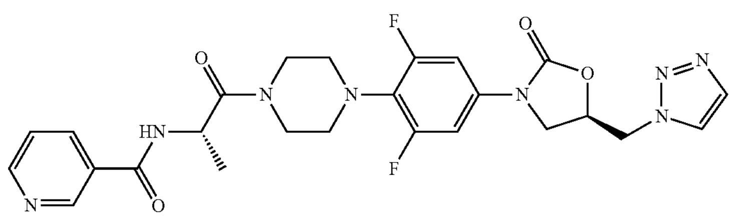 [SMILES: C[C@H](NC(=O)c1cccnc1)C(=O)N1CCN(c2c(F)cc(N3C[C@H](Cn4ccnn4)OC3=O)cc2F)CC1] |
| 149 | 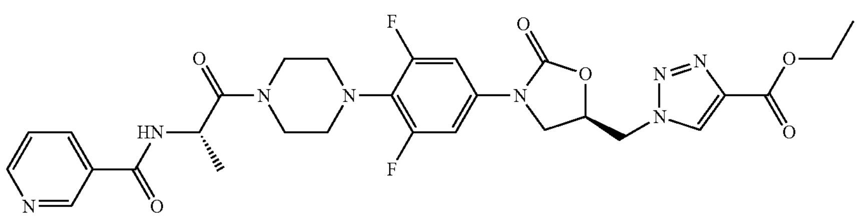 [SMILES: CCOC(=O)c1cn(C[C@H]2CN(c3cc(F)c(N4CCN(C(=O)[C@H](C)NC(=O)c5cccnc5)CC4)c(F)c3)C(=O)O2)nn1] |
| 150 | 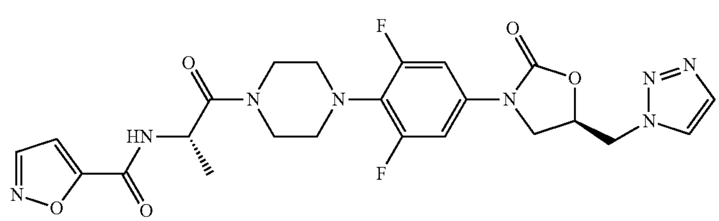 [SMILES: C[C@H](NC(=O)c1ccno1)C(=O)N1CCN(c2c(F)cc(N3C[C@H](Cn4ccnn4)OC3=O)cc2F)CC1] |

TABLE 1-continued

| Compound No. | Structure |
|---|---|
| 151 | 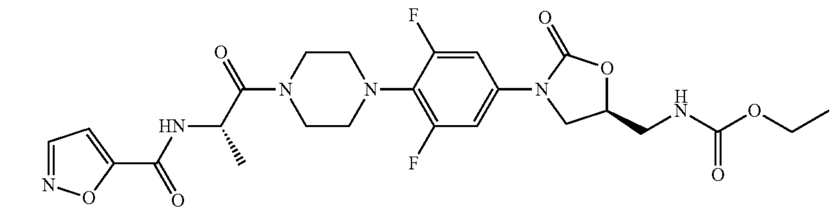 |
| 152 | 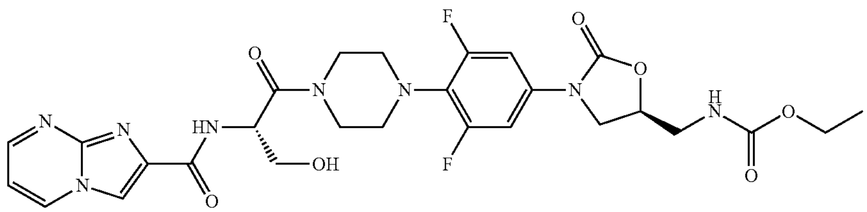 [SMILES: CCOC(=O)NC[C@H]1CN(c2cc(F)c(N3CCN(C(=O)[C@H](CO)NC(=O)c4cn5cccnc5n4)CC3)c(F)c2)C(=O)O1] |
| 153 | 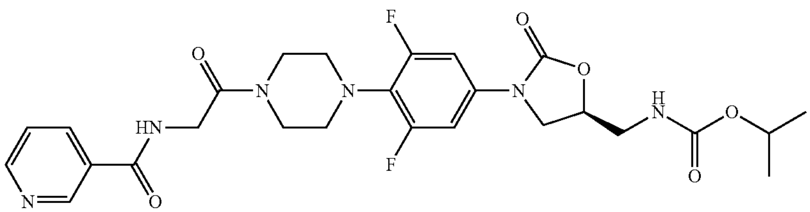 [SMILES: CC(C)OC(=O)NC[C@H]1CN(c2cc(F)c(N3CCN(C(=O)CNC(=O)c4cccnc4)CC3)c(F)c2)C(=O)O1] |
| 154 | 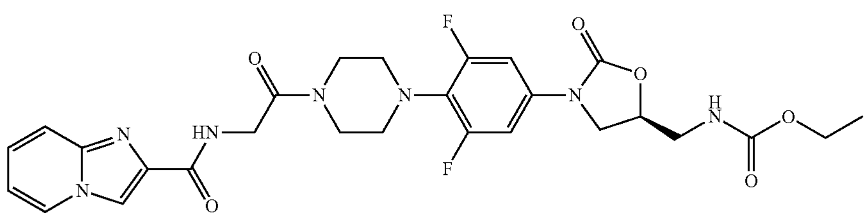 [SMILES: CCOC(=O)NC[C@H]1CN(c2cc(F)c(N3CCN(C(=O)CNC(=O)c4cn5ccccc5n4)CC3)c(F)c2)C(=O)O1] |
| 155 | 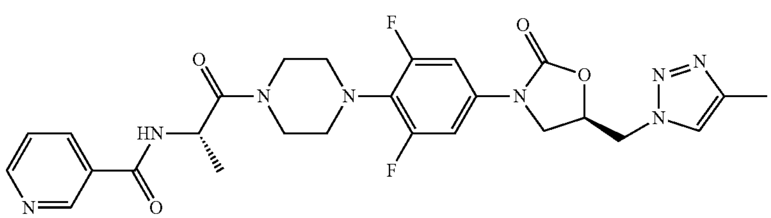 [SMILES: Cc1cn(C[C@H]2CN(c3cc(F)c(N4CCN(C(=O)[C@H](C)NC(=O)c5cccnc5)CC4)c(F)c3)C(=O)O2)nn1] |
| 156 | 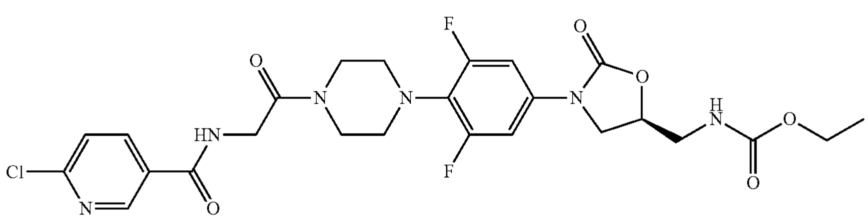 [SMILES: CCOC(=O)NC[C@H]1CN(c2cc(F)c(N3CCN(C(=O)CNC(=O)c4ccc(Cl)nc4)CC3)c(F)c2)C(=O)O1] |
| 157 | 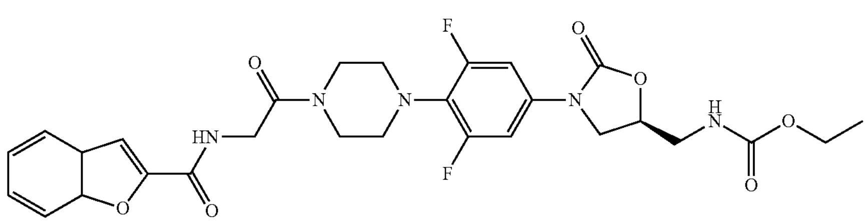 [SMILES: CCOC(=O)NC[C@H]1CN(c2cc(F)c(N3CCN(C(=O)CNC(=O)C4=CC5C=CC=CC5O4)CC3)c(F)c2)C(=O)O1] |

TABLE 1-continued

| Compound No. | Structure |
|---|---|
| 158 | 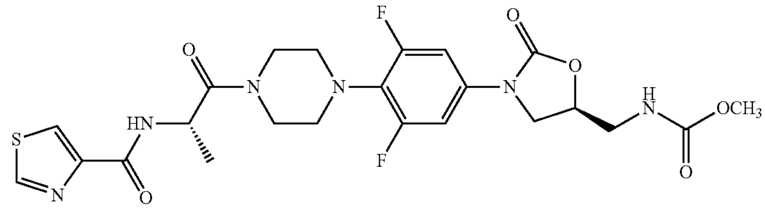 [SMILES: COC(=O)NC[C@H]1CN(c2cc(F)c(N3CCN(C(=O)[C@H](C)NC(=O)c4cscn4)CC3)c(F)c2)C(=O)O1] |
| 159 | 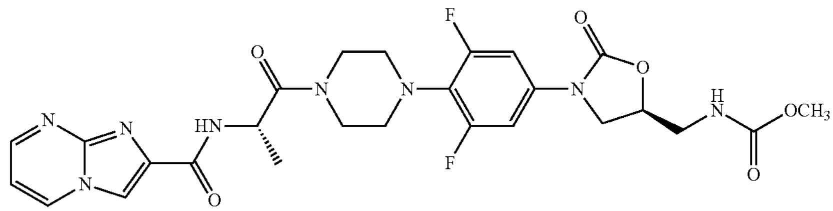 [SMILES: COC(=O)NC[C@H]1CN(c2cc(F)c(N3CCN(C(=O)[C@H](C)NC(=O)c4cn5cccnc5n4)CC3)c(F)c2)C(=O)O1] |
| 160 | 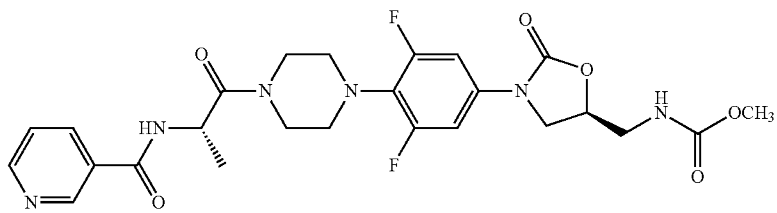 |
| 161 | 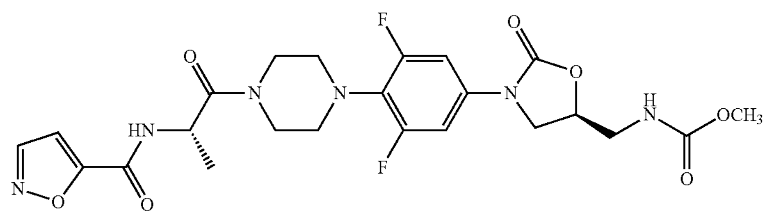 [SMILES: COC(=O)NC[C@H]1CN(c2cc(F)c(N3CCN(C(=O)[C@H](C)NC(=O)c4ccno4)CC3)c(F)c2)C(=O)O1] |
| 162 | 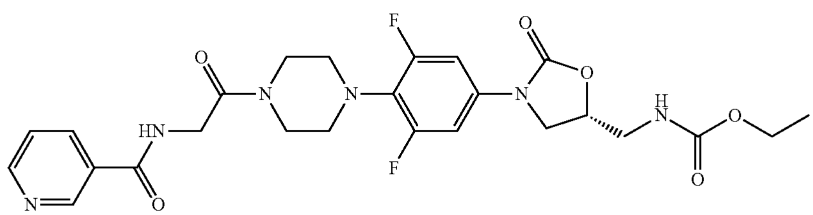 [SMILES: CCOC(=O)NC[C@@H]1CN(c2cc(F)c(N3CCN(C(=O)CNC(=O)c4cccnc4)CC3)c(F)c2)C(=O)O1] |
| 163 | 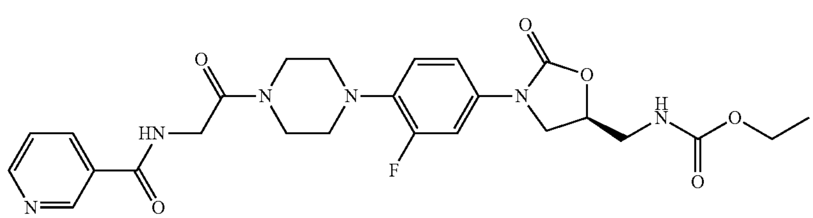 |
| 164 | 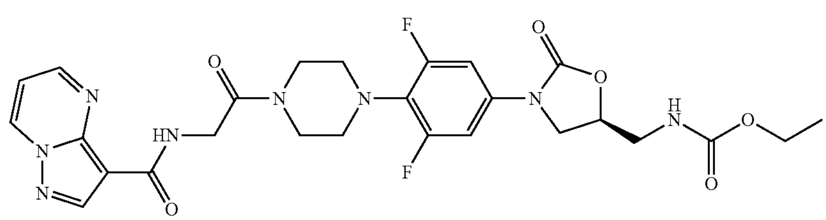 [SMILES: CCOC(=O)NC[C@H]1CN(c2cc(F)c(N3CCN(C(=O)CNC(=O)c4cnn5cccnc45)CC3)c(F)c2)C(=O)O1] |

TABLE 1-continued

| Compound No. | Structure |
|---|---|
| 165 | 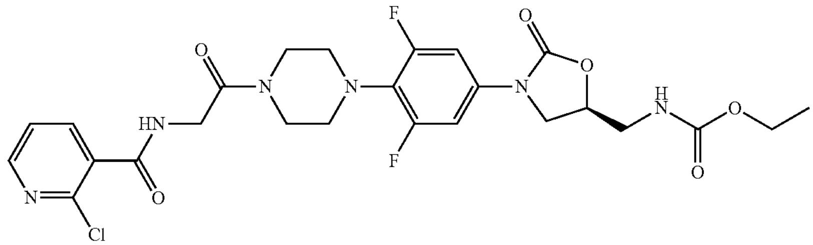 [SMILES: CCOC(=O)NC[C@H]1CN(c2cc(F)c(N3CCN(C(=O)CNC(=O)c4cccnc4Cl)CC3)c(F)c2)C(=O)O1] |
| 166 | 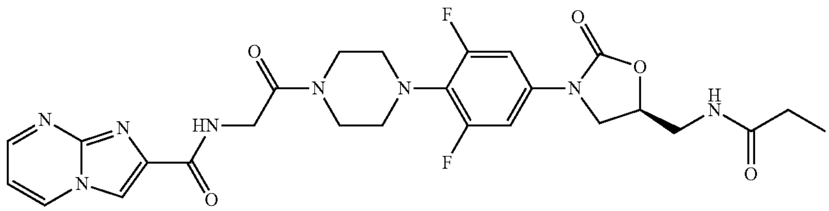 [SMILES: CCC(=O)NC[C@H]1CN(c2cc(F)c(N3CCN(C(=O)CNC(=O)c4cn5cccnc5n4)CC3)c(F)c2)C(=O)O1] |
| 167 | 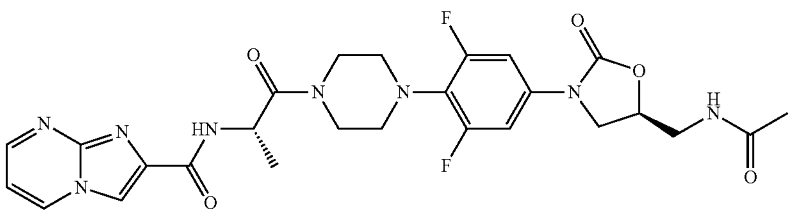 [SMILES: CC(=O)NC[C@H]1CN(c2cc(F)c(N3CCN(C(=O)[C@H](C)NC(=O)c4cn5cccnc5n4)CC3)c(F)c2)C(=O)O1] |
| 168 | 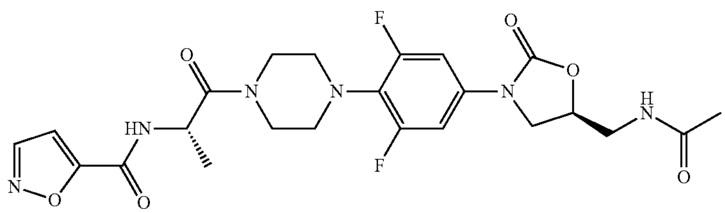 [SMILES: CC(=O)NC[C@H]1CN(c2cc(F)c(N3CCN(C(=O)[C@H](C)NC(=O)c4ccno4)CC3)c(F)c2)C(=O)O1] |
| 169 | 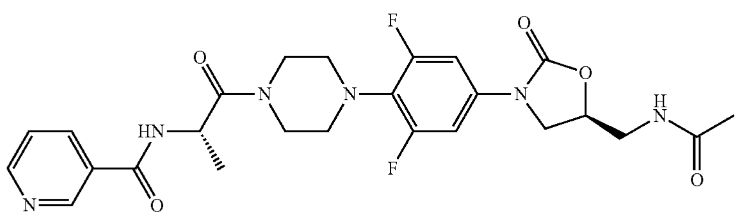 [SMILES: CC(=O)NC[C@H]1CN(c2cc(F)c(N3CCN(C(=O)[C@H](C)NC(=O)c4cccnc4)CC3)c(F)c2)C(=O)O1] |
| 170 | 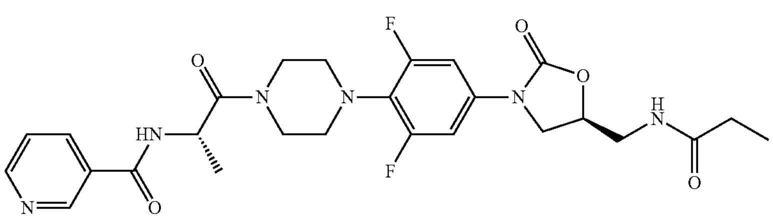 [SMILES: CCC(=O)NC[C@H]1CN(c2cc(F)c(N3CCN(C(=O)[C@H](C)NC(=O)c4cccnc4)CC3)c(F)c2)C(=O)O1] |
| 171 | 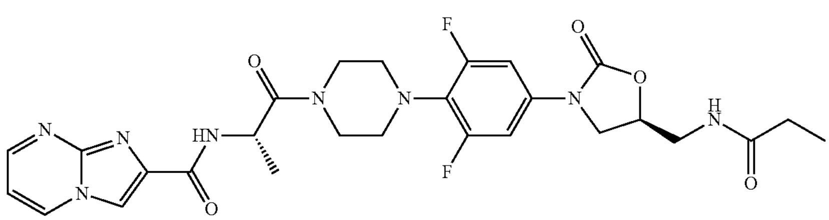 [SMILES: CCC(=O)NC[C@H]1CN(c2cc(F)c(N3CCN(C(=O)[C@H](C)NC(=O)c4cn5cccnc5n4)CC3)c(F)c2)C(=O)O1] |

TABLE 1-continued

| Compound No. | Structure |
|---|---|
| 172 | 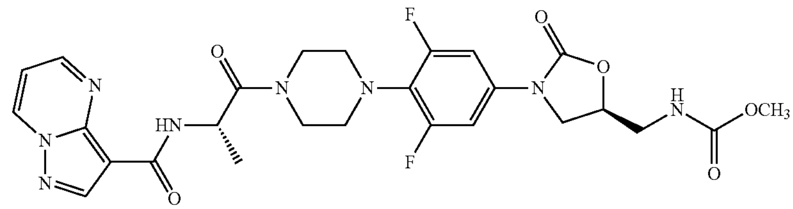 [SMILES: COC(=O)NC[C@H]1CN(c2cc(F)c(N3CCN(C(=O)[C@H](C)NC(=O)c4cnn5cccnc45)CC3)c(F)c2)C(=O)O1] |
| 173 | 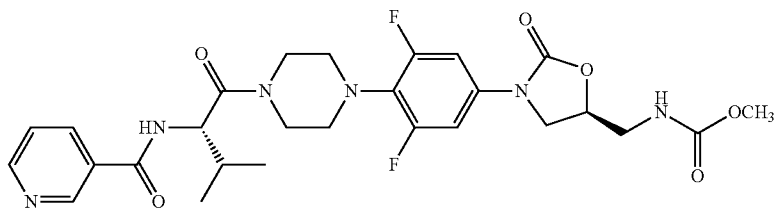 [SMILES: COC(=O)NC[C@H]1CN(c2cc(F)c(N3CCN(C(=O)[C@@H](NC(=O)c4cccnc4)C(C)C)CC3)c(F)c2)C(=O)O1] |
| 174 | 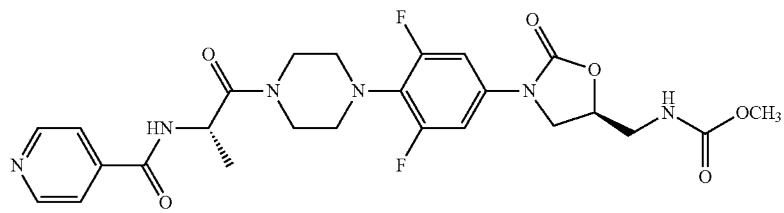 [SMILES: COC(=O)NC[C@H]1CN(c2cc(F)c(N3CCN(C(=O)[C@H](C)NC(=O)c4ccncc4)CC3)c(F)c2)C(=O)O1] |
| 175 | 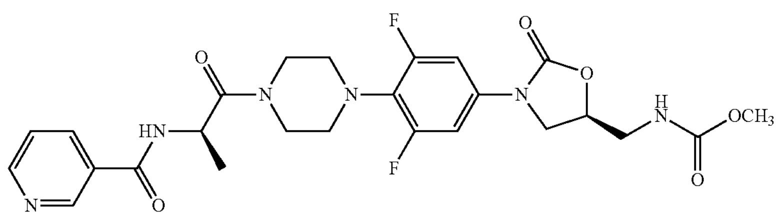 [SMILES: COC(=O)NC[C@H]1CN(c2cc(F)c(N3CCN(C(=O)[C@@H](C)NC(=O)c4cccnc4)CC3)c(F)c2)C(=O)O1] |
| 176 | 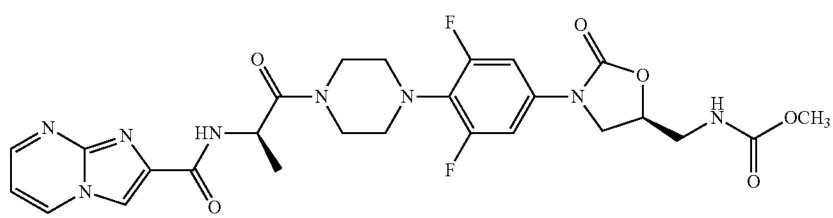 [SMILES: COC(=O)NC[C@H]1CN(c2cc(F)c(N3CCN(C(=O)[C@@H](C)NC(=O)c4cn5cccnc5n4)CC3)c(F)c2)C(=O)O1] |
| 177 | 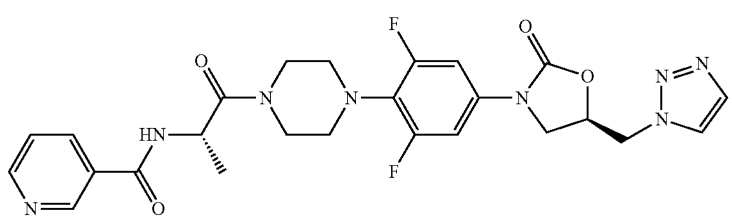 [SMILES: C[C@H](NC(=O)c1cccnc1)C(=O)N1CCN(c2c(F)cc(N3C[C@H](Cn4ccnn4)OC3=O)cc2F)CC1] |
| 178 | 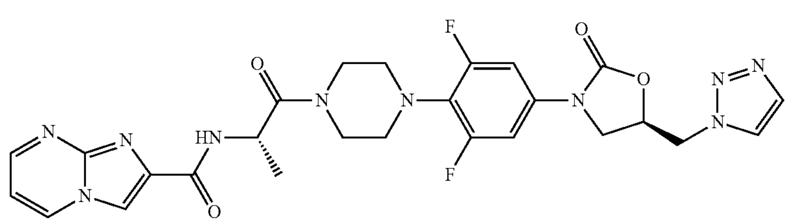 [SMILES: C[C@H](NC(=O)c1cn2cccnc2n1)C(=O)N1CCN(c2c(F)cc(N3C[C@H](Cn4ccnn4)OC3=O)cc2F)CC1] |

TABLE 1-continued

| Compound No. | Structure |
|---|---|
| 179 | 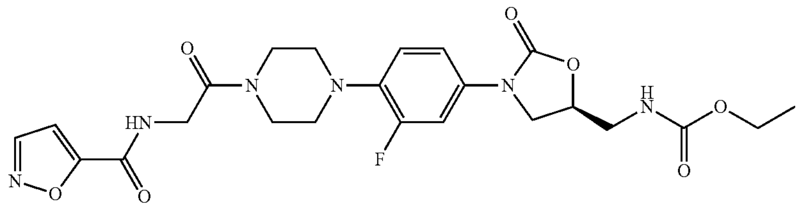 [SMILES: CCOC(=O)NC[C@H]1CN(c2ccc(N3CCN(C(=O)CNC(=O)c4ccno4)CC3)c(F)c2)C(=O)O1] |
| 180 | 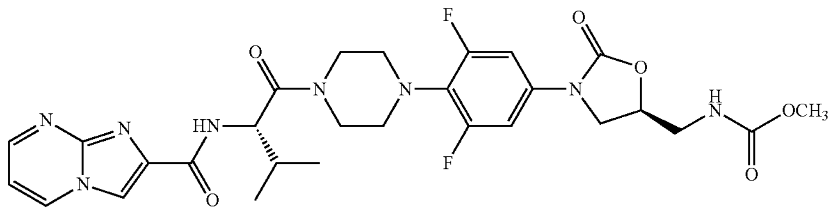 [SMILES: COC(=O)NC[C@H]1CN(c2cc(F)c(N3CCN(C(=O)[C@@H](NC(=O)c4cn5cccnc5n4)C(C)C)CC3)c(F)c2)C(=O)O1] |
| 181 | 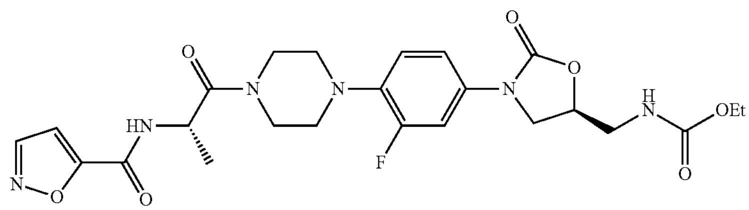 [SMILES: CCOC(=O)NC[C@H]1CN(c2ccc(N3CCN(C(=O)[C@H](C)NC(=O)c4ccno4)CC3)c(F)c2)C(=O)O1] |
| 182 | 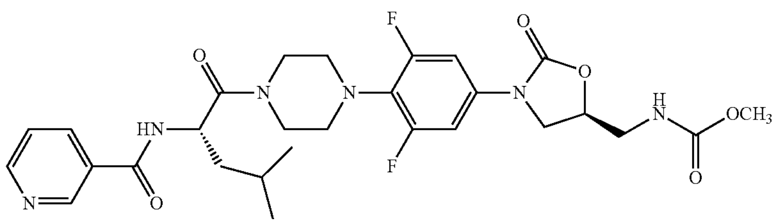 [SMILES: COC(=O)NC[C@H]1CN(c2cc(F)c(N3CCN(C(=O)[C@H](CC(C)C)NC(=O)c4cccnc4)CC3)c(F)c2)C(=O)O1] |
| 183 | 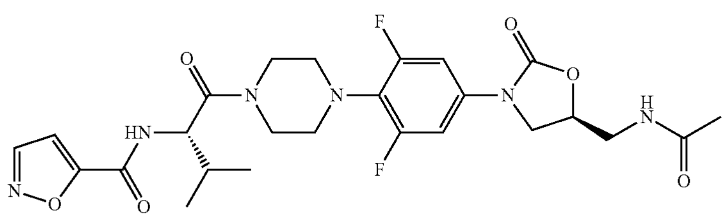 [SMILES: CC(=O)NC[C@H]1CN(c2cc(F)c(N3CCN(C(=O)[C@@H](NC(=O)c4ccno4)C(C)C)CC3)c(F)c2)C(=O)O1] |
| 184 | 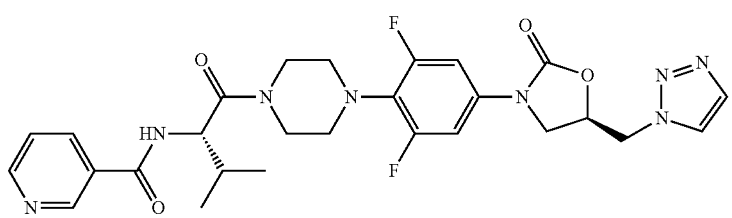 [SMILES: CC(C)[C@H](NC(=O)c1cccnc1)C(=O)N1CCN(c2c(F)cc(N3C[C@H](Cn4ccnn4)OC3=O)cc2F)CC1] |
| 185 | 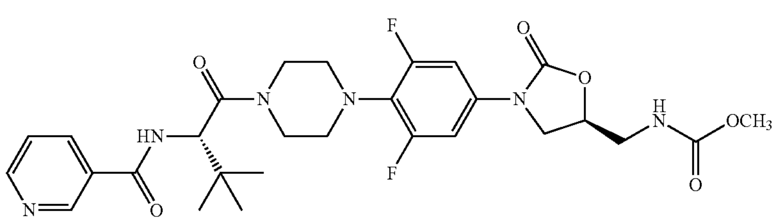 [SMILES: COC(=O)NC[C@H]1CN(c2cc(F)c(N3CCN(C(=O)[C@@H](NC(=O)c4cccnc4)C(C)(C)C)CC3)c(F)c2)C(=O)O1] |

TABLE 1-continued

| Compound No. | Structure |
|---|---|
| 186 | 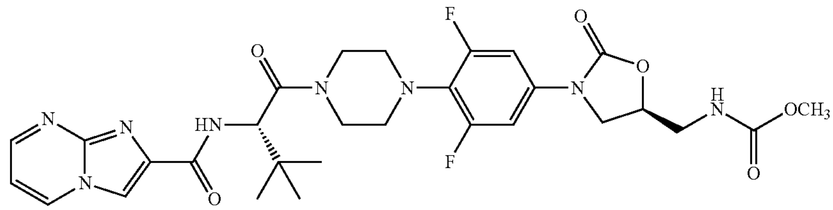 [SMILES: COC(=O)NC[C@H]1CN(c2cc(F)c(N3CCN(C(=O)[C@@H](NC(=O)c4cn5cccnc5n4)C(C)(C)C)CC3)c(F)c2)C(=O)O1] |
| 187 | 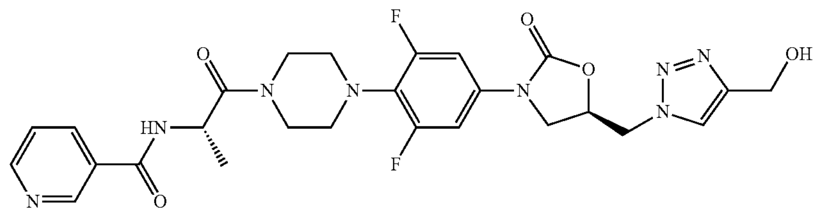 [SMILES: C[C@H](NC(=O)c1cccnc1)C(=O)N1CCN(c2c(F)cc(N3C[C@H](Cn4cc(CO)nn4)OC3=O)cc2F)CC1] |
| 188 | 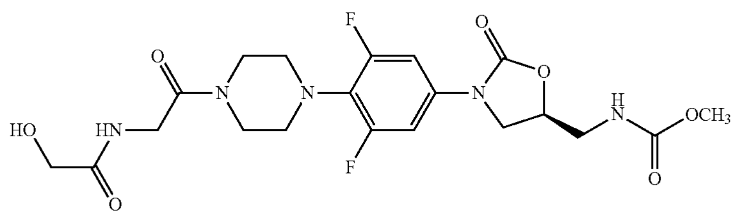 [SMILES: COC(=O)NC[C@H]1CN(c2cc(F)c(N3CCN(C(=O)CNC(=O)CO)CC3)c(F)c2)C(=O)O1] |
| 189 | 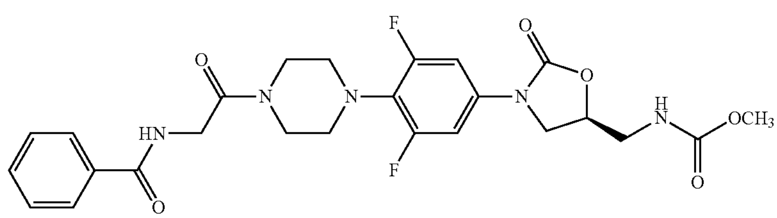 |
| 190 | 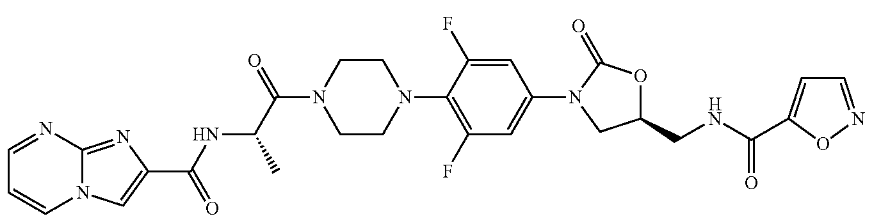 [SMILES: C[C@H](NC(=O)c1cn2cccnc2n1)C(=O)N1CCN(c2c(F)cc(N3C[C@H](CNC(=O)c4ccno4)OC3=O)cc2F)CC1] |
| 191 | 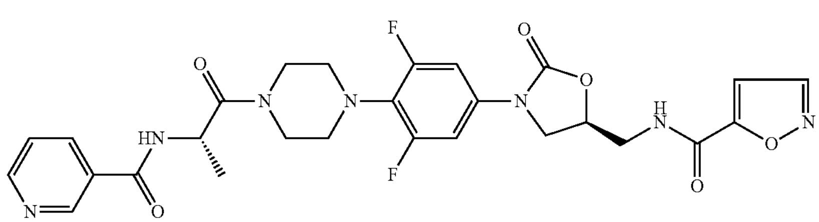 [SMILES: C[C@H](NC(=O)c1cccnc1)C(=O)N1CCN(c2c(F)cc(N3C[C@H](CNC(=O)c4ccno4)OC3=O)cc2F)CC1] |
| 192 | 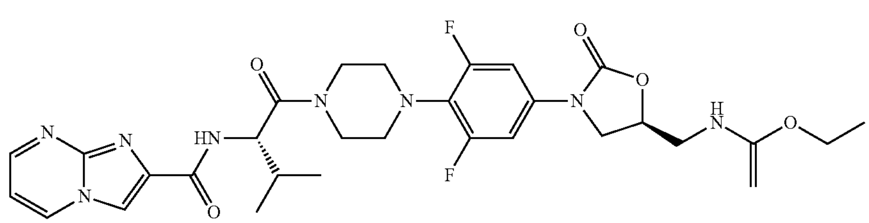 [SMILES: C=C(NC[C@H]1CN(c2cc(F)c(N3CCN(C(=O)[C@@H](NC(=O)c4cn5cccnc5n4)C(C)C)CC3)c(F)c2)C(=O)O1)OCC] |

TABLE 1-continued
| Compound No. | Structure |
|---|---|
| 193 | 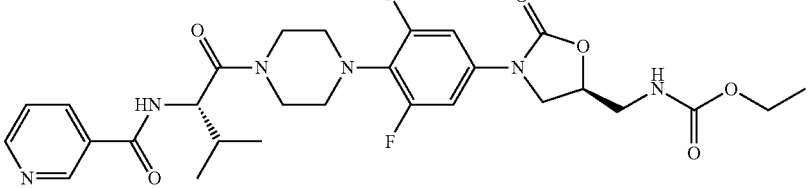 |
| 194 | 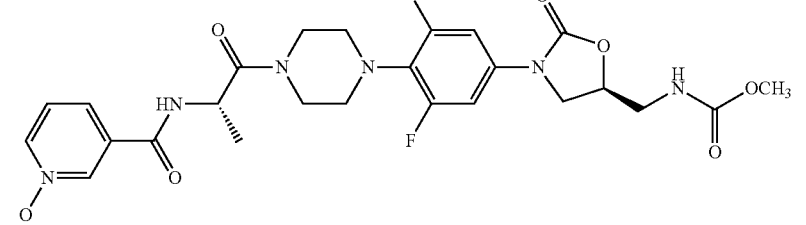 |
| 195 | 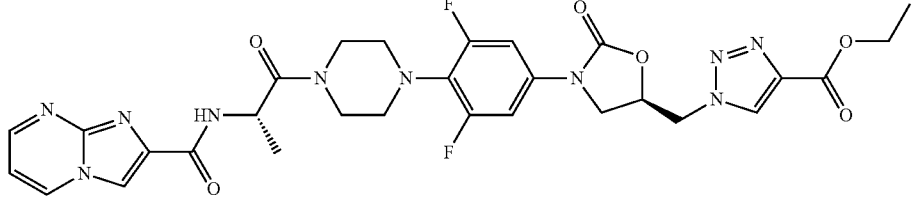 [SMILES: CCOC(=O)c1cn(C[C@H]2CN(c3cc(F)c(N4CCN(C(=O)[C@H](C)NC(=O)c5cn6cccnc6n5)CC4)c(F)c3)C(=O)O2)nn1] |
| 196 | 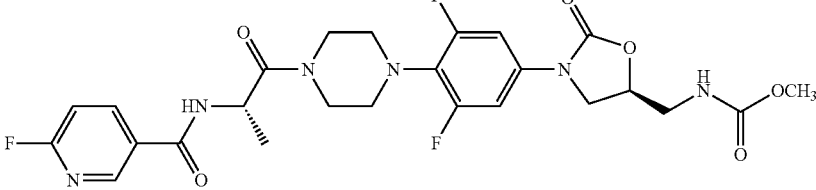 |
| 197 | 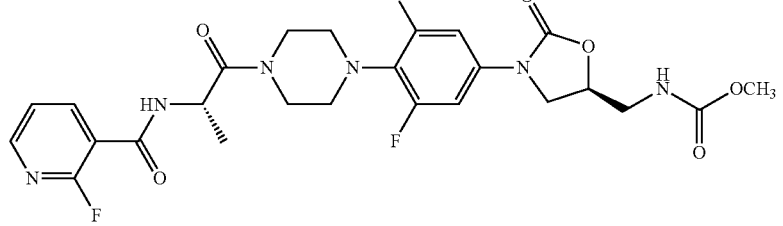 |
| 198 | 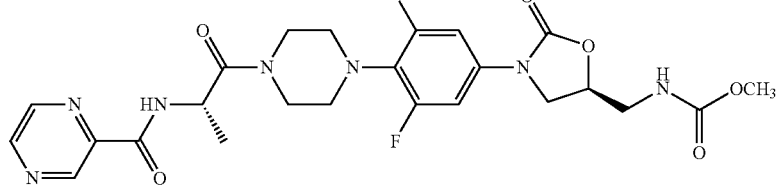 |
| 199 | 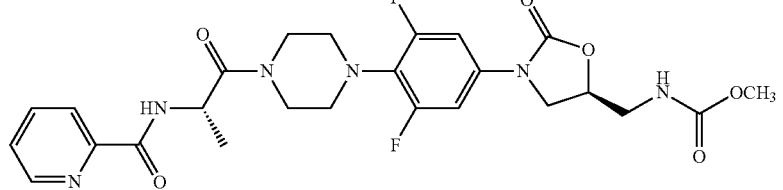 |

TABLE 1-continued

| Compound No. | Structure |
|---|---|
| 200 | 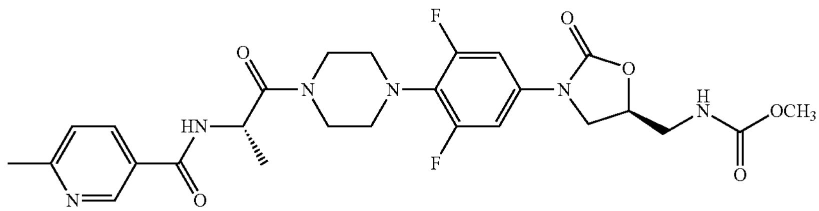 [SMILES: COC(=O)NC[C@H]1CN(c2cc(F)c(N3CCN(C(=O)[C@H](C)NC(=O)c4ccc(C)nc4)CC3)c(F)c2)C(=O)O1] |
| 201 | 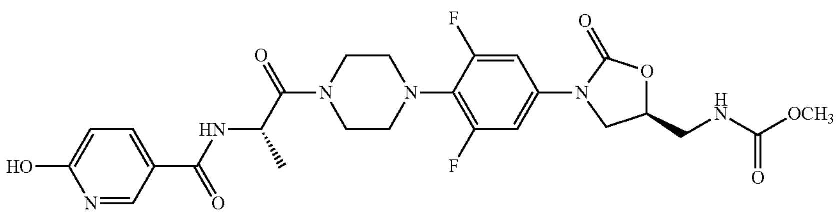 [SMILES: COC(=O)NC[C@H]1CN(c2cc(F)c(N3CCN(C(=O)[C@H](C)NC(=O)c4ccc(O)nc4)CC3)c(F)c2)C(=O)O1] |
| 202 | 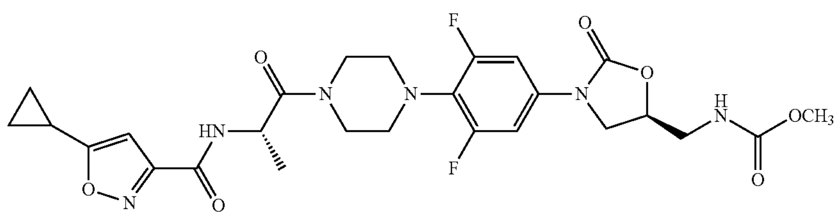 [SMILES: COC(=O)NC[C@H]1CN(c2cc(F)c(N3CCN(C(=O)[C@H](C)NC(=O)c4cc(C5CC5)on4)CC3)c(F)c2)C(=O)O1] |
| 203 | 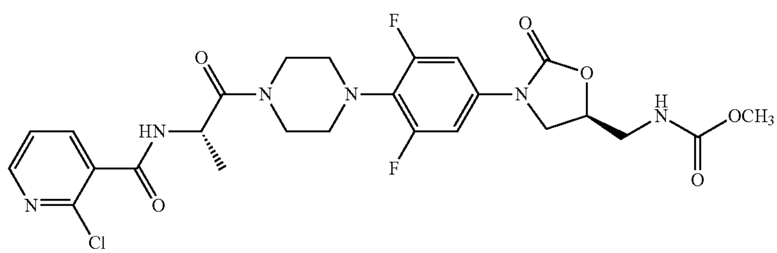 [SMILES: COC(=O)NC[C@H]1CN(c2cc(F)c(N3CCN(C(=O)[C@H](C)NC(=O)c4cccnc4Cl)CC3)c(F)c2)C(=O)O1] |
| 204 | 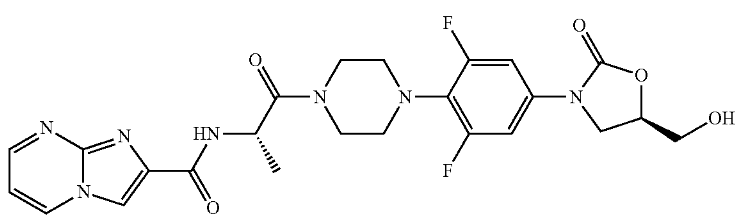 [SMILES: C[C@H](NC(=O)c1cn2cccnc2n1)C(=O)N1CCN(c2c(F)cc(N3C[C@H](CO)OC3=O)cc2F)CC1] |
| 205 | 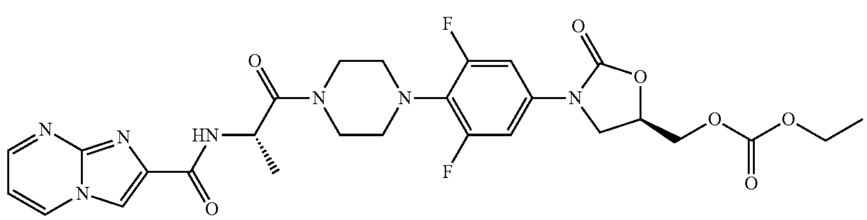 [SMILES: CCOC(=O)OC[C@H]1CN(c2cc(F)c(N3CCN(C(=O)[C@H](C)NC(=O)c4cn5cccnc5n4)CC3)c(F)c2)C(=O)O1] |
| 206 | 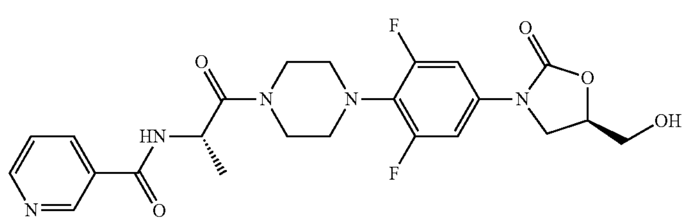 |

TABLE 1-continued

| Compound No. | Structure |
|---|---|
| 207 | 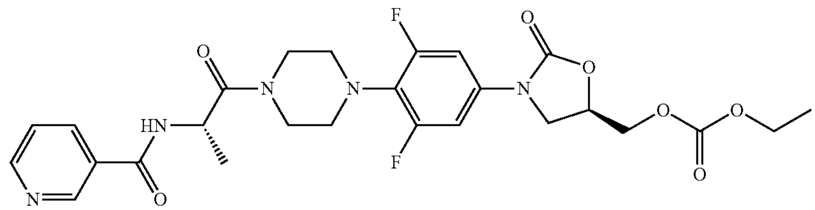 [SMILES: CCOC(=O)OC[C@H]1CN(c2cc(F)c(N3CCN(C(=O)[C@H](C)NC(=O)c4cccnc4)CC3)c(F)c2)C(=O)O1] |
| 208 | 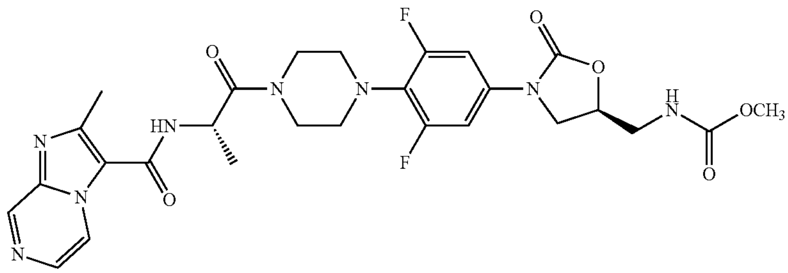 [SMILES: COC(=O)NC[C@H]1CN(c2cc(F)c(N3CCN(C(=O)[C@H](C)NC(=O)c4c(C)nc5cnccn45)CC3)c(F)c2)C(=O)O1] |

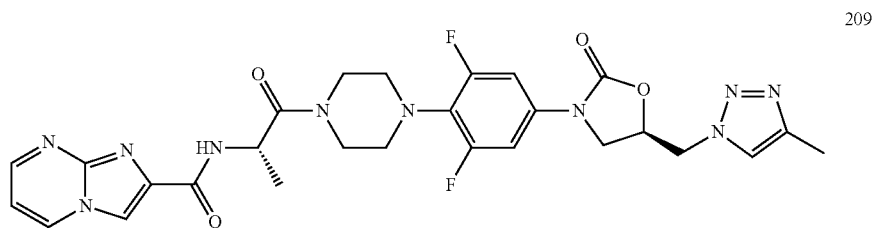 [SMILES: Cc1cn(C[C@H]2CN(c3cc(F)c(N4CCN(C(=O)[C@H](C)NC(=O)c5cn6cccnc6n5)CC4)c(F)c3)C(=O)O2)nn1]

The compounds

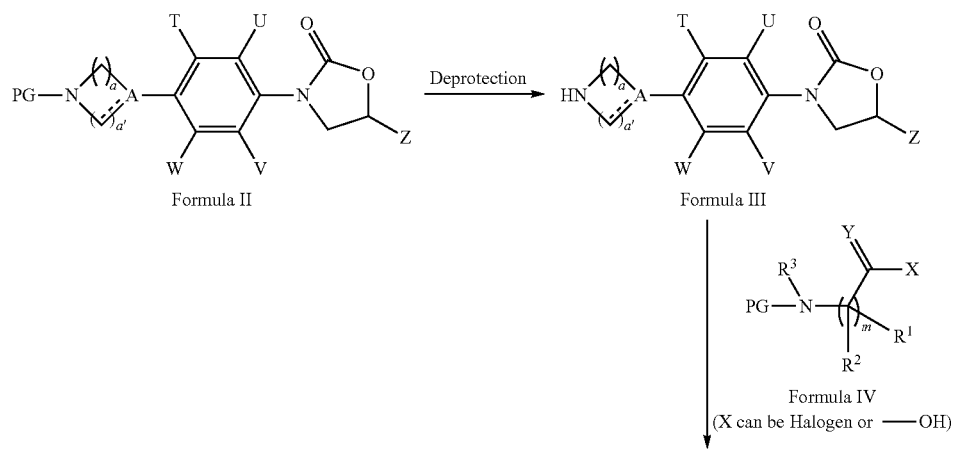

of the present invention can be prepared in accordance with one or more of the Schemes discussed herein. All of the starting materials are either commercially available or can be prepared by procedures that would be well known to one of ordinary skill in organic chemistry.

"L" denotes an appropriate leaving group and as such may vary in nature depending on the exact reaction conditions employed. Some typical leaving groups may be fluorine, chlorine, bromine, iodine, tosyl, mesyl, trifluoromethanesulfonyl and the like, but these should not be construed as limiting as many other leaving groups are also well known to those skilled in the art.

81 82

-continued

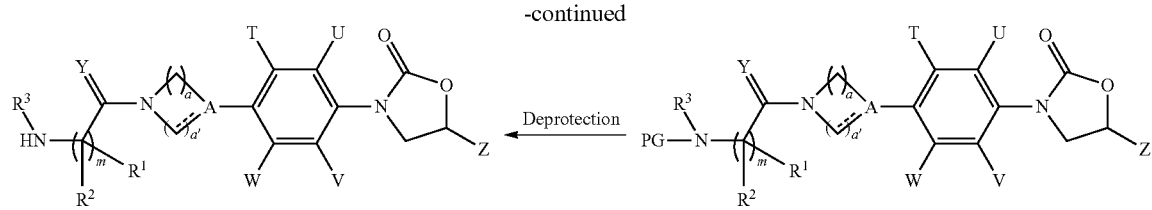

Formula IV     Deprotection     Formula V

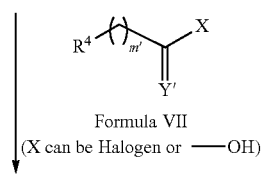

Formula VII
(X can be Halogen or —OH)

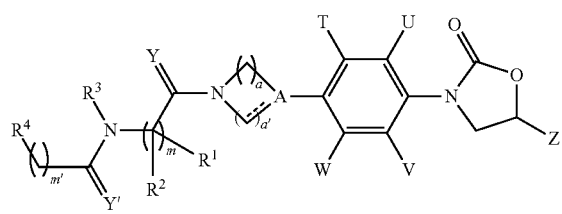

Formula I

The compounds of Formula I can be prepared from the compounds of Formula II by following Scheme 1. Deprotection of amino protecting group in the compounds of Formula II is carried out using standard deprotecting reagents for example, trifluoroacetic acid, HCl(g) saturated solution of a solvent such as methanol, ethyl acetate, diethyl ether, dioxane and the like, hydrogenation using Pd/C in a suitable polar solvent or by using a basic amine such as piperidine resulting in compounds of Formula III. (The resulting compounds may be in the form of free amine or salt depending upon the nature of protecting group and corresponding deprotecting agent used). Compounds of Formula III and Formula IV are then coupled using standard peptide coupling conditions, for example, using EDC [1-ethyl-3-(3-dimethylaminopropyl) carbodiimide]/HOBT (1-hydroxybenzotriazole) or DCC (dicyclohexyl carbodiimide), DMAP (4-dimethylaminopyridine) or HATU [O-(7-azabenzotriazole-yl)-N,N,N',N'-tetramethyluronium hexafluorophosphate/HOAT (1-hydroxy-7-azabenzotriazole) or by mixed anhydride method using ethyl chloroformate or methyl chloroformate in a suitable solvent such as DMF, DCM (dichlomethane) or THF and the like or mixtures thereof and in the presence of a suitable base such as NMM (N-methylmorpholine), DIPEA (N,N-diisopropylethylamine) or triethylamine to form compounds of Formula V. The amino protecting group (PG) is then removed by using standard deprotecting reagents, for example, trifluoroacetic acid, HCl(g) saturated solution of a solvent such as methanol, ethyl acetate, diethyl ether, dioxane and the like, hydrogenation using Pd/C in a suitable polar solvent or by using a basic amine such as piperidine to give the compounds of Formula VI. Compounds of Formula VI are then reacted with compounds of Formula VII in the presence of EDC, HOBt and the like and in the presence of a suitable base such as triethyl amine, pyridine, NMM, DMAP, DIPEA and the like and in the presence of a suitable solvents such as DMF, toluene, THF, chloroform, dichloromethane and the like or mixtures thereof to give compounds of Formula I.

Scheme 2

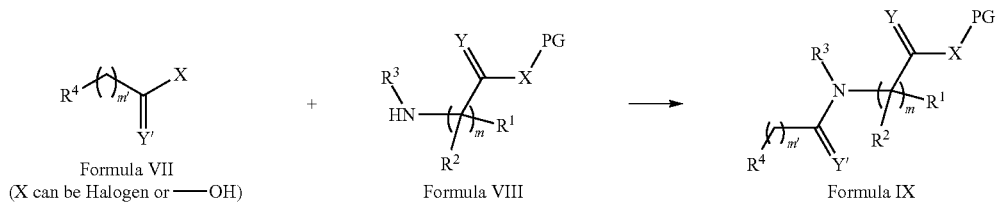

Formula VII     Formula VIII     Formula IX
(X can be Halogen or —OH)

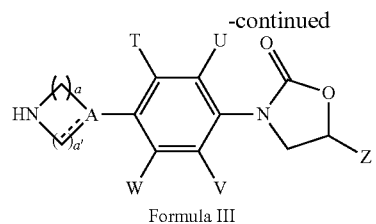
Formula III

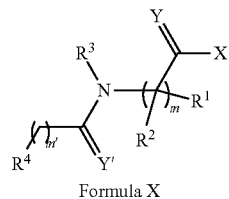
Formula X

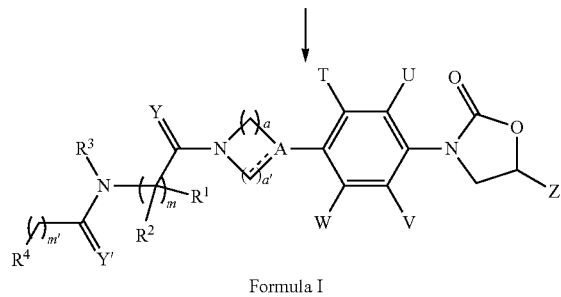
Formula I

The compounds of Formula I can also be obtained by following the Scheme 2. Compounds of Formula IX can be obtained by reacting compounds of Formula VII with compounds of Formula VIII in the presence of EDC, HOBt and the like. The reaction may be carried out in the presence of a suitable base such as triethyl amine, pyridine, NMM, DMAP, DIPEA and the like and in the presence of a suitable solvent such as DMF, toluene, THF, chloroform, dichloromethane and the like or mixtures thereof. The compounds of Formula IX are then converted to compound of Formula X using standard deprotecting reagents, familiar to those skilled in the art. Compounds of Formula X and Formula III are then coupled using standard peptide coupling conditions, for example, using EDC [1-ethyl-3-(3-dimethylaminopropyl) carbodiimide]/HOBT (1-hydroxybenzotriazole or DCC (dicyclohexyl carbodiimide), DMAP (4-dimethylaminopyridine) or HATU [O-(7-azabenzotriazole-yl)-N,N,N',N'-tetramethyluronium hexafluorophosphate/HOAT (1-hydroxy-7-azabenzotriazole) or by mixed anhydride method using ethyl chloroformate or methyl chloroformate in a suitable solvent such as DMF, DCM (dichlomethane) or THF and the like or mixtures thereof and in the presence of a suitable base such as NMM (N-methylmorpholine), DIPEA (N,N-diisopropylethylamine) or triethylamine to form compounds of Formula I.

Compounds of Formula II can be easily prepared by those skilled in art. For example compound of Formula II (when A is Nitrogen and '___' is absent) can be prepared following Scheme 3. Compounds of Formula II (when A is carbon atom and '___' is a single bond or when A is CH and '___' is absent) can be prepared following procedure reported in patent number U.S. Pat. No. 6,051,716 or WO 2003/097640 or WO 2004/113329.

Scheme 3

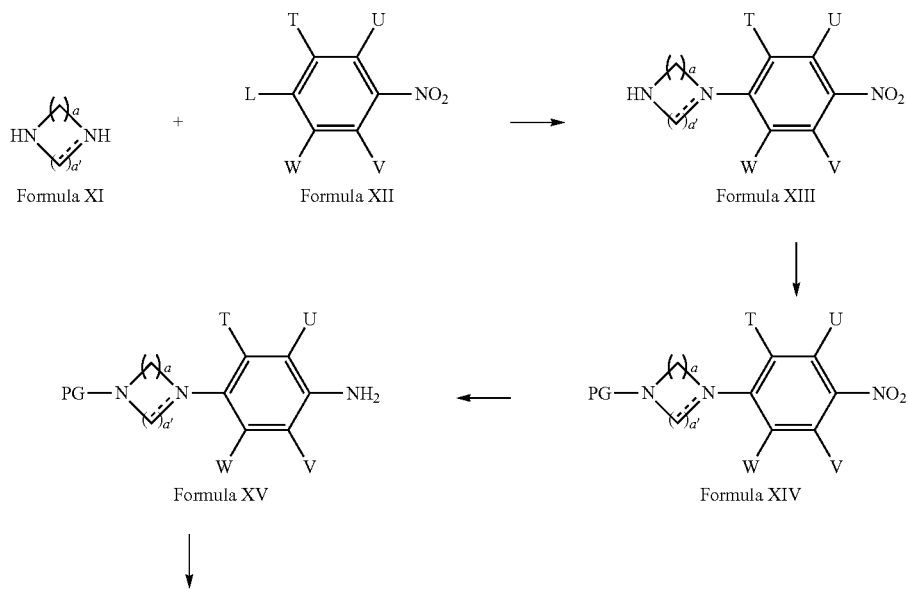

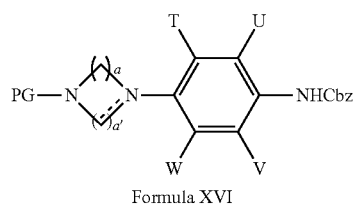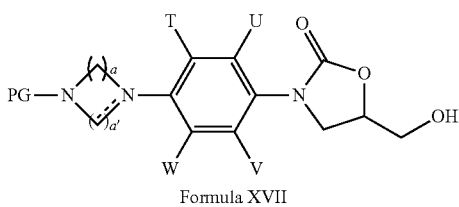

Formula XVI → Formula XVII n-BuLi
Glycidyl butyrate

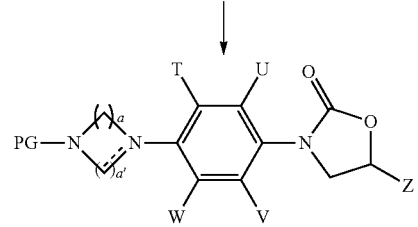

Formula II (where A is nitrogen and '--' is absent)

Compounds of Formula XIII can be obtained by reacting compounds of Formula XI with substituted nitrobenzene derivatives of Formula XII (wherein T,U,V,W are the same as defined earlier and L is an appropriate leaving group such as fluoro, chloro, bromo, iodo) in an appropriate solvent and base. Examples of appropriate solvents include acetonitrile, tetrahydrofuran, methylene dichloride, dichloroethane, DMF, DMSO and the like or mixtures thereof. Examples of appropriate bases include triethylamine, potassium carbonate, diisopropylethyl amine, KOH and the like. The compounds of Formula XIII can then be reacted with a suitable standard amino protecting group (PG), familiar to those skilled in the art, to form compounds of Formula XIV in the presence of a suitable solvent such as methylene dichloride, chloroform, THF and the like or mixtures thereof and in presence of a suitable base such as triethylamine, sodium bicarbonate, diisopropylethyl amine and the like. The nitro derivatives of Formula XIV can then be reduced to the corresponding amino compounds of Formula XV by a variety of reducing agents familiar to those skilled in the art such as hydrogenation over an appropriate catalyst such as palladium, platinum, or ruthenium on activated charcoal or chemical methods such as reaction with Fe/HCl or $SnCl_2$/HCl or $NiCl_2$/$NaBH_4$ or Fe/$NH_4$Cl. The resulting amines XV can then be treated with benzyl or methyl chloroformate and sodium bicarbonate in presence of water and acetone to form the corresponding benzyl or methyl carbamate derivatives XVI which are then deprotonated in the next step using a lithium base such as n-butyllithium followed by the addition of Glycidyl butyrate in presence of a suitable solvent such as diethylether or tetrahydrofuran to afford the oxazolidinones XVII. The hydroxyl group (Formula XVII) can then be converted to Z (Formula II) (wherein Z is as defined earlier). The exact nature of the reagents used for this conversion is dependent on the exact nature of the Z desired. For example, if Z is desired to be —$(CH_2)_n$NH(C═O)$CH_3$ group, the hydroxyl group is first converted to amino group which is then acylated in the presence of suitable acylating reagents such as acetic anhydride, acetyl chloride or the like. If Z is desired to be —$(CH_{2n})$—O-Heteroaryl, the hydroxyl group is first converted to the mesylate or other appropriate leaving group and then reacted with a suitable hydroxyl containing heterocycle in the presence of suitable base and solvent such as sodium hydride and N,N-dimethylformamide (DMF) or the like. The appropriate conditions and reagents for any particular Z group can be readily selected by those having well known skill in the art.

It is understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. The salts may be prepared during the final isolation and purification of the compounds or separately by making basic or acidic addition salts. Representative salts of basic compounds of the present invention can be prepared by reacting free base form of the compound with a suitable acid, including, but not limited to acetate, trifluoroacetate, adipate, citrate, aspartate, benzoate, benzenesulphonate, bisulfate, besylate, butyrate, camphorsulphonate, difluconate, hemisulfate, heptanoate, formate, fumarate, lactate, maleate, methanesulfonate, naphthylsulfonate, nicotinate, oxalate, picrate, pivalate, succinate, tartrate, tirchloracetat, glutamate, p-toluenesulphonate, hydrochloric, hydrobromic, sulphuric, phosphoric and the like. Representative salts of acidic compounds of the present invention can be prepared by reacting free acid form of the compound with a suitable base, including, but not limited to ammonium, calcium, magnesium, potassium, sodium salts, salts of primary, secondary and tertiary amines, substituted amines including naturally occurring ones e.g., arginine, betaine, caffeine, choline, glucamine, glucosamine, histidine, lysine, morpholine, piperazine, piperidine, purine, triethylamine and the like. Compounds of the present invention that contain a carboxylic acid (—COOH) or alcohol group, their pharmaceutically acceptable esters of carboxylic acids such as methyl, ethyl and the like, or acyl derivatives of alcohols such as acetate and the like, can be employed. Compounds of the present invention that comprise basic nitrogen atom may be quaternized with alkyl halides, alkyl sulfates and the like. Such salts permit the preparation of both water soluble and oil soluble compounds of the present invention. It should be recognized that the free base or free acid forms will typically differ from their respective salt forms somewhat in physical properties such as solubility in polar solvents, but otherwise the salts are equivalent to their respective free forms for the purpose of the invention.

The "pharmaceutically acceptable solvates" refer to solvates with water (i.e., hydrates) or pharmaceutically acceptable solvents, for example, ethanol and the like.

The invention also encompasses "prodrugs" of the compounds of the present invention which upon in-vivo administration undergo cleavage by metabolic processes before becoming active pharmacological substances. In general such prodrugs are derivatives of functional group of a compound of the invention which are readily convertible in vivo into the compound of the invention. Conventional procedures for the selection and preparation of suitable prodrug derivatives are described, for example, in "Targeted prodrug design to optimize drug delivery", *AAPS PharmaSci* (2000), 2(1), E6.

The invention also encompasses active "metabolites" of the compound of the present invention.

Various "polymorphs" of a compound of general Formula I forming part of this invention may be prepared by crystallization of a compound of Formula I under different conditions. For example, by using different solvents commonly used or their mixtures for recrystallization; crystallizations at different temperatures; various modes of cooling, ranging from very fast to very slow cooling during crystallizations, heating or melting the compound followed by gradual or fast cooling may also obtain polymorphs. The presence of polymorphs may be determined by solid probe NMR spectroscopy, IR spectroscopy, differential scanning calorimetry, powder X-ray diffraction or such other techniques.

The present invention also provides pharmaceutical compositions, comprising compounds of the present invention or their pharmaceutically acceptable derivatives, tautomeric forms, stereoisomers, polymorphs, prodrugs, metabolites, salts or solvates thereof optionally in combination with one or more pharmaceutically acceptable carriers comprising excipients and auxiliaries. The pharmaceutical compositions may be in any form known in the art, such as tablets, capsules, powders, syrups, solutions, suspensions and the like, may contain flavourants, sweeteners etc in suitable solid or liquid carriers or diluents, or in suitable sterile media to form injectable solutions or suspensions. Such compositions typically contain active compound optionally in combination with pharmaceutically acceptable carriers, diluents or solvents.

The pharmaceutical compositions of the present invention can be manufactured by the processes well known in the art, for example, by means of conventional mixing, dissolving, dry granulation, wet granulation, dragee-making, levigating, emulsifying, encapsulating, entrapping, lyophilizing processes or spray drying. The compounds or the pharmaceutical compositions comprising such compounds of the present invention may be administered in the form of any pharmaceutical Formulation. The pharmaceutical formulation will depend upon the nature of the active compound and its route of administration. Any route of administration may be used, for example oral, buccal, pulmonary, topical, parenteral (including subcutaneous, intramuscular and intravenous), transdermal, ocular (ophthalmic), by inhalation, intranasal, transmucosal, implant or rectal administration. Preferably the compounds of the present invention are administered orally, parenterally or topically.

In an embodiment, the amount of the novel compounds having the Formula I according to the present invention to be incorporated into the pharmaceutical compositions of the present invention can vary over a wide range depending on known factors such as, for example, the disorder to be treated, the severity of the disorder, the patient's body weight, the dosage form, the chosen route of administration and the number of administrations per day. Typically, the amount of the compound of Formula I in the pharmaceutical compositions of the present invention will range from approximately 0.01 mg to about 5000 mg. In an embodiment, the daily dose of composition comprising the novel compounds having the Formula I is in the range of about 0.01 mg/kg to about 100 mg/kg based on the body weight of the subject in need thereof which may be administered as a single or multiple doses.

In an embodiment, the novel compounds having the Formula I according to the present invention are particularly useful for the treatment of disease(s) or disorder(s) which are particularly acute in nature and which require a short term but mild to moderate treatment, or even some chronic conditions which favorably respond to or are alleviated by the novel compounds having the Formula I or compositions comprising them. The compositions comprising the novel compounds having the Formula I are useful prophylactically or therapeutically depending upon the pathological condition intended to be prevented or treated respectively.

The compounds of the present invention are effective against a number of aerobic and/or anaerobic Gram positive and/or Gram negative pathogens such as multi drug resistant species of *Staphylococcus, Streptococcus, Enterococcus, Bacterioides, Clostridia, H. influenza, Moraxella*, acid-fast organisms such as *Mycobacterium tuberculosis* as well as Linezolid resistant species of *Staphylococcus* and *Enterococcus*.

Thus, a further embodiment of the present invention is the use of a compound of Formula I for the manufacture of a medicament for the prophylaxis, amelioration and/or treatment of bacterial infections in a subject in need thereof preferably a mammal including a human. Another embodiment of the present invention provides methods for the management such as prophylaxis, amelioration and/or treatment of bacterial infections in a subject in need thereof preferably a mammal including a human that comprises administering a therapeutically effective amount of compound of Formula I. In still another embodiment of the present invention is provided use of the dosage form compositions comprising the novel compounds of Formula I for the treatment of disease(s)/disorder(s) which comprises administrating to a subject in need thereof a pharmaceutically effective amount of the composition.

The compounds of the present invention may be used in combination with one or more other active ingredients such as quinolones, β-lactams e.g., cephalosporins, penicillins, penams, penems and the like in the prophylaxis, amelioration and/or treatment of bacterial infections, where the combination of the active ingredients together are safer or more effective than either active ingredient alone or where incorporation of another active ingredient might reduce the dose of the compound of Formula I.

In-vitro Antibacterial Activity:

The in-vitro antibacterial activity of the compounds of the present invention (as described in Table 2) was determined by a broth microdilution following the guidelines prescribed by the Clinical and Laboratory Standards Institute (CLSI). This method is described in the CLSI Document M7-A7, Vol. 26, No. 2, "*Methods for Dilution Antimicrobial Susceptibility Test for Bacteria that Grow Aerobically; Approved Standard-Seventh Edition*", which is incorporated herein by reference. Minimum Inhibitory Concentration (MIC) is defined as the minimum concentration of test compound which inhibits the growth of bacteria as visible or seen by the naked eye. This test can also be carried out by agar dilution method.

The compounds of the present invention were tested against a panel of standard microorganisms obtained from ATCC (American type culture collection), and a Linezolid resistant strain (LRSA) i.e. PTCC 100 (Panacea type culture collection). PTCC 100 is a repository that has been created by Panacea Biotec Ltd. at Mohali, India for storage and maintenance of clinical, bacterial and other isolates developed in-house which are used for testing the test compounds. Linezolid was used as comparator in all the tests.

| Organism | Culture No. | Type |
|---|---|---|
| Staphylococcus aureus | ATCC 29213 | MSSA (Methicillin sensitive) |
| Staphylococcus aureus | ATCC 33591 | MRSA (Methicillin resistant) |
| Enterococcus faecalis | ATCC 29212 | Vancomycin Sensitive |
| Enterococcus faecium | ATCC 700221 | VRE (Vancomycin resistant E. faecium) |
| Staphylococcus aureus | PTCC 100 | LRSA (Linezolid résistant S. aureus) |

In the broth microdilution method, the compound was dissolved in dimethylsulfoxide and two fold serial dilutions were carried out in 96 well microtitre plates. The inoculum was prepared by adjusting the turbidity of actively growing broth culture and added to the wells to obtain a final bacterial count of ~2-5×10$^4$ CFU/well. The microtitre plates were incubated at 35±2° C. for 16-20 h and then read visually. MICs (µg/mL) values of some of the compounds of Formula 1 are presented in the Table 2 and Table 3.

TABLE 2

In-vitro antibacterial activity MICs (µg/mL)

| Compound No. | S. aureus ATCC 29213 | S. aureus ATCC 33591 (MRSA) | E. faecalis ATCC 29212 | E. faecium ATTC 700221 (VRE) |
|---|---|---|---|---|
| 1 | 0.5 | 0.25 | 0.5 | 0.25 |
| 2 | 2 | 2 | 2 | 1 |
| 3 | 0.5 | 0.5 | 0.5 | 0.25 |
| 4 | 0.5 | 0.5 | 0.5 | 0.5 |
| 5 | 0.5 | 0.5 | 0.5 | 0.5 |
| 6 | 0.5 | 0.5 | 0.5 | 0.5 |
| 7 | 32 | 16 | 8 | 8 |
| 11 | 1 | 0.5 | 0.5 | 0.5 |
| 12 | 0.25 | 0.25 | 0.25 | 0.25 |
| 13 | 0.5 | 0.5 | 0.5 | 0.5 |
| 14 | 0.5 | 0.5 | 0.5 | 0.25 |
| 15 | 0.5 | 0.25 | 0.5 | 0.5 |
| 16 | 0.5 | 0.5 | 0.5 | 0.5 |
| 21 | 0.5 | 0.5 | 0.5 | 0.5 |
| 22 | 1 | 1 | 0.5 | 0.25 |
| 23 | 4 | 2 | 2 | 1 |
| 24 | 1 | 0.5 | 0.5 | 0.5 |
| 25 | 2 | 2 | 1 | 1 |
| 26 | 2 | 2 | 1 | 1 |
| 31 | 2 | 1 | 1 | 1 |
| 34 | 2 | 1 | 1 | 0.5 |
| 36 | 0.25 | 0.25 | 0.25 | 0.25 |
| 36 | 0.25 | 0.25 | 0.25 | 0.25 |
| 37 | 2 | 2 | 1 | 0.5 |
| 40 | 0.5 | 0.5 | 1 | 0.5 |
| 41 | 1 | 0.5 | 1 | 0.5 |
| 43 | 1 | 0.5 | 0.5 | 0.5 |
| 51 | 0.25 | 0.125 | 0.25 | 0.125 |
| 52 | 0.5 | 0.25 | 0.5 | 0.125 |
| 53 | 0.25 | 0.25 | 0.25 | 0.125 |
| 54 | 0.25 | 0.125 | 0.25 | 0.125 |
| 55 | 0.25 | 0.125 | 0.25 | 0.125 |
| 56 | 1 | 0.5 | 1 | 0.5 |
| 57 | 0.5 | 0.5 | 0.5 | 0.25 |

TABLE 2-continued

In-vitro antibacterial activity MICs (µg/mL)

| Compound No. | S. aureus ATCC 29213 | S. aureus ATCC 33591 (MRSA) | E. faecalis ATCC 29212 | E. faecium ATTC 700221 (VRE) |
|---|---|---|---|---|
| 63 | 0.5 | 0.125 | 0.5 | 0.125 |
| 64 | 0.125 | 0.125 | 0.25 | 0.125 |
| 72 | 1 | 1 | 0.5 | 0.25 |
| 73 | 2 | 1 | 1 | 1 |
| 74 | 0.125 | 0.125 | 0.125 | 0.25 |
| 75 | 2 | 1 | 2 | 0.5 |
| 76 | 0.25 | 0.125 | 0.125 | 0.125 |
| 77 | 0.5 | 0.5 | 0.25 | 0.25 |
| 80 | 0.25 | 0.25 | 0.5 | 0.125 |
| 82 | 0.25 | 0.25 | 0.5 | 0.25 |
| 87 | 0.5 | 0.5 | 0.5 | 0.5 |
| 93 | 2 | 0.5 | 2 | 0.5 |
| 94 | 1 | 0.5 | 0.5 | 0.25 |
| 96 | 2 | 2 | 1 | 1 |
| 97 | 4 | 1 | 2 | 1 |
| 102 | 2 | 1 | 1 | 1 |
| 103 | 0.5 | 0.5 | 0.5 | 0.25 |
| 105 | 1 | 0.5 | 1 | 0.5 |
| 107 | 0.25 | 0.25 | 0.25 | 0.125 |
| 108 | 2 | 1 | 1 | 0.5 |
| 109 | 1 | 0.5 | 0.5 | 0.25 |
| 110 | 2 | 1 | 2 | 0.5 |
| 111 | 2 | 1 | 2 | 1 |
| 112 | 1 | 1 | 1 | 0.5 |
| 113 | 0.125 | 0.125 | 0.5 | 0.125 |
| 114 | 1 | 0.5 | 1 | 0.5 |
| 115 | 1 | 0.5 | 0.5 | 0.25 |
| 121 | 1 | 0.5 | 1 | 0.5 |
| 130 | 0.25 | 0.25 | 0.25 | 0.125 |
| 132 | 2 | 1 | 1 | 0.5 |
| 133 | 0.5 | 0.5 | 1 | 0.25 |
| 150 | 0.5 | 0.25 | 0.25 | 0.25 |
| 159 | 0.125 | 0.125 | 0.25 | 0.125 |
| 160 | 0.5 | 0.25 | 0.5 | 0.25 |
| 161 | 0.5 | 0.25 | 0.25 | 0.125 |
| 167 | 0.25 | 0.25 | 0.25 | 0.25 |
| 168 | 0.5 | 0.5 | 0.5 | 0.25 |
| 170 | 1 | 0.5 | 1 | 0.5 |
| 177 | 0.25 | 0.125 | 0.25 | 0.125 |
| 180 | 0.125 | 0.125 | 0.25 | 0.25 |
| 190 | 0.25 | 0.25 | 0.25 | 0.5 |
| 196 | 0.5 | 0.5 | 0.5 | 0.25 |
| 197 | 1 | 0.5 | 0.5 | 0.25 |
| Linezolid | 2 | 1 | 2 | 2 |

Development of In-house LRSA Strain (PTCC 100):

PTCC 100 was developed by a procedure similar to the one cited in *Antimicrobial Agents and Chemotherapy*, 2008, 52, 1940. Female Swiss albino mice (18-22gm) bred in-house were inoculated with *S. aureus* ATCC 29213 strain and dosed orally with Linezolid at 5 mg/kg/p.o, next day mice were sacrificed after 20-22 h and intraperitoneal swab was taken and streaked onto Mueller Hinton Agar plates containing 4 and 8 µg/mL of Linezolid. Colonies obtained on 4 µg/mL and 8 µg/mL were selected from plates and further passaged into mice (SAM), dosed orally with Linezolid at 7.5 mg/kg/p.o. Mice were sacrificed and intraperitoneal swabs were streaked onto plates containing higher linezolid concentration i.e 16 and 32 µg/mL and the process was repeated by incrementally increasing the concentration of Linezolid upto 10 mg/kg/p.o in mice, to finally obtain *S. aureus* strains resistant to Linezolid at 64 µg/mL. Minimum inhibitory concentration (MIC) of isolated colonies was determined by broth microdilution assay and MIC values of 64 µg/mL for Linezolid confirmed the development of in house LRSA strain, PTCC 100.

TABLE 3

In-vitro antibacterial activity MICs (µg/mL) against *S. aureus* PTCC 100 (LRSA)

| Compound No. | MIC(µg/mL) S. aureus PTCC 100 (LRSA) |
|---|---|
| 1 | 0.25 |
| 2 | 4 |
| 3 | 2 |
| 4 | 1 |
| 5 | 1 |
| 6 | 1 |
| 11 | 2 |
| 12 | 4 |
| 13 | 8 |
| 15 | 4 |
| 16 | 2 |
| 22 | 4 |
| 23 | 4 |
| 24 | 1 |
| 26 | 8 |
| 31 | 8 |
| 37 | 8 |
| 40 | 2 |
| 41 | 8 |
| 43 | 2 |
| 51 | 4 |
| 52 | 8 |
| 53 | 2 |
| 54 | 2 |
| 55 | 2 |
| 56 | 2 |
| 57 | 2 |
| 63 | 1 |
| 72 | 8 |
| 73 | 8 |
| 74 | 1 |
| 75 | 8 |
| 77 | 2 |
| 80 | 8 |
| 93 | 4 |
| 94 | 4 |
| 96 | 8 |
| 102 | 8 |
| 103 | 8 |
| 109 | 4 |
| 114 | 8 |
| 121 | 4 |
| 130 | 8 |
| 133 | 2 |
| 150 | 4 |
| 167 | 1 |
| 168 | 2 |
| 170 | 4 |
| Linezolid | 32 |

In-vivo Efficacy Studies:
Systemic Model of Infection in Mice

Female Swiss albino mice bred in-house were selected in weight range of 19-23 gm (n=6/group). *S. aureus* ATCC 29213 was grown overnight for 18-20 h, on Columbia Blood Agar (Difco; BD). Next day bacterial inoculum was prepared with optical density (O.D) corresponding to cell density of $\sim 2 \sim 10^9$ CFU/ml and mixed with 10% of gastric mucin (Difco; BD) in ratio of 1:1 to obtain final mucin concentration of 5% w/v. 0.5 mL of bacterial inoculum was injected intraperitoneally (i.p) into all the mice. Compounds obtained in the present invention, hereinafter referred as Test compounds were formulated in 0.25% Carboxymethylcellulose (C.M.C) and Tween 80, at different dose levels and then administered orally at 1 h and 5 h post infection. Linezolid was used as standard control. Saline was administered to the infection control group which received neither the test compound nor the standard drug. Mice were observed for 7 days post treatment. Numbers of survivors in each group were noted and $ED_{50}$ of test compound on the basis of 50% survival was calculated through regression analysis.

TABLE 4

$ED_{50}$ values (mg/kg/p.o.) against *S. aureus* ATCC 29213

| Compound No. | $ED_{50}$ values (mg/kg/p.o.) S. aureus ATCC 29213 |
|---|---|
| 77 | 6.5 |
| 105 | 5.0 |
| 115 | 5.0 |
| Linezolid | 6.0 |

EXAMPLES

The invention is explained in detail in the following examples which are given solely for the purpose of illustration only and therefore should not be construed to limit the scope of the invention. All of the starting materials are either commercially available or can be prepared by procedures that would be well known to one of ordinary skill in organic chemistry. Solvents were dried prior to use wherever necessary by standard methods (Perrin, D. D.; Armarego, W. L. F. Purification of Laboratory Chemicals, Pergamon Press: Oxford, 1988). Mass spectra (MS) were obtained by electron spray ionization (ESI) eV using Applied biosystem 4000 Q TRAP. $^1$H NMR were recorded on Bruker 400 MHz Avance II NMR spectrometer. Chemical shifts are reported as δ values in parts per million (ppm), relative to TMS as internal standard. All coupling constants (J) values are given in Hz.

Abbreviations

The following abbreviations are employed in the examples and elsewhere herein:

| | |
|---|---|
| $^1$H NMR | proton nuclear magnetic resonance |
| bs | broad singlet |
| C | centigrade |
| CDCl$_3$ | deuterated chloroform |
| CDI | 1,1'-carbonyldiimidazole |
| CuI | copper(I) iodide |
| DCM | dichloromethane |
| d | doublet |
| DAST | (diethylamino)sulfur trifluoride |
| DCC | dicyclohexyl carbodiimide |
| dd | doublet of doublet |
| DIPEA | diisopropylethylamine |
| DMAP | 4-dimethylaminopyridine |
| DMF | N,N-dimethylformamide |
| DMSO | dimethylsulfoxide |
| EDC | 1-ethyl-3-(3-dimethylaminopropyl)carbodiimide |
| ESI-MS | electron spray ionization mass Spectroscopy |
| Fe | iron |
| g | gram(s) |
| h | hour(s) |
| HATU | O-(7-azabenzotriazole-1-yl)-N,N,N',N'-tetramethyluronium hexafluorophosphate |
| HCl | hydrochloric acid |
| HOAt | 1-hydroxy-7-azabenzotriazole |
| HOBt | 1-hydroxybenzotriazole |
| Hz | hertz |
| J | coupling constant |
| KOH | potassium hydroxide |
| M | molar |
| m | multiplet |
| mg | milligram |
| min | minutes |
| mL | milliliter |
| mmol | millimoles |
| mol | moles |

-continued

| | |
|---|---|
| NaHCO₃ | sodium bicarbonate |
| n-BuLi | n-butyl lithium |
| NaBH₄ | sodium borohydride |
| NH₄Cl | ammonium chloride |
| NMM | N-methylmorpholine |
| NMR | nuclear magnetic resonance |
| NiCl₂ | nickel(II) chloride |
| Pd/C | palladium on carbon |
| Pet. Ether | petroleum ether |
| q | quartet |
| r.t. | room temperature |
| s | singlet |
| SnCl₂ | tin(II) chloride |
| t | triplet |
| TFA | trifluoroacetic acid |
| THF | tetrahydrofuran |
| TLC | thin layer chromatography |

Preparation of Starting Materials:

Intermediate I 1-(2,6-Difluoro-4-nitro-phenyl)-piperazine

A solution of piperazine (24 g, 0.28 mol) and 3,4,5-trifluoronitrobenzene (13 mL, 0.11 mol) in acetonitrile (200 mL) was stirred at 60° C. The progress of reaction was monitored by TLC. On completion, acetonitrile was evaporated under reduced pressure. The residue was dissolved in ethyl acetate (300 mL) and resulting solution was washed with water (100 mL), brine (100 mL), dried over anhydrous sodium sulphate and concentrated in vacuo. The residue was purified by column chromatography (silica gel, 1:9 methanol:chloroform) to provide title compound (25.8 g, 92%) as orange solid.
ESIMS (m/z): 244.1 (M+1)

Intermediate II 4-(2,6-Difluoro-4-nitro-phenyl)-piperazine-1-carboxylic acid tert-butyl ester To a solution of 1-(2,6-difluoro-4-nitro-phenyl)-piperazine (Intermediate I) (25 g, 0.1 mol), in THF (200 mL) was added Boc anhydride (26.2 g, 0.12 mol) at 0° C. The solution was stirred at 0° C. and progress of reaction was monitored by TLC. On completion, THF was evaporated under reduced pressure and the solid obtained was washed with Pet. ether (3×100 mL). The yellow solid (34 g, 96%) obtained was subjected to next reaction without further purification.
ESIMS (m/z): 344.1 (M+1)

Intermediate III 4-(4-Amino-2,6-difluoro-phenyl)-piperazine-1-carboxylic acid tert-butyl ester To a solution of 4-(2,6-difluoro-4-nitro-phenyl)-piperazine-1-carboxylic acid tert-butyl ester (Intermediate II) (30 g, 0.09 mol), in methanol (500 mL) under argon atmosphere was added 10% Pd/C (4.5 g, 15 mol% by weight). Flask was evacuated and hydrogen was introduced with the help of balloon. The reaction mixture was stirred under hydrogen and progress of the reaction was monitored by TLC. On completion, the reaction mixture was filtered through celite pad using methanol as solvent. The filterate was evaporated to provide title compound (26 g, 95%) as pale yellow solid.
ESIMS (m/z): 336.7 (M+23), 314.8 (M+1)

Intermediate IV 4-(4-Benzyloxycarbonylamino-2,6-difluoro-phenyl)-piperazine-1-carboxylic acid tert-butyl ester To a solution of 4-(4-amino-2,6-difluoro-phenyl)-piperazine-1-carboxylic acid tert-butyl ester (Intermediate III) (25 g, 0.08 mol), in 1:1 acetone:water (300 mL) was added sodium bicarbonate (15.1 g, 0.18 mol). The resulting solution was cooled to 0° C. and benzyl chloroformate (40 mL, 0.24 mol, 50% solution in toluene) was added dropwise. The reaction mixture was stirred at r.t. and progress of the reaction was monitored by TLC. On completion, solvent was evaporated under reduced pressure and the residue was dissolved in ethyl acetate (500 mL). The organic layer was washed with water (2×50 mL), brine (100 mL), dried over anhydrous sodium sulphate and concentrated in vacuo. The residue was purified by column chromatography (silica gel, 2:3 ethyl acetate:Pet. ether) to provide title compound (32 g, 90%) as off white solid.
ESIMS (m/z): 448.0 (M+1)

Intermediate V

4-[2,6-Difluoro-4-((5R)-hydroxymethyl-2-oxo-oxazolidin-3-yl)-phenyl]-piperazine-1-carboxylic acid tert-butyl ester To a solution of 4-(4-benzyloxycarbonylamino-2,6-difluoro-phenyl)-piperazine-1-carboxylic acid tert-butyl ester (Intermediate IV) (30 g, 0.067 mol), in dry THF (300 mL) was added n-BuLi (75 mL, 0.12 mol, 1.6 M solution in hexane) dropwise under nitrogen atmosphere at −78° C. The reaction mixture was stirred at the same temperature for one hour and then (R)-glycidyl butyrate (10.4 mL, 0.074 mol) was added dropwise over a period of 5 min. The reaction mixture was stirred at −78° C. for additional two hours and then warmed to r.t. The progress of reaction was monitored by TLC and on completion, the reaction mixture was quenched with saturated NH₄Cl solution (400 mL) and extracted with ethyl acetate (4×200 mL). The organic layer was washed with brine (100 mL), dried over anhydrous sodium sulphate and concentrated in vacuo. The residue was purified by column chromatography (silica gel, 3:2 ethyl acetate:Pet. ether) to provide title compound (18 g, 65%) as off white solid.
ESIMS (m/z): 452.7 (M+39), 436.6 (M+23), 414.7 (M+1)

Intermediate VI

4-[2,6-Difluoro-4-((5R)-methanesulfonyloxymethyl-2-oxo-oxazolidin-3-yl)-phenyl]-piperazine-1-carboxylic acid tert-butyl ester To a solution of 4-[2,6-difluoro-4-((5R)-hydroxymethyl-2-oxo-oxazolidin-3-yl)-phenyl]-piperazine-1-carboxylic acid tert-butyl ester (Intermediate V) (10 g, 24.2 mmol), in DCM (100 mL) was added triethylamine (10.5 mL, 73 mmol). The reaction mixture was cooled to 0° C. and methanesulfonyl chloride (2.8 mL, 36 mmol) was added dropwise. The reaction mixture was stirred at r.t. and progress of the reaction was monitored by TLC. On completion, the reaction mixture was diluted with DCM (100 mL). The organic layer was washed with water (25 mL), brine (25 mL), dried over anhydrous sodium sulphate and concentrated in vacuo. The crude product (11.3 g, 95%) was obtained as brown solid and subjected to further reaction without any purification.

ESIMS (m/z): 514.8 (M+23), 492.6 (M+1)

Intermediate VII

4-[4-((5R)-Azidomethyl-2-oxo-oxazolidin-3-yl)-2,6-difluoro-phenyl]-piperazine-1-carboxylic acid tert-butyl ester To a solution of 442,6-difluoro-4-((5R)-methanesulfonyloxymethyl-2-oxo-oxazolidin-3-yl)-phenyThpiperazine-1-carboxylic acid tert-butyl ester (Intermediate VI) (11 g, 22.4 mmol), in DMF (50 mL) was added sodium azide (4.37 g, 67.2 mmol). The reaction mixture was stirred at 80° C. and progress of the reaction was monitored by TLC. On completion, the reaction mixture was diluted with water (100 mL) and extracted with ethyl acetate (2×100 mL). The organic layer was washed with brine (50 mL), dried over anhydrous sodium sulphate and concentrated in vacuo. The crude product (8 g, 82%) was obtained as off white solid and subjected to further reaction without any purification.

ESIMS (m/z): 439.7 (M+1)

Intermediate VIII

4-[4-((5S)-Aminomethyl-2-oxo-oxazolidin-3-yl)-2,6-difluoro-phenyl]-piperazine-1-carboxylic acid tert-butyl ester A mixture of 4-[4-((5R)-azidomethyl-2-oxo-oxazolidin-3-yl)-2,6-difluoro-phenyl]-piperazine-1-carboxylic acid tert-butyl ester (Intermediate VII) (5 g, 11.4 mmol) and triphenylphosphine (3.3 g, 12.5 mmol) in THF (80 mL) was stirred at r.t. for 3 h. Water (3 mL) was added and the reaction mixture was stirred at 40° C. for 16 h. The reaction mixture was then diluted with water (50 mL) and extracted with ethyl acetate (4×50 mL). The organic layer was washed with brine (50 mL), dried over anhydrous sodium sulphate and concentrated in vacuo. The residue was purified by column chromatography (silica gel, 1:9 methanol:chloroform) to provide title compound (3.5 g, 74%) as off white solid.

ESIMS (m/z): 435.8 (M+23), 413.7 (M+1)

Intermediate IX

4-[2,6-Difluoro-4-(2-oxo-(5R)-[1,2,3]triazol-1-ylmethyl-oxazolidin-3-yl)-phenyl]-piperazine-1-carboxylic acid tert-butyl ester To a solution of 4-[4-((5R)-azidomethyl-2-oxo-oxazolidin-3-yl)-2,6-difluoro-phenyl]-piperazine-1-carboxylic acid tert-butyl ester (Intermediate VII) (2 g, 4.6 mmol), in dioxane (25 mL) was added bicyclo[2.2.1]hepta-2,5-diene (1.9 mL, 18.5 mmol) and the resulting solution was stirred at 60° C. for 8 h. The solvent was evaporated and the residue was purified by column chromatography (silica gel, 1:20 methanol:chloroform) to provide title compound (1.47 g, 70%) as white solid.

ESIMS (m/z): 465.7 (M+1)

Intermediate X

4-{2,6-Difluoro-4-[(5R)-(isoxazol-3-yloxymethyl)-2-oxo-oxazolidin-3-yl]-phenyl}-piperazine-1-carboxylic acid tert-butyl ester To a stirred solution of 442,6-difluoro-4-[(5R)-hydroxymethyl-2-oxo-oxazolidin-3-yl)-phenyl]-piperazine-1-carboxylic acid tert-butyl ester (Intermediate V) (1 g, 2.4 mmol), in dry THF (25 mL) was added 3-hydroxyisoxazole (0.23 g, 2.64 mmol), diethylazodicarboxylate (0.6 mL, 3.6 mmol) and triphenylphosphine (0.94 g, 3.6 mmol) under nitrogen atmosphere. The resulting solution was stirred at r.t. and progress of reaction was monitored by TLC. On completion, solvent was evaporated under reduced pressure and residue was dissolved in ethyl acetate (100 mL). The organic layer was washed with water (25 mL), brine (25 mL), dried over anhydrous sodium sulphate and concentrated in vacuo. The residue was purified by column chromatography (silica gel, 2:3 ethyl acetate:Pet. ether) to provide title compound (680 mg, 59%) as off white solid.

ESIMS (m/z): 481.1 (M+1)

Example I

Imidazo[1,2-a]pyrazine-2-carboxylic acid [2-(4-{4-[(5S)-(acetylamino-methyl)-2-oxo-oxazolidin-3-yl]-2,6-difluoro-phenyl}-piperazin-1-yl)-2-oxo-ethyl]-amide

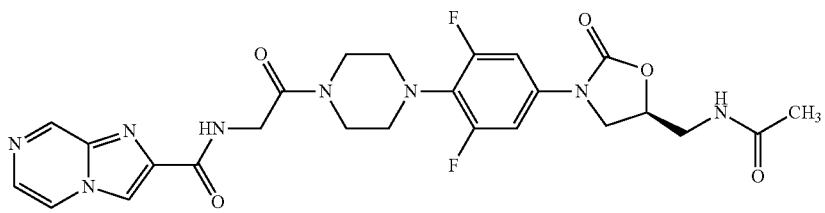 [SMILES: CC(=O)NC[C@H]1CN(c2cc(F)c(N3CCN(C(=O)CNC(=O)c4cn5ccncc5n4)CC3)c(F)c2)C(=O)O1]

Step 1: 4-{4-[(5S)-(Acetylamino-methyl)-2-oxo-oxazolidin-3-yl]-2,6-difluoro-phenyl}-piperazine-1-carboxylic acid tert-butyl ester A solution of 4-[4-((5R)-azidomethyl-2-oxo-oxazolidin-3-yl)-2,6-difluoro-phenyl]-piperazine-1-carboxylic acid tert-butyl ester (Intermediate VII) (600 mg, 1.37 mmol), in thioacetic acid (5 mL) was stirred for 12 h at r.t. The reaction mixture was then adsorbed on silica gel and purified by column chromatography (silica gel, 1:20 methanol:chloroform) to yield the title compound (440 mg, 70%) as white solid.

ESIMS (m/z): 455.4 (M+1)

Step 2: 4-{4-[(5S)-(Acetylamino-methyl)-2-oxo-oxazolidin-3-yl]-2,6-difluoro-phenyl}-piperazin-1-ium trifluoro-acetate To a stirred solution of compound (425 mg, 0.94 mmol) obtained in Step 1, in DCM (2 mL) at 0° C. under nitrogen atmosphere was added TFA (3 mL) dropwise. The mixture was stirred at 0° C. and progress of the reaction was monitored by TLC. On completion, excess TFA and DCM were evaporated under reduced pressure to obtain the title compound (425 mg, 97%) as brown solid and subjected to further reaction without any purification.

ESIMS (m/z): 355.4 (M+1, free amine).

Step 3: [2-(4-{4-[(5S)-(Acetylamino-methyl)-2-oxo-oxazolidin-3-yl]-2,6-Difluoro-phenyl}-piperazin-1-yl)-2-oxo-ethyl]-carbamic acid tert-butyl ester To a solution of compound (400 mg, 0.86 mmol) obtained in step 2, in DCM (25 mL), were added N-(tert-butoxycarbonyl)glycine (171 mg, 0.98 mmol), EDC (188 mg, 0.98 mmol), HOBt (132 mg, 0.98 mmol) and NMM (0.22 mL, 2 mmol) at 0° C. The reaction mixture was stirred at r.t. and progress of the reaction was monitored by TLC. On completion, the reaction mixture was diluted with DCM (100 mL). The organic layer was washed with water (50 mL), brine (50 mL), dried over anhydrous sodium sulphate and concentrated in vacuo. The residue was purified by column chromatography (silica gel, 3:5 ethyl acetate:Pet. ether) to provide title compound (370 mg, 85%) as white solid.

ESIMS (m/z): 550.3 (M+39), 534.4 (M+23), 512.5 (M+1)

Step 4: (S)-2-(4-{4-[5-(Acetylamino-methyl)-2-oxo-oxazolidin-3-yl]-2,6-difluoro-phenyl}-piperazin-1-yl)-2-oxo-ethyl-ammonium; trifluoro-acetate:

To a stirred solution of compound (350 mg, 0.69 mmol) obtained in Step 3, in DCM (1.5 mL) at 0° C. under nitrogen atmosphere was added TFA (2.5 mL) dropwise. The mixture was stirred at 0° C. and progress of the reaction was monitored by TLC. On completion, excess TFA and DCM were evaporated under reduced pressure to obtain the title compound (340 mg, 95%) as brown solid and subjected to further reaction without any purification.

ESIMS (m/z): 412.4 (M+1, free amine).

Step 5: Imidazo [1,2-a]pyrazine-2-carboxylic acid [2-(4-{4-[(5S)-(acetylamino-methyl)-2-oxo-oxazolidin-3-yl]-2,6-difluoro-phenyl}-piperazin-1-yl)-2-oxo-ethyl]-amide To a solution of compound (300 mg, 0.57 mmol) obtained in step 4, in DMF (10 mL), were added imidazo[1,2-a]pyrazine-2-carboxylic acid (107 mg, 0.66 mmol), EDC (127 mg, 0.66 mmol), HOBt (89 mg, 0.66 mmol) and NMM (0.15 mL, 1.35 mmol) at 0° C. The reaction mixture was stirred at r.t. and progress of the reaction was monitored by TLC. On completion, DMF was evaporated in vacuo and residue was dissolved in chloroform (100 mL). The organic layer was washed with water (50 mL), brine (50 mL), dried over anhydrous sodium sulphate and concentrated in vacuo. The residue was purified by column chromatography (silica gel, 1:20 methanol:chloroform) to provide title compound (220 mg, 69%) as white solid.

¹H NMR (400 MHz, CDCl₃, δ): 2.03 (s, 3H), 3.10-3.25 (m, 4H), 3.50-3.65 (m, 3H), 3.65-3.75 (m, 2H), 3.80-3.90 (m, 2H), 4.00 (t, J=9.0 Hz, 1H), 4.34 (d, J=4.5 Hz, 2H), 4.70-4.85 (m, 1H), 5.97 (t, J=6.1 Hz, 1H), 7.12 (d, J=10.9 Hz, 2H), 7.94 (d, J=4.7 Hz, 1H), 8.09 (dd, J=4.6 and 1.5 Hz, 1H), 8.22 (d, J=0.5 Hz, 1H), 8.35 (t, J=4.4 Hz, 1H), 9.13 (d, J=0.9 Hz, 1H).

ESIMS (m/z): 579.3 (M+23), 557.3 (M+1)

Example II

Imidazo[1,2-a]pyrazine-2-carboxylic acid {2-[4-(2,6-difluoro-4-{2-oxo-(5S)-[(3-phenyl-acryloylamino)-methyl]-oxazolidin-3-yl}-phenyl)-piperazin-1-yl]-2-oxo-ethyl}-amide

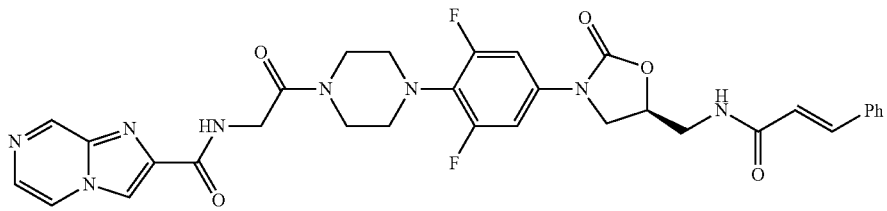 [SMILES: O=C(/C=C/c1ccccc1)NC[C@H]1CN(c2cc(F)c(N3CCN(C(=O)CNC(=O)c4cn5ccncc5n4)CC3)c(F)c2)C(=O)O1]

Step 1: 4-(2,6-Difluoro-4-{2-oxo-(5S)-[(3-phenyl-acryloylamino)-methyl]-oxazolidin-3-yl}-phenyl)-piperazine-1-carboxylic acid tert-butyl ester To a solution of 4-[4-((5S)-Aminomethyl-2-oxo-oxazolidin-3-yl)-2,6-difluoro-phenyl]-piperazine-1-carboxylic acid tert-butyl ester (Intermediate VIII) (300 mg, 0.73 mmol) in DMF (25 mL), were added cinnamic acid (130 mg, 0.87 mmol), EDC (182 mg, 0.95 mmol), HOBt (128 mg, 0.95 mmol) and NMM (0.08 mL, 0.73 mmol) at 0° C. The reaction mixture was stirred at r.t. and progress of the reaction was monitored by TLC. On completion, DMF was evaporated in vacuo and residue was dissolved in chloroform (100 mL). The organic layer was washed with water (50 mL), brine (50 mL), dried over anhydrous sodium sulphate and concentrated in vacuo. The residue was purified by column chromatography (silica gel, 1:20 methanol:chloroform) to provide title compound (332 mg, 85%) as white solid.

ESIMS (m/z): 543.9 (M+1)

Compound obtained in Step 1 Example II, was converted to imidazo[1,2-a]pyrazine-2-carboxylic acid {2-[4-(2,6-difluoro-4-{2-oxo-(5S)-[(3-phenyl-acryloylamino)-methyl]-oxazolidin-3-yl}-phenyl)-piperazin-1-yl]-2-oxo-ethyl}-amide following the procedure described in steps 2 to 5 in Example I.

¹H NMR (400 MHz, CDCl₃, δ): 3.05-3.20 (m, 4H), 3.60-3.70 (m, 2H), 3.75-3.90 (m, 5H), 4.04 (t, J=9.1 Hz, 1H), 4.33 (s, 2H), 4.80-4.95 (m, 1H), 6.48 (d, J=15.7 Hz, 1H), 7.12 (d, J=10.8 Hz, 2H), 7.30-7.45 (m, 3H), 7.50-7.60 (m, 3H), 7.62 (d, J=15.6 Hz, 1H), 7.94 (d, J=4.7 Hz, 1H), 8.10-8.15 (m, 1H), 8.29 (s, 1H), 8.40-8.45 (m, 1H), 9.11 (s, 1H).

ESIMS (m/z): 667.8 (M+23), 645.9 (M+1)

Example III

{3-[3,5-Difluoro-4-(4-{(2S)-[(pyridine-3-carbonyl)-amino]-propionyl}-piperazin-1-yl)-phenyl]-2-oxo-oxazolidin-(5S)-ylmethyl}-carbamic acid methyl ester

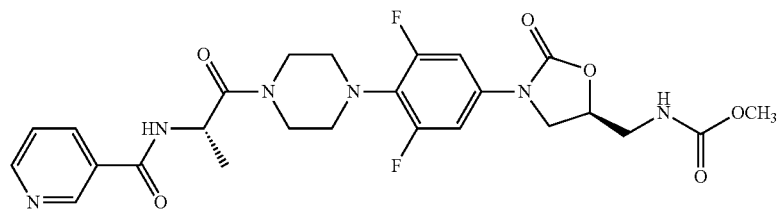

Step 1: 4-{2,6-Difluoro-4-[(5S)-(methoxycarbony-lamino-methyl)-2-oxo-oxazolidin-3-yl]-phenyl}-piperazine-1-carboxylic acid tert-butyl ester To a solution of 4-[4-((5S)-aminomethyl-2-oxo-oxazolidin-3-yl)-2,6-difluoro-phenyl]-piperazine-1-carboxylic acid tert-butyl ester (Intermediate VIII) (375 mg, 0.91 mmol), in DCM (25 mL) was added triethyl amine (0.53 mL, 3.8 mmol). The resulting solution was cooled to 0° C. and methyl chloroformate (0.11 mL, 1.4 mmol) was added dropwise. The reaction mixture was stirred at r.t. and progress of the reaction was monitored by TLC. On completion, the reaction mixture was diluted with DCM (100 mL). The organic layer was washed with water (25 mL), brine (25 mL), dried over anhydrous sodium sulphate and concentrated in vacuo. The residue was purified by column chromatography (silica gel, 3:10 ethyl acetate:Pet. ether) to provide title compound (330 mg, 77%) as white solid.

ESIMS (m/z): 471.4 (M+1)

Compound obtained in Step 1 Example III, was converted to {3-[3,5-Difluoro-4-(4-{(2S)-[(pyridine-3-carbonyl)-amino]-propionyl}-piperazin-1-yl)-phenyl]-2-oxo-oxazolidin-(5S)-ylmethyl}-carbamic acid methyl ester following the procedure described in steps 2 to 5 in Example I. (S)-N-(tert-butoxycarbonyl)alanine was used in place of N-(tert-butoxycarbonyl)glycine in step 3 and nicotinic acid in place of imidazo[1,2-a]pyrazine-2-carboxylic acid in step 5.

$^1$H NMR (400 MHz, CDCl$_3$, δ): 1.49 (d, J=6.7 Hz, 3H), 3.10-3.25 (m, 4H), 3.45-3.90 (m, 10H), 4.04 (t, J=8.9 Hz, 1H), 4.70-4.85 (m, 1H), 5.05-5.15 (m, 1H), 5.15-5.25 (m, 1H), 7.13 (d, J=10.7 Hz, 2H), 7.40 (dd, J=7.8 and 5.0 Hz, 1H), 7.50 (d, J=6.6 Hz, 1H), 8.13 (d, J=7.9 Hz, 1H), 8.75 (d, J=4.5 Hz, 1H), 9.07 (s, 1H).

ESIMS (m/z): 585.9 (M+39), 569.8 (M+23), 548.0 (M+1)

Example IV

{3-[3,5-Difluoro-4-(4-{(2S)-[(imidazo[1,2-a]pyrimidine-2-carbonyl)-amino]-propionyl}-piperazin-1-yl)-phenyl]-oxazolidin-(5S)-ylmethyl}-carbamic acid ethyl ester

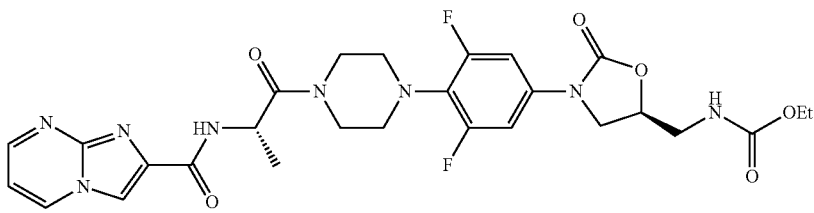 [SMILES: CCOC(=O)NC[C@H]1CN(c2cc(F)c(N3CCN(C(=O)[C@H](C)NC(=O)c4cn5cccnc5n4)CC3)c(F)c2)C(=O)O1]

Step 1: 4-{2,6-Difluoro-4-[(5S)-(ethoxycarbonylamino-methyl)-2-oxo-oxazolidin-3-yl]-phenyl}-piperazine-1-carboxylic acid tert-butyl ester The title compound was prepared following the procedure as described in Step 1 Example III by replacing methyl chloroformate with ethyl chloroformate.

ESIMS (m/z): 485.4 (M+1)

Compound obtained in Step 1 Example IV, was converted to {3-[3,5-difluoro-4-(4-{(2S)-[(imidazo[1,2-a]pyrimidine-2-carbonyl)-amino]-propionyl}-piperazin-1-yl)-phenyl]-oxazolidin-(5S)-ylmethyl}-carbamic acid ethyl ester following the procedure described in steps 2 to 5 in Example I. (S)-N-(tert-butoxycarbonyl)alanine was used in place of N-(tert-butoxycarbonyl)glycine in step 3 and Imidazo[1,2-a]pyrimidine-2-carboxylic acid in place of imidazo[1,2-a]pyrazine-2-carboxylic acid in step 5.

$^1$H NMR (400 MHz, CDCl$_3$, δ): 1.22 (t, J=7.6 Hz, 3H), 1.50 (d, J=6.8 Hz, 3H), 3.10-3.25 (m, 4H), 3.35-3.85 (m, 7H), 4.00 (t, J=9.0 Hz, 1H), 4.05-4.20 (m, 2H), 4.70-4.85 (m, 1H), 5.05-5.20 (m, 2H), 7.06 (dd, J=6.8 and 4.2 Hz, 1H), 7.13 (d, J=10.9 Hz, 2H), 7.38 (d, J=7.2 Hz, 1H), 8.32 (s, 1H), 8.69 (dd, J=4.1 and 2.0 Hz, 1H), 9.75 (dd, J=6.7 and 1.7 Hz, 1H).

ESIMS (m/z): 601.9 (M+1)

Example V

{3-[3,5-Difluoro-4-(4-{2-[(pyridine-3-carbonyl)-amino]-acetyl}-piperazin-1-yl)-phenyl]-2-oxo-oxazolidin-(5S)-ylmethyl}-carbamic acid isopropyl ester

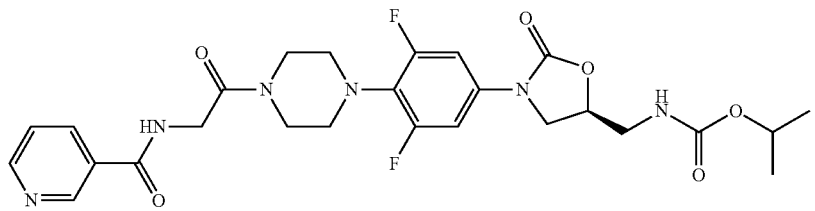 [SMILES: CC(C)OC(=O)NC[C@H]1CN(c2cc(F)c(N3CCN(C(=O)CNC(=O)c4cccnc4)CC3)c(F)c2)C(=O)O1]

Step 1: Imidazole-1-carboxylic acid isopropyl ester

To a solution of CDI (2 g, 12.33 mmol), in DCM (25 mL) was added isopropyl alcohol (0.95 mL, 12.33 mmol) at 0° C. The reaction mixture was stirred at r.t. and progress of the reaction was monitored by TLC. On completion, the reaction mixture was diluted with DCM (100 mL). The organic layer was washed with water (25 mL), brine (25 mL), dried over anhydrous sodium sulphate and concentrated in vacuo. The residue was purified by column chromatography (silica gel, 1:10 ethyl acetate:Pet. ether) to provide title compound (330 mg, 77%) as colourless viscous oil.

ESIMS (m/z): 155.1 (M+1)

Step 2: 4-{2,6-Difluoro-4-[(5S)-(isopropoxycarbonylamino-methyl)-2-oxo-oxazolidin-3-yl]-phenyl}-piperazine-1-carboxylic acid tert-butyl ester To a stirred solution of compound (150 mg, 0.97 mmol) obtained in Step 1, in DMF (5 mL) at 0° C. under nitrogen atmosphere was added 4-[4-((5S)-aminomethyl-2-oxo-oxazolidin-3-yl)-2,6-difluoro-phenyl]-piperazine-1-carboxylic acid tert-butyl ester (intermediate VIII) (400 mg, 0.97 mmol). The reaction mixture was stirred at 80° C. and progress of the reaction was monitored by TLC. On completion, the reaction mixture was diluted with ethyl acetate (100 mL). The organic layer was washed with water (4×25 mL), brine (25 mL), dried over anhydrous sodium sulphate and concentrated in vacuo. The residue was purified by column chromatography (silica gel, 3:10 ethyl acetate: Pet. ether) to provide title compound (350 mg, 72%) as cream solid. ESIMS (m/z): 499.5 (M+1)

Compound obtained in Step 2 Example V, was converted to {3-[3,5-Difluoro-4-(4-{2-[(pyridine-3-carbonyl)-amino]-acetyl}-piperazin-1-yl)-phenyl]-2-oxo-oxazolidin-(5S)-yl-methyl}-carbamic acid isopropyl ester following the procedure described in steps 2 to 5 in Example I. Nicotinic acid was used in place of imidazo[1,2-a]pyrazine-2-carboxylic acid.

$^1$H NMR (400 MHz, CDCl$_3$, δ): 1.18 (d, J=6.1 Hz, 3H), 1.24 (d, J=6.1 Hz, 3H), 3.10-3.25 (m, 4H), 3.50-3.65 (m, 4H), 3.70-3.85 (m, 3H), 4.00 (t, J=8.9 Hz, 1H), 4.31 (d, J=3.8 Hz, 2H), 4.70-4.80 (m, 1H), 4.85-4.95 (m, 1H), 5.00-5.10 (m, 1H), 7.13 (d, J=10.9 Hz, 2H), 7.35-7.45 (m, 2H), 8.15-8.20 (m 1H), 8.76 (dd, J=4.7 and 1.2 Hz, 1H), 9.09 (d, J=1.8 Hz, 1H).

ESIMS (m/z): 599.8 (M+39), 583.9 (M+23), 561.8 (M+1)

Example VI

{3-[3,5-Difluoro-4-(4-{(2S)-[(imidazo[1,2-a]pyrimidine-2-carbonyl)-amino]-3-methyl-butyryl}-piperazin-1-yl)-phenyl]-2-oxo-oxazolidin-(5S)-ylmethyl}-carbamic acid methyl ester

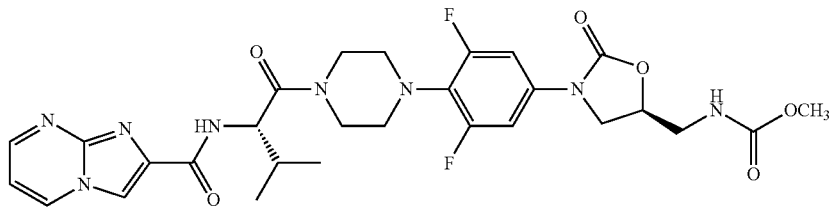 [SMILES: COC(=O)NC[C@H]1CN(c2cc(F)c(N3CCN(C(=O)[C@@H](NC(=O)c4cn5cccnc5n4)C(C)C)CC3)c(F)c2)C(=O)O1]

Title compound was prepared following the steps as described in Example III. (S)-N-(tert-butoxycarbonyl)valine was used in place of (S)-N-(tert-butoxycarbonyl)alanine in step 3 and imidazo[1,2-a]pyrimidine-2-carboxylic acid in place of nicotinic acid in step 5.

$^1$H NMR (400 MHz, CDCl$_3$, δ): 1.00 (d, J=6.7 Hz, 3H), 1.08 (d, J=6.8 Hz, 3H), 2.10-2.25 (m, 1H), 3.10-3.30 (m, 4H), 3.50-3.65 (m, 2H), 3.69 (s, 3H), 3.70-3.85 (m, 4H), 3.85-3.95 (m, 1H), 3.99 (t, J=8.9 Hz, 1H), 4.70-4.85 (m, 1H), 5.00-5.10 (m, 1H), 5.14 (t, J=6.3 Hz, 1H), 6.95-7.05 (m, 2H), 7.12 (d, J=10.9 Hz, 2H), 8.33 (s, 1H), 8.69 (dd, J=4.0 and 2.0 Hz, 1H), 9.74 (dd, J=6.9 and 1.9 Hz, 1H).

ESIMS (m/z): 637.9 (M+23), 615.8 (M+1)

Example VII

N-(2-{4-[2,6-Difluoro-4-(2-oxo-(5R)-[1,2,3]triazol-1-ylmethyl-oxazolidin-3-yl)-phenyl]-piperazin-1-yl}-(1S)-methyl-2-oxo-ethyl)-nicotinamide

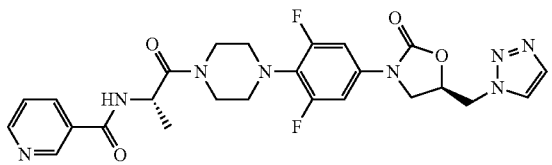 [SMILES: C[C@H](NC(=O)c1cccnc1)C(=O)N1CCN(c2c(F)cc(N3C[C@H](Cn4ccnn4)OC3=O)cc2F)CC1]

4-[2,6-Difluoro-4-(2-oxo-(5R)-[1,2,3]triazol-1-ylmethyl-oxazolidin-3-yl)-phenyl]-piperazine-1-carboxylic acid tert-butyl ester (Intermediate IX) was converted to title compound following the procedure described in steps 2 to 5 in Example I. (S)-N-(tert-butoxycarbonyl)alanine was used in place of N-(tert-butoxycarbonyl)glycine and nicotinic acid in place of imidazo[1,2-a]pyrazine-2-carboxylic acid.

$^1$H NMR (400 MHz, CDCl$_3$, δ): 1.49 (d, J=6.8 Hz, 3H), 3.10-3.30 (m, 4H), 3.65-3.80 (m, 3H), 3.80-3.90 (m, 1H), 3.92 (dd, J=9.3 and 6.0 Hz, 1H), 4.11 (t, J=9.1 Hz, 1H), 5.00-5.20 (m, 2H), 6.99 (d, J=10.7 Hz, 2H), 7.39 (dd, J=7.9 and 4.9 Hz, 1H), 7.47 (d, J=6.8 Hz, 1H), 7.76 (d, J=8.5 Hz, 2H), 8.10-8.15 (m, 1H), 8.75 (dd, J=4.7 and 1.2 Hz, 1H), 9.06 (d, J=2.0 Hz, 1H).

ESIMS (m/z): 563.7 (M+23), 541.5 (M+1)

Example VIII

N-[2-(4-{2,6-Difluoro-4-[(5R)-(4-fluoromethyl-[1,2,3]triazol-1-ylmethyl)-2-oxo-oxazolidin-3-yl]-phenyl}-piperazin-1-yl)-(1S)-methyl-2-oxo-ethyl]-nicotinamide

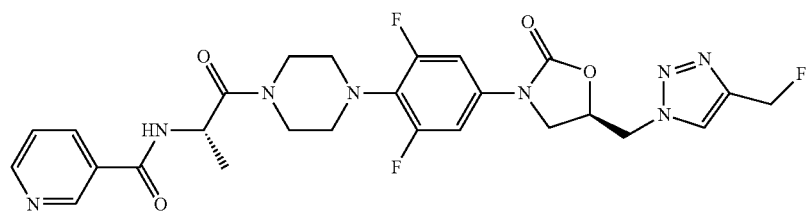 [SMILES: C[C@H](NC(=O)c1cccnc1)C(=O)N1CCN(c2c(F)cc(N3C[C@H](Cn4cc(CF)nn4)OC3=O)cc2F)CC1]

Step 1: 4-{2,6-Difluoro-4-[(5R)-(4-hydroxymethyl-[1,2,3]triazol-1-ylmethyl)-2-oxo-oxazolidin-3-yl]-phenyl}-piperazine-1-carboxylic acid tert-butyl ester To a stirred solution of 4-[4-((5R)-azidomethyl-2-oxo-oxazolidin-3-yl)-2,6-difluoro-phenyl]-piperazine-1-carboxylic acid tert-butyl ester (Intermediate VII) (1.3 g, 2.97 mmol) in THF (25 mL) was added propargyl alcohol (0.5 mL, 8.9 mmol), DIPEA (1.1 mL, 5.94 mmol) and CuI (0.28 g, 1.48 mmol) at 0° C. The reaction mixture was stirred at r.t. and progress of the reaction was monitored by TLC. On completion, reaction mixture was quenched with saturated solution of ammonium chloride in liquor ammonia (20 mL), diluted with water (50 mL) and extracted with ethyl acetate (4×50 mL). The organic layer was washed with brine (25 mL), dried over anhydrous sodium sulphate and concentrated in vacuo. The residue was purified by column chromatography (silica gel, 1:10 methanol:chloroform) to provide title compound (1.24 g, 85%) as cream solid.

ESIMS (m/z): 495.5 (M+1)

Step 2: 4-{2,6-Difluoro-4-[(5R)-(4-fluoromethyl-[1,2,3]triazol-1-ylmethyl)-2-oxo-oxazolidin-3-yl]-phenyl}-piperazine-1-carboxylic acid tert-butyl ester To a stirred solution of compound (500 mg, 1.01 mmol) obtained in Step 1, in DCM (15 mL) was added DAST (0.5 mL, 4.04 mmol) at −20° C. The reaction mixture was stirred at r.t. and progress of the reaction was monitored by TLC. On completion, reaction mixture was quenched with saturated solution of sodium bicarbonate (25 mL) and extracted with DCM (4×50 mL). The organic layer was washed with water (50 mL), brine (25 mL), dried over anhydrous sodium sulphate and concentrated in vacuo. The residue was purified by column chromatography (silica gel, 1:10 methanol:chloroform) to provide title compound (300 mg, 60%) as cream solid.

ESIMS (m/z): 497.5 (M+1)

Compound obtained in Step 2 Example VIII, was converted to N-[2-(4-{2,6-difluoro-4-[(5R)-(4-fluoromethyl-[1,2,3]triazol-1-ylmethyl)-2-oxo-oxazolidin-3-yl]-phenyl}-piperazin-1-yl)-(1S)-methyl-2-oxo-ethyl]-nicotinamide following the procedure described in steps 2 to 5 in Example I. (S)-N-(tert-butoxycarbonyl)alanine was used in place of N-(tert-butoxycarbonyl)glycine and nicotinic acid was used in place of imidazo[1,2-a]pyrazine-2-carboxylic acid.

$^1$H NMR (400 MHz, CDCl$_3$, δ): 1.49 (d, J=6.8 Hz, 3H), 3.10-3.25 (m, 4H), 3.60-3.75 (m, 3H), 3.80-3.90 (m, 1H), 3.91 (dd, J=9.4 and 6.3 Hz, 1H), 4.13 (t, J=9.1 Hz, 1H), 4.60-4.70 (m, 2H), 5.05-5.20 (m, 2H), 5.43 (s, 1H), 5.55 (s, 1H), 7.01 (d, J=10.8 Hz, 2H), 7.39 (dd, J=7.8 and 4.9 Hz, 1H), 7.48 (d, J=6.8 Hz, 1H), 7.88 (d, J=2.4 Hz, 1H), 8.10-8.15 (m, 1H), 8.74 (dd, J=4.8 and 1.6 Hz, 1H), 9.06 (d, J=2.0 Hz, 1H).

ESIMS (m/z): 595.9 (M+23), 573.6 (M+1)

Example IX

Carbonic acid 3-[3,5-difluoro-4-(4-{2-[(imidazo[1,2-a]pyrazine-2-carbonyl)-amino]-acetyl}-piperazin-1-yl)-phenyl]-2-oxo-oxazolidin-(5R)-ylmethyl ester ethyl ester

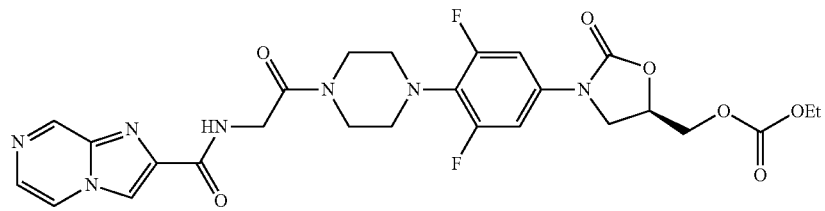 [SMILES: CCOC(=O)OC[C@H]1CN(c2cc(F)c(N3CCN(C(=O)CNC(=O)c4cn5ccncc5n4)CC3)c(F)c2)C(=O)O1]

Step 1: 4-[4-((5R)-Ethoxycarbonyloxymethyl-2-oxo-oxazolidin-3-yl)-2,6-difluoro-phenyl]-piperazine-1-carboxylic acid tert-butyl ester To a solution of 4-[2,6-difluoro-4-((5R)-hydroxymethyl-2-oxo-oxazolidin-3-yl)-phenyl]-piperazine-1-carboxylic acid tert-butyl ester (500 mg, 1.21 mmol) (intermediate V), in DCM (20 mL) was added triethyl amine (0.7 mL, 4.85 mmol). The resulting solution was cooled to 0° C. and ethyl chloroformate (0.23 mL, 2.42 mmol) was added dropwise. The reaction mixture was stirred at r.t. and progress of the reaction was monitored by TLC. On completion, the reaction mixture was diluted with DCM (50 mL). The organic layer was washed with water (25 mL), brine (25 mL), dried over anhydrous sodium sulphate and concentrated in vacuo. The residue was purified by column chromatography (silica gel, 3:10 ethyl acetate:Pet. ether) to provide title compound (470 mg, 80%) as white solid.

ESIMS (m/z): 508.1 (M+23), 486.4 (M+1)

Compound obtained in Step 1 Example IX, was converted to Carbonic acid 3-[3,5-difluoro-4-(4-{2-[imidazo[1,2-a]pyrazine-2-carbonyl)-amino]-acetyl}-piperazin-1-yl)-phenyl]-2-oxo-oxazolidin-(5R)-ylmethyl ester ethyl ester following the procedure described in steps 2 to 5 in Example I.

$^1$H NMR (400 MHz, CDCl$_3$, δ): 1.32 (t, J=7.1 Hz, 3H), 3.10-3.25 (m, 4H), 3.55-3.65 (m, 2H), 3.75-3.85 (m, 3H), 4.06 (t, J=9.0 Hz, 1H), 4.23 (q, J=7.2 Hz, 2H), 4.30-4.45 (m, 4H), 4.80-4.95 (m, 1H), 7.14 (d, J=10.9 Hz, 2H), 7.93 (d, J=4.7 Hz, 1H), 8.09 (dd, J=4.7 and 1.6 Hz, 1H), 8.22 (s, 1H), 8.30-8.40 (m, 1H), 9.13 (d, J=0.8 Hz, 1H).

ESIMS (m/z): 586.4 (M−1)

The compounds listed in Tables 5 and 6 were prepared essentially following the procedures described for Examples I to IX.

TABLE 5

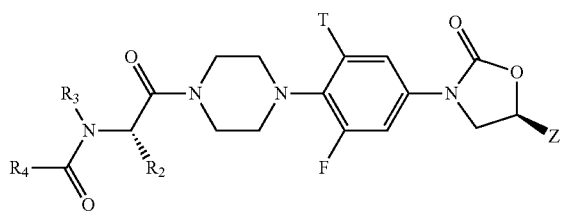

| S. No. | R$^4$ | R$^2$ | R$^3$ | T | Z | ESIMS |
|---|---|---|---|---|---|---|
| 1 | imidazo[1,2-a]pyrazine | —H | —H | —F | ~NHC(O)OCH$_3$ | 595.4 (M + 23)<br>573.1 (M + 1) |
| 2 | imidazo[1,2-a]pyrazine | —CH$_2$CH(CH$_3$)$_2$ | —H | —F | ~NHC(O)CH$_3$ | 635.4 (M + 23)<br>613.4 (M + 1) |
| 3 | imidazo[1,2-a]pyrazine | —H | —H | —H | ~NHC(O)OCH$_3$ | 593.4 (M + 39)<br>577.5 (M + 23)<br>555.4 (M + 1) |

TABLE 5-continued

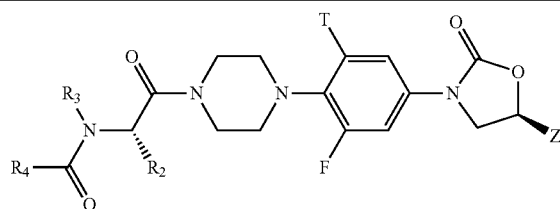

| S. No. | R⁴ | R² | R³ | T | Z | ESIMS |
|---|---|---|---|---|---|---|
| 4 | imidazo[1,2-a]pyrazin-2-yl | —CH₂OH | —H | —F | —CH₂NHC(O)OCH₃ | 641.3 (M + 39)<br>625.2 (M + 23)<br>603.5 (M + 1) |
| 5 | imidazo[1,2-a]pyrazin-2-yl | —CH₃ | —H | —F | —CH₂NHC(O)OCH₃ | 587.3 (M + 1) |
| 6 | imidazo[1,2-a]pyrimidin-2-yl | —H | —H | —F | —CH₂NHC(O)CH₃ | 595.3 (M + 39)<br>579.2 (M + 23)<br>557.2 (M + 1) |
| 7 | imidazo[1,2-a]pyrazin-2-yl | cyclopentyl | —H | —F | —CH₂NHC(O)CH₃ | 649.2 (M + 39)<br>633.4 (M + 23)<br>611.4 (M + 1) |
| 8 | imidazo[1,2-a]pyrazin-2-yl | —CH₂CN | —H | —F | —CH₂NHC(O)CH₃ | 594.3 (M − 1) |
| 9 | imidazo[1,2-a]pyrazin-2-yl | —CH₂OH | —H | —F | —CH₂NHC(O)CH₃ | 625.3 (M + 39)<br>609.4 (M + 23)<br>587.2 (M + 1) |
| 10 | imidazo[1,2-a]pyrazin-2-yl | —CH₃ | —H | —H | —CH₂NHC(O)OCH₃ | 607.4 (M + 39)<br>591.4 (M + 23)<br>569.4 (M + 1) |
| 11 | imidazo[1,2-a]pyrimidin-2-yl | —H | —H | —F | —CH₂NHC(O)OCH₃ | 611.3 (M + 39)<br>595.3 (M + 23)<br>573.3 (M + 1) |
| 12 | 6-fluoroimidazo[1,2-a]pyridin-2-yl | —H | —H | —F | —CH₂NHC(O)OCH₃ | 612.6 (M + 23)<br>590.5 (M + 1) |
| 13 | imidazo[1,2-a]pyrazin-2-yl | —H | —H | —H | —CH₂O-isoxazol-3-yl | 587.3 (M + 23)<br>565.3 (M + 1) |

TABLE 5-continued

| S. No. | R⁴ | R² | R³ | T | Z | ESIMS |
|---|---|---|---|---|---|---|
| 14 | imidazo[1,2-a]pyrazin-2-yl | —H | —H | —H | CH₂-triazolyl | 571.2 (M + 23)<br>549.4 (M + 1) |
| 15 | imidazo[1,2-a]pyrimidin-2-yl | —H | —H | —H | CH₂NHC(O)OCH₃ | 593.3 (M + 39)<br>577.4 (M + 23)<br>555.4 (M + 1) |
| 16 | 6-fluoroimidazo[1,2-a]pyridin-2-yl | —H | —H | —H | CH₂NHC(O)OCH₃ | 610.4 (M + 39)<br>594.4 (M + 23)<br>572.4 (M + 1) |
| 17 | imidazo[1,2-a]pyrimidin-2-yl | —H | —H | —H | CH₂-O-isoxazolyl | 586.9 (M + 23)<br>565.3 (M + 1) |
| 18 | imidazo[1,2-a]pyrazin-2-yl | —H | —H | —F | CH₂-triazolyl | 605.3 (M + 39)<br>589.3 (M + 23)<br>567.4 (M + 1) |
| 19 | imidazo[1,2-a]pyrimidin-2-yl | —H | —H | —F | CH₂-triazolyl | 605.1 (M + 39)<br>589.3 (M + 23)<br>567.4 (M + 1) |
| 20 | 2-methylimidazo[1,2-a]pyrazin-3-yl | —H | —H | —H | CH₂NHC(O)OCH₃ | 607.1 (M + 39)<br>591.4 (M + 23)<br>569.5 (M + 1) |
| 21 | imidazo[1,2-a]pyrimidin-2-yl | —H | —C₂H₅ | —F | CH₂NHC(O)OCH₃ | 639.5 (M + 39)<br>623.5 (M + 23)<br>601.4 (M + 1) |
| 22 | imidazo[1,2-a]pyrazin-2-yl | —H | —H | —H | CH₂OH | 536.1 (M + 39)<br>520.2 (M + 23)<br>498.1 (M + 1) |
| 23 | imidazo[1,2-a]pyrazin-2-ylmethyl | —H | —H | —F | CH₂NHC(O)OCH₃ | 625.5 (M + 39)<br>609.3 (M + 23)<br>587.2 (M + 1) |

TABLE 5-continued

| S. No. | R⁴ | R² | R³ | T | Z | ESIMS |
|---|---|---|---|---|---|---|
| 24 | [1,2,4]triazolo[4,3-a]pyrazin-3-yl | —H | —H | —H | CH₂NHC(O)OCH₃ | 594.4 (M + 39) 578.4 (M + 23) 556.2 (M + 1) |
| 25 | imidazo[1,2-a]pyrazin-2-yl | —H | —CH₃ | —H | CH₂NHC(O)OCH₃ | 567.5 (M − 1) |
| 26 | imidazo[1,2-a]pyrazin-2-yl | —H | —C₂H₅ | —F | CH₂NHC(O)OCH₃ | 639.6 (M + 39) 623.1 (M + 23) 601.2 (M + 1) |
| 27 | imidazo[1,2-a]pyrimidin-2-yl | —H | —H | —H | CH₂OH | 536.2 (M + 39) 520.4 (M + 23) 498.4 (M + 1) |
| 28 | imidazo[1,2-a]pyrimidin-2-yl | —H | —CH₃ | —F | CH₂NHC(O)OCH₃ | 609.5 (M + 23) 587.5 (M + 1) |
| 29 | imidazo[1,2-a]pyrimidin-2-yl | —H | —H | —H | CH₂OC(O)CH(NH₂)CH₃ | 591.5 (M + 23) 569.4 (M + 1) |
| 30 | imidazo[1,2-a]pyrimidin-2-yl | —H | —H | —H | CH₂F | 522.4 (M + 23) 500.4 (M + 1) |
| 31 | imidazo[1,2-a]pyrimidin-2-yl | —H | —C₂H₅ | —H | CH₂NHC(O)OCH₃ | 621.5 (M + 39) 605.5 (M + 23) 583.4 (M + 1) |
| 32 | imidazo[1,2-a]pyrimidin-2-yl | —H | —H | —F | CH₂OH | 514.4 (M − 1) |
| 33 | imidazo[1,2-a]pyrimidin-2-yl | —H | —CH₂C≡CH | —F | CH₂NHC(O)OCH₃ | 649.2 (M + 39) 633.3 (M + 23) 611.3 (M + 1) |

TABLE 5-continued

| S. No. | R⁴ | R² | R³ | T | Z | ESIMS |
|---|---|---|---|---|---|---|
| 34 | imidazo[1,2-a]pyrazin-2-yl | —H | —H | —H | -CH₂-O-C(O)-O-ethyl | 568.2 (M − 1) |
| 35 | imidazo[1,2-a]pyrazin-2-yl | —H | —CH₃ | —H | -CH₂-OH | 550.4 (M + 39); 534.3 (M + 23); 512.3 (M + 1) |
| 36 | imidazo[1,2-a]pyrazin-2-yl | —H | —H | —F | -CH₂-O-C(O)-O-isobutyl | 639.1 (M + 23); 617.1 (M + 1) |
| 37 | imidazo[1,2-a]pyrazin-2-yl | —H | —H | —H | -CH₂-O-C(O)-CH₂-cyclopropyl | 603.0 (M + 23); 580.9 (M + 1) |
| 38 | imidazo[1,2-a]pyrazin-2-yl | —H | —H | —H | -CH₂-O-C(O)-ethyl | 577.1 (M + 23); 554.9 (M + 1) |
| 39 | imidazo[1,2-a]pyrazin-2-yl | —H | —H | —H | -CH₂-O-C(O)-CH₂-NH₂ | 577.7 (M + 23); 555.8 (M + 1) |
| 40 | imidazo[1,2-a]pyrazin-2-yl | —H | —H | —F | -CH₂-O-P(O)(O-phenyl)₂ | 771.0 (M + 23); 749.0 (M + 1) |
| 41 | imidazo[1,2-a]pyrimidin-2-yl | —H | —H | —F | -CH₂-OH | 554.8 (M + 39); 538.8 (M + 23); 516.8 (M + 1) |
| 42 | imidazo[1,2-a]pyrimidin-2-yl | —H | —H | —F | -CH₂-O-C(O)-O-ethyl | 627.0 (M + 39); 611.1 (M + 23); 588.9 (M + 1) |

TABLE 5-continued

| S. No. | R⁴ | R² | R³ | T | Z | ESIMS |
|---|---|---|---|---|---|---|
| 43 | [1,2,4]triazolo[4,3-a]pyrazin-3-yl | —H | —H | —F | —CH₂OH | 555.9 (M + 39) 539.9 (M + 23) 517.7 (M + 1) |
| 44 | 2-methyl-imidazo[1,2-a]pyrazin-3-yl | —H | —H | —F | —CH₂OH | 552.9 (M + 23) 530.8 (M + 1) |
| 45 | imidazo[1,2-a]pyrazin-2-yl | —H | —H | —F | —CH₂OC(O)CH₂NH₂ | 572.4 (M + 1) |
| 46 | 6-fluoro-imidazo[1,2-a]pyridin-2-yl | —H | —H | —F | —CH₂OH | 571.6 (M + 39) 555.7 (M + 23) 533.9 (M + 1) |
| 47 | imidazo[1,2-a]pyrazin-2-yl | —H | —H | —F | —CH₂F | 541.0 (M + 23) 518.9 (M + 1) |
| 48 | imidazo[1,2-a]pyrazin-2-yl | —H | —H | —F | —CH₂NHC(O)OCH₂CH(CH₃)₂ | 638.0 (M + 23) 616.0 (M + 1) |
| 49 | imidazo[1,2-a]pyrazin-2-yl | —H | —H | —H | —CHF₂ | 540.8 (M + 23) 518.8 (M + 1) |
| 50 | imidazo[1,2-a]pyrazin-2-yl | —H | —H | —F | —CH₂NHC(O)OCH₂CH=CH₂ | 621.9 (M + 23) 599.9 (M + 1) |
| 51 | imidazo[1,2-a]pyrazin-2-yl | —H | —H | —F | —CH₂NHC(O)OCH₂CH₃ | 609.9 (M + 23) 588.0 (M + 1) |
| 52 | imidazo[1,2-a]pyrazin-2-yl | —H | —H | —F | —CH₂NHC(O)CF₃ | 633.9 (M + 23) 612.0 (M + 1) |

TABLE 5-continued

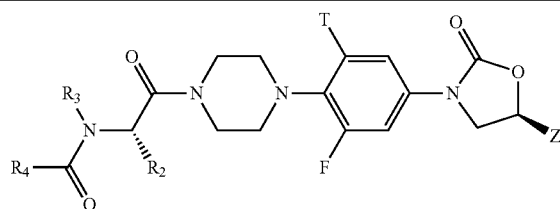

| S. No. | R⁴ | R² | R³ | T | Z | ESIMS |
|---|---|---|---|---|---|---|
| 53 | imidazo[1,2-a]pyrazin-2-yl | —H | —H | —F | —CH₂NHC(O)-cyclopropyl | 621.8 (M + 39)<br>606.0 (M + 23)<br>584.0 (M + 1) |
| 54 | imidazo[1,2-a]pyrazin-2-yl | —H | —H | —F | —CH₂NHC(O)CH₂OH | 595.9 (M + 23)<br>573.9 (M + 1) |
| 55 | imidazo[1,2-a]pyrimidin-2-yl | —H | —H | —F | —CH₂F | 540.9 (M + 23)<br>518.9 (M + 1) |
| 56 | imidazo[1,2-a]pyrazin-2-yl | —H | —H | —H | —CH₂NHC(O)CH₂NH₂ | 577.1 (M + 23)<br>554.9 (M + 1) |
| 57 | imidazo[1,2-a]pyrazin-2-yl | —H | —H | —F | —CHF₂ | 558.9 (M + 23)<br>536.8 (M + 1) |
| 58 | imidazo[1,2-a]pyrazin-2-yl | —H | —H | —F | —CH₂NHC(O)CHCl₂ | 647.6 (M + 23)<br>625.7 (M + 1) |
| 59 | imidazo[1,2-a]pyrazin-2-yl | —H | —H | —F | —CH₂NHC(O)OCH₂CCl₃ | 711.3 (M + 23)<br>689.4 (M + 1) |
| 60 | imidazo[1,2-a]pyrazin-2-yl | —H | —H | —H | —CH₂NHC(O)OCH₂CH(CH₃)₂ | 619.9 (M + 23)<br>598.0 (M + 1) |
| 61 | imidazo[1,2-a]pyrazin-2-yl | —H | —H | —F | —CH₂NHC(O)OCH₂Ph | 671.9 (M + 23)<br>649.9 (M + 1) |
| 62 | imidazo[1,2-a]pyrazin-2-yl | —H | —H | —H | —CH₂NHC(O)OCH₂CH=CH₂ | 603.9 (M + 23)<br>581.9 (M + 1) |

TABLE 5-continued

| S. No. | R⁴ | R² | R³ | T | Z | ESIMS |
|---|---|---|---|---|---|---|
| 63 | imidazo[1,2-a]pyrazin-2-yl | —H | —H | —H | -CH₂-NH-C(O)-CH₂CH₂-phenyl (N-ethyl-like linker) | 652.0 (M + 23)<br>630.0 (M + 1) |
| 64 | imidazo[1,2-a]pyrazin-2-yl | —H | —H | —H | -CH₂-NH-C(O)-O-ethyl | 607.7 (M + 39)<br>591.8 (M + 23)<br>570.0 (M + 1) |
| 65 | imidazo[1,2-a]pyrazin-2-yl | —H | —H | —H | -CH₂-NH-C(O)-cyclopropyl | 603.9 (M + 39)<br>587.9 (M + 23)<br>565.9 (M + 1) |
| 66 | imidazo[1,2-a]pyrazin-2-yl | —H | —H | —H | -CH₂-NH-C(O)-CH₂-cyclopropyl | 618.0 (M + 39)<br>602.0 (M + 23)<br>579.9 (M + 1) |
| 67 | imidazo[1,2-a]pyrimidin-2-yl | —H | —H | —F | -CH₂-NH-C(O)-CH=CH-phenyl | 638.8 (M + 39)<br>668.0 (M + 23)<br>645.9 (M + 1) |
| 68 | pyrazin-2-yl | —H | —H | —H | -CH₂-NH-C(O)-OCH₃ | 554.9 (M + 39)<br>538.8 (M + 23)<br>516.5 (M + 1) |
| 69 | imidazo[1,2-a]pyrazin-2-yl | —H | —H | —F | -CH₂-NH-C(O)-O-phenyl | 658.0 (M + 23)<br>636.0 (M + 1) |
| 70 | imidazo[1,2-a]pyrimidin-2-yl | —H | —H | —F | -CH₂-NH-C(O)-O-ethyl | 625.9 (M + 39)<br>609.9 (M + 23)<br>588.1 (M + 1) |
| 71 | imidazo[1,2-a]pyrimidin-2-yl | —H | —H | —H | -CH₂-NH-C(O)-O-ethyl | 592.0 (M + 23)<br>569.8 (M + 1) |

TABLE 5-continued

| S. No. | R⁴ | R² | R³ | T | Z | ESIMS |
|---|---|---|---|---|---|---|
| 72 | pyrazinyl | —H | —H | —F | CH₂NHC(O)CH₃ | 518.8 (M + 1) |
| 73 | pyrazinyl | —H | —H | —F | CH₂NHC(O)OCH₃ | 572.9 (M + 39)<br>556.9 (M + 23)<br>534.9 (M + 1) |
| 74 | imidazo[1,2-a]pyrazinyl | —H | —C₂H₅ | —F | CH₂NHC(O)OEt | 637.9 (M + 23)<br>615.9 (M + 1) |
| 75 | 3-phenylisoxazol-5-yl | —H | —H | —F | CH₂NHC(O)OCH₃ | 622.0 (M + 23)<br>599.9 (M + 1) |
| 76 | imidazo[1,2-a]pyrimidinyl | —H | —H | —F | CH₂NHC(O)OCH₂CH₂F | 628.0 (M + 23)<br>606.0 (M + 1) |
| 77 | imidazo[1,2-a]pyrimidinyl | —H | —H | —F | CH₂NHC(O)OCH₂CH₂OCH₃ | 655.8 (M + 39)<br>640.0 (M + 23)<br>618.0 (M + 1) |
| 78 | 1-(4-fluorophenyl)-1H-1,2,3-triazol-4-yl | —H | —H | —H | CH₂NHC(O)OCH₃ | 637.1 (M + 39)<br>621.3 (M + 23)<br>599.5 (M + 1) |
| 79 | pyridin-2-yl | —H | —H | —H | CH₂NHC(O)OEt | 567.1 (M + 39)<br>551.5 (M + 23)<br>529.1 (M + 1) |
| 80 | 7-chloro-1-cyclopropyl-6-fluoro-4-oxo-1,4-dihydroquinolin-3-yl | —H | —H | —F | CH₂NHC(O)OCH₃ | 713.9 (M + 23)<br>692.0 (M + 1) |

TABLE 5-continued

| S. No. | R⁴ | R² | R³ | T | Z | ESIMS |
|---|---|---|---|---|---|---|
| 81 | imidazo[1,2-a]pyrimidin-2-yl | —H | —C₂H₅ | —F | ethyl carbamate CH₂ | 637.9 (M + 23)<br>615.9 (M + 1) |
| 82 | pyrazin-2-yl | —H | —H | —H | ethyl carbamate CH₂ | 552.9 (M + 23)<br>530.9 (M + 1) |
| 83 | imidazo[1,2-a]pyrimidin-2-yl | —H | —CH₃ | —F | ethyl carbamate CH₂ | 640.2 (M + 39)<br>624.1 (M + 23)<br>602.1 (M + 1) |
| 84 | 2-methylimidazo[1,2-a]pyrazin-3-yl | —H | —H | —H | ethyl carbamate CH₂ | 606.1 (M + 23)<br>584.0 (M + 1) |
| 85 | 1H-indol-2-yl | —H | —H | —F | methyl carbamate CH₂ | 570.0 (M − 1) |
| 86 | [1,2,4]triazolo[4,3-a]pyrazin-3-yl | —H | —H | —F | ethyl carbamate CH₂ | 627.0 (M + 39)<br>611.0 (M + 23)<br>589.0 (M + 1) |
| 87 | pyridin-3-yl | —H | —H | —F | methyl carbamate CH₂ (methyl branch) | 556.0 (M + 23)<br>534.0 (M + 1) |
| 88 | 6-morpholinopyridin-3-yl | —H | —H | —F | methyl carbamate CH₂ | 641.0 (M + 23)<br>619.0 (M + 1) |
| 89 | furan-2-yl | —H | —H | —F | methyl carbamate CH₂ | 560.6 (M + 39)<br>545.0 (M + 23)<br>522.9 (M + 1) |
| 90 | 2-ethyl-4-oxoquinazolin-3(4H)-yl-propyl | —H | —H | —F | methyl carbamate CH₂ | 678.9 (M + 23)<br>657.0 (M + 1) |

TABLE 5-continued

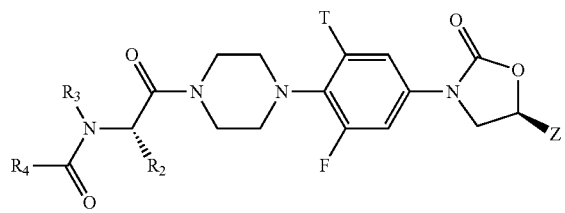

| S. No. | R⁴ | R² | R³ | T | Z | ESIMS |
|---|---|---|---|---|---|---|
| 91 | [1,2,3-triazolylmethyl] | —H | —H | —F | [CH₂NHC(O)OCH₃] | 536.4 (M − 1) |
| 92 | [pyrazinyl] | —H | —H | —F | [CH₂NHC(O)OEt] | 586.3 (M + 39)<br>570.4 (M + 23)<br>548.2 (M + 1) |
| 93 | [1,2,4-triazol-1-ylmethyl] | —H | —H | —F | [CH₂NHC(O)OCH₃] | 559.9 (M + 23)<br>538.0 (M + 1) |
| 94 | [thiazol-4-yl] | —H | —H | —F | [CH₂NHC(O)OCH₃] | 561.9 (M + 23)<br>539.9 (M + 1) |
| 95 | [pyridin-3-yl] | —H | —H | —H | [CH₂NHC(O)OCH₃] | 537.9 (M + 23)<br>515.9 (M + 1) |
| 96 | [pyridin-3-yl] | —H | —H | —F | [CH₂NHC(O)OEt] | 585.4 (M + 39)<br>569.1 (M + 23)<br>547.4 (M + 1) |
| 97 | [2,3-dihydrobenzo[1,4]dioxin-6-yl] | —H | —H | —F | [CH₂NHC(O)OCH₃] | 628.9 (M + 39)<br>613.1 (M + 23)<br>590.9 (M + 1) |
| 98 | [5-cyclopropylisoxazol-3-yl] | —H | —H | —F | [CH₂NHC(O)OCH₃] | 601.9 (M + 39)<br>586.0 (M + 23)<br>564.0 (M + 1) |
| 99 | [isoxazol-5-yl] | —H | —H | —F | [CH₂NHC(O)OCH₃] | 546.0 (M + 23)<br>524.0 (M + 1) |

TABLE 5-continued
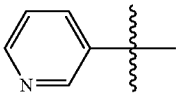
| S. No. | R⁴ | R² | R³ | T | Z | ESIMS |
|---|---|---|---|---|---|---|
| 100 | 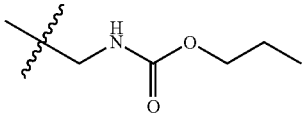 [SMILES: *CNC(=O)OCCC] | —H | —H | —F | 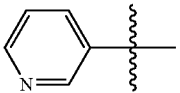 | 560.0 (M − 1) |
| 101 | 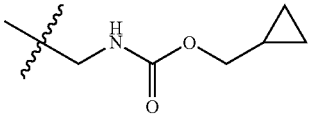 [SMILES: *CNC(=O)OCC1CC1] | —H | —H | —F | 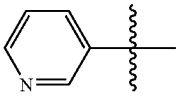 | 596.0 (M + 23)<br>574.0 (M + 1) |
| 102 | 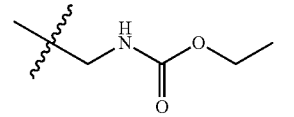 [SMILES: *CNC(=O)OCC] | —H | —H | —F | 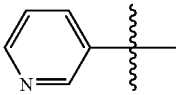 | 570.0 (M + 23)<br>547.8 (M + 1) |
| 103 | 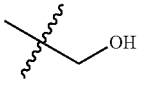 [SMILES: *CO] | —H | —H | —F | 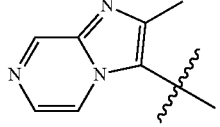 [SMILES: *c1c(C)nc2cnccn12] | 498.7 (M + 23)<br>476.6 (M + 1) |
| 104 | 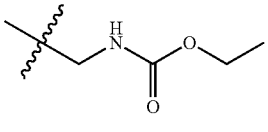 [SMILES: *CNC(=O)OCC] | —H | —H | —F | 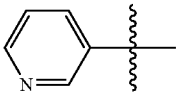 | 624.0 (M + 23)<br>601.9 (M + 1) |
| 105 | 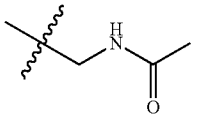 [SMILES: *CNC(C)=O] | —H | —H | —F | 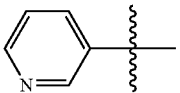 [SMILES: *c1cccnc1] | 540.0 (M + 23)<br>518.0 (M + 1) |
| 106 | 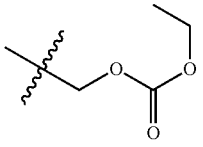 [SMILES: *COC(=O)OCC] | —H | —H | —F | 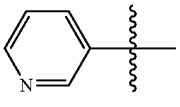 | 570.9 (M + 23)<br>548.8 (M + 1) |
| 107 | 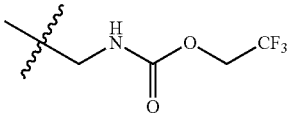 [SMILES: *CNC(=O)OCC(F)(F)F] | —H | —H | —F | 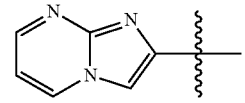 [SMILES: *c1cn2cccnc2n1] | 601.9 (M + 1) |
| 108 | 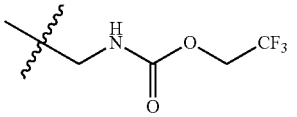 [SMILES: *CNC(=O)OCC(F)(F)F] | —H | —H | —F | 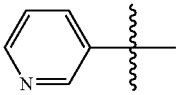 | 680.4 (M + 39)<br>664.0 (M + 23)<br>641.9 (M + 1) |
| 109 | 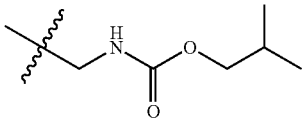 [SMILES: *CNC(=O)OCC(C)C] | —H | —H | —F |  | 598.0 (M + 23)<br>576.0 (M + 1) |

TABLE 5-continued

| S. No. | R⁴ | R² | R³ | T | Z | ESIMS |
|---|---|---|---|---|---|---|
| 110 | pyridin-3-yl | —CH₃ | —H | —F | —CH₂—NH—C(O)—O—ethyl | 600.1 (M + 39)<br>584.0 (M + 23)<br>561.9 (M + 1) |
| 111 | pyridin-3-yl | —H | —H | —F | —CH₂—NH—C(O)—ethyl | 531.0 (M + 1) |
| 112 | pyridin-3-yl | —CH₃ | —H | —F | —CH₂—NH—C(O)—O—ethyl | 581.7 (M + 39)<br>566.0 (M + 23)<br>543.7 (M + 1) |
| 113 | pyridin-3-yl | —CH₃ | —H | —H | —CH₂—NH—C(O)—OCH₃ | 568.0 (M + 39)<br>552.0 (M + 23)<br>529.7 (M + 1) |
| 114 | imidazo[1,2-a]pyrimidin-2-yl | —H | —H | —F | —CH₂—NH—C(O)—O—propyl | 623.9 (M + 23)<br>601.9 (M + 1) |
| 115 | imidazo[1,2-a]pyrimidin-2-yl | —CH₃ | —H | —H | —CH₂—NH—C(O)—OCH₃ | 607.4 (M + 39)<br>591.1 (M + 23)<br>569.0 (M + 1) |
| 116 | pyridin-3-yl | —CH₃ | —H | —F | —CH₂—NH—C(O)—O—propyl | 598.0 (M + 23)<br>576.8 (M + 1) |
| 117 | cyclohexyl | —H | —H | —F | —CH₂—NH—C(O)—OCH₃ | 576.9 (M + 39)<br>561.0 (M + 23)<br>538.7 (M + 1) |
| 118 | 6-chloropyridin-3-yl | —H | —H | —F | —CH₂—NH—C(O)—OCH₃ | 567.8 (M + 1) |
| 119 | imidazo[1,2-a]pyrimidin-2-yl | —CH₃ | —H | —H | —CH₂—NH—C(O)—O—ethyl | 606.0 (M + 23)<br>583.9 (M + 1) |

TABLE 5-continued
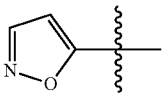 [SMILES: *c1ccno1]
| S. No. | R⁴ | R² | R³ | T | Z | ESIMS |
|---|---|---|---|---|---|---|
| 120 | 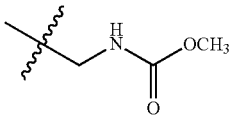 [SMILES: *CNC(=O)OC] | —H | —H | —H | 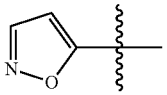 [SMILES: *c1ccno1] | 527.9 (M + 23)<br>505.6 (M + 1) |
| 121 | 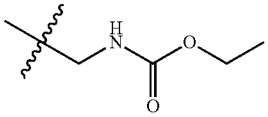 [SMILES: *CNC(=O)OCC] | —H | —H | —F | 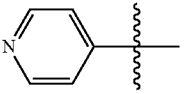 | 559.8 (M + 23)<br>538.0 (M + 1) |
| 122 | 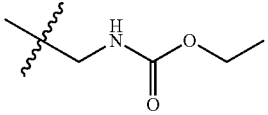 [SMILES: *CNC(=O)OCC] | —H | —H | —F | 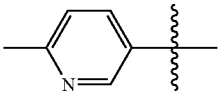 | 585.9 (M + 39)<br>569.8 (M + 23)<br>547.6 (M + 1) |
| 123 | 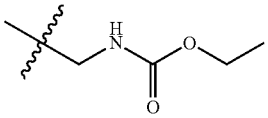 | —H | —H | —F | 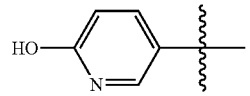 | 599.9 (M + 39)<br>584.0 (M + 23)<br>561.6 (M + 1) |
| 124 | 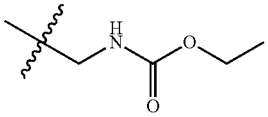 [SMILES: *CNC(=O)OCC] | —H | —H | —F | 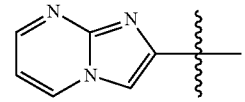 [SMILES: *c1cn2cccnc2n1] | 585.9 (M + 23)<br>563.9 (M + 1) |
| 125 | 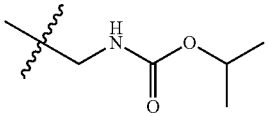 [SMILES: *CNC(=O)OC(C)C] | —H | —H | —F | 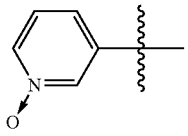 [SMILES: *c1ccc[n+]([O-])c1] | 624.1 (M + 23)<br>601.9 (M + 1) |
| 126 | 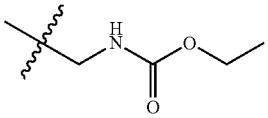 | —H | —H | —F | 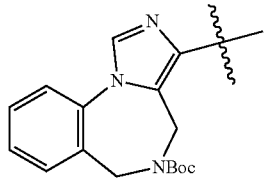 [SMILES: *c1ncn2c1CN(C(=O)OC(C)(C)C)Cc1ccccc1-2] | 601.8 (M + 39)<br>585.8 (M + 23)<br>563.6 (M + 1) |
| 127 | 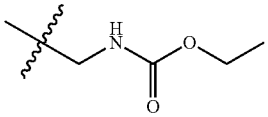 [SMILES: *CNC(=O)OCC] | —H | —H | —F | 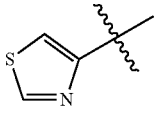 [SMILES: *c1cscn1] | 753.7 (M + 1) |
| 128 | 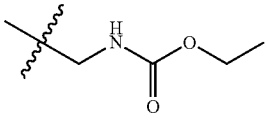 [SMILES: *CNC(=O)OCC] | —H | —H | —F |  | 591.7 (M + 39)<br>575.8 (M + 23)<br>553.7 (M + 1) |

TABLE 5-continued

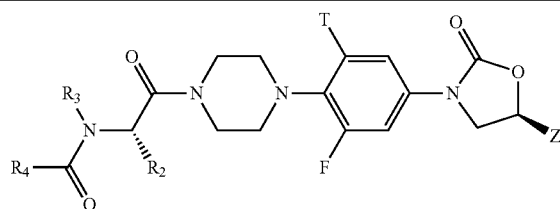

| S. No. | R⁴ | R² | R³ | T | Z | ESIMS |
|---|---|---|---|---|---|---|
| 129 | 1H-pyrrol-2-yl | —H | —H | —F | ethyl carbamate-CH₂- | 558.0 (M + 23)<br>535.8 (M + 1) |
| 130 | thiazol-5-yl | —CH₃ | —H | —F | ethyl carbamate-CH₂- | 605.8 (M + 39)<br>590.0 (M + 23)<br>567.7 (M + 1) |
| 131 | isoxazol-5-yl | —CH₃ | —H | —F | ethyl carbamate-CH₂- | 590.0 (M + 39)<br>574.1 (M + 23)<br>551.7 (M + 1) |
| 132 | imidazo[1,2-a]pyrimidin-2-yl | —CH₂OH | —H | —F | ethyl carbamate-CH₂- | 656.0 (M + 39)<br>640.0 (M + 23)<br>617.9 (M + 1) |
| 133 | imidazo[1,2-a]pyridin-2-yl | —H | —H | —F | ethyl carbamate-CH₂- | 624.8 (M + 39)<br>609.0 (M + 23)<br>587.0 (M + 1) |
| 134 | 6-chloropyridin-3-yl | —H | —H | —F | ethyl carbamate-CH₂- | 604.1 (M + 23)<br>582.0 (M + 1) |
| 135 | benzofuran-2-yl | —H | —H | —F | ethyl carbamate-CH₂- | 609.0 (M + 23)<br>586.9 (M + 1) |
| 136 | thiazol-4-yl | —CH₃ | —H | —F | methyl carbamate-CH₂- | 576.0 (M + 23)<br>554.0 (M + 1) |
| 137 | imidazo[1,2-a]pyrimidin-2-yl | —CH₃ | —H | —F | methyl carbamate-CH₂- | 587.4 (M + 1) |
| 138 | isoxazol-5-yl | —CH₃ | —H | —F | methyl carbamate-CH₂- | 575.7 (M + 39)<br>560.0 (M + 23)<br>537.9 (M + 1) |

TABLE 5-continued
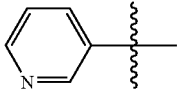
| S. No. | R⁴ | R² | R³ | T | Z | ESIMS |
|---|---|---|---|---|---|---|
| 139 | 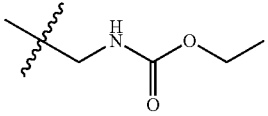 [SMILES: *CNC(=O)OCC] | —H | —H | —H | 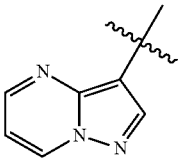 [SMILES: *c1cnn2cccnc12] | 567.7 (M + 39)<br>551.9 (M + 23)<br>529.4 (M + 1) |
| 140 | 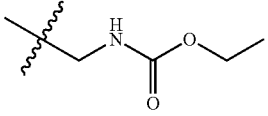 | —H | —H | —F | 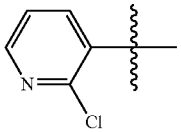 | 626.1 (M + 39)<br>610.0 (M + 23)<br>587.9 (M + 1) |
| 141 | 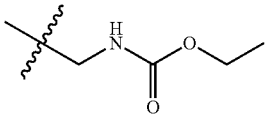 | —H | —H | —F | 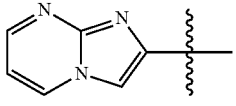 [SMILES: *c1cn2cccnc2n1] | 604.1 (M + 23)<br>582.0 (M + 1) |
| 142 | 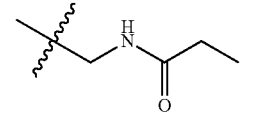 [SMILES: *CNC(=O)CC] | —H | —H | —F | 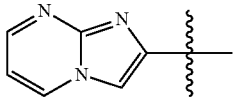 [SMILES: *c1cn2cccnc2n1] | 610.0 (M + 39)<br>594.1 (M + 23)<br>572.0 (M + 1) |
| 143 | 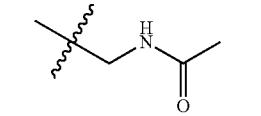 [SMILES: *CNC(C)=O] | —CH₃ | —H | —F | 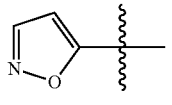 [SMILES: *c1ccno1] | 593.9 (M + 23)<br>572.0 (M + 1) |
| 144 | 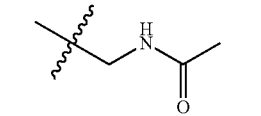 [SMILES: *CNC(C)=O] | —CH₃ | —H | —F | 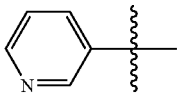 | 543.8 (M + 23)<br>521.8 (M + 1) |
| 145 | 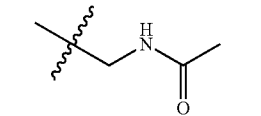 [SMILES: *CNC(C)=O] | —CH₃ | —H | —F | 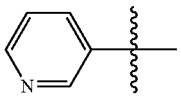 | 553.9 (M + 23)<br>532.0 (M + 1) |
| 146 | 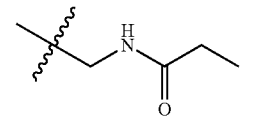 [SMILES: *CNC(=O)CC] | —CH₃ | —H | —F | 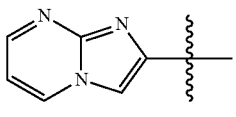 [SMILES: *c1cn2cccnc2n1] | 568.1 (M + 23)<br>545.7 (M + 1) |
| 147 | 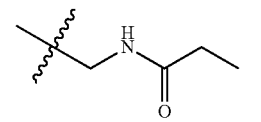 [SMILES: *CNC(=O)CC] | —CH₃ | —H | —F | | 583.9 (M − 1) |

TABLE 5-continued

| S. No. | R⁴ | R² | R³ | T | Z | ESIMS |
|---|---|---|---|---|---|---|
| 148 | pyrazolo[1,5-a]pyrimidin-3-yl | —CH₃ | —H | —F | —CH₂NHC(O)OCH₃ | 626.1 (M + 39)<br>610.2 (M + 23)<br>588.0 (M + 1) |
| 149 | pyridin-3-yl | —CH₂CH(CH₃)₂ | —H | —F | —CH₂NHC(O)OCH₃ | 598.1 (M + 23)<br>576.1 (M + 1) |
| 150 | pyridin-4-yl | —CH₃ | —H | —F | —CH₂NHC(O)OCH₃ | 570.0 (M + 23)<br>548.0 (M + 1) |
| 151 | imidazo[1,2-a]pyrimidin-2-yl | —CH₃ | —H | —F | —CH₂-(1,2,3-triazol-1-yl) | 619.3 (M + 39)<br>603.5 (M + 23)<br>581.4 (M + 1) |
| 152 | isoxazol-5-yl | —H | —H | —H | —CH₂NHC(O)OEt | 558.0 (M + 39)<br>542.0 (M + 23)<br>519.8 (M + 1) |
| 153 | isoxazol-5-yl | —CH₃ | —H | —H | —CH₂NHC(O)OEt | 572.0 (M + 39)<br>556.0 (M + 23)<br>533.9 (M + 1) |
| 154 | pyridin-3-yl | —H | —H | —F | —CH₂OC(O)NHEt | 585.3 (M + 39)<br>569.5 (M + 23)<br>547.4 (M + 1) |
| 155 | imidazo[1,2-a]pyrimidin-2-yl | —CH₂CH(CH₃)₂ | —H | —F | —CH₂NHC(O)OCH₃ | 668.0 (M + 39)<br>652.0 (M + 23)<br>629.9 (M + 1) |
| 156 | pyridin-3-yl | —CH₂CH(CH₃)₂ | —H | —F | —CH₂NHC(O)OCH₃ | 628.1 (M + 39)<br>612.1 (M + 23)<br>589.9 (M + 1) |

TABLE 5-continued

| S. No. | R⁴ | R² | R³ | T | Z | ESIMS |
|---|---|---|---|---|---|---|
| 157 | isoxazol-5-yl (methylene) | —CH(CH₃)₂ | —H | —F | —CH₂NHC(O)CH₃ | 572.1 (M + 23)<br>550.1 (M + 1) |
| 158 | pyridazin-3-yl (methylene) | —CH(CH₃)₂ | —H | —F | —CH₂-(1,2,3-triazol-1-yl) | 570.1 (M + 1) |
| 159 | pyridin-3-yl (methylene) | —C(CH₃)₃ | —H | —F | —CH₂NHC(O)OCH₃ | 628.2 (M + 39)<br>612.0 (M + 23)<br>590.0 (M + 1) |
| 160 | imidazo[1,2-a]pyrimidin-2-yl (methylene) | —C(CH₃)₃ | —H | —F | —CH₂NHC(O)OCH₃ | 668.0 (M + 39)<br>652.0 (M + 23)<br>630.1 (M + 1) |
| 161 | pyridin-3-yl (methylene) | —CH₃ | —H | —F | —CH₂-(4-(hydroxymethyl)-1,2,3-triazol-1-yl) | 594.0 (M + 23)<br>572.1 (M + 1) |
| 162 | HOCH₂C(CH₃)₂– | —H | —H | —F | —CH₂NHC(O)OCH₃ | 508.8 (M + 23)<br>486.7 (M + 1) |
| 163 | phenyl (methylene) | —H | —H | —F | —CH₂NHC(O)OCH₃ | 555.0 (M + 23)<br>532.8 (M + 1) |
| 164 | imidazo[1,2-a]pyrimidin-2-yl (methylene) | —CH₃ | —H | —F | —CH₂NHC(O)-isoxazol-5-yl | 646.3 (M + 23)<br>624.4 (M + 1) |
| 165 | pyridin-3-yl (methylene) | —CH₃ | —H | —F | —CH₂NHC(O)-isoxazol-5-yl | 583.7 (M + 1) |
| 166 | imidazo[1,2-a]pyrimidin-2-yl (methylene) | —CH(CH₃)₂ | —H | —F | —CH₂NHC(O)OCH₂CH₃ | 652.1 (M + 23)<br>613.1 (M + 1) |

TABLE 5-continued

| S. No. | R⁴ | R² | R³ | T | Z | ESIMS |
|---|---|---|---|---|---|---|
| 167 | pyridin-3-yl | —CH(CH₃)₂ | —H | —F | CH₂NHC(O)OEt | 612.0 (M + 23)<br>590.1 (M + 1) |
| 168 | pyridin-3-yl N-oxide | —CH₃ | —H | —F | CH₂NHC(O)OCH₃ | 562.0 (M − 1) |
| 169 | 6-fluoropyridin-3-yl | —CH₃ | —H | —F | CH₂NHC(O)OCH₃ | 588.0 (M + 23)<br>566.0 (M + 1) |
| 170 | 2-fluoropyridin-3-yl | —CH₃ | —H | —F | CH₂NHC(O)OCH₃ | 588.0 (M + 23)<br>566.0 (M + 1) |
| 171 | pyrazin-2-yl | —CH₃ | —H | —F | CH₂NHC(O)OCH₃ | 571.0 (M + 23)<br>549.0 (M + 1) |
| 172 | pyridin-2-yl | —CH₃ | —H | —F | CH₂NHC(O)OCH₃ | 570.0 (M + 23)<br>548.0 (M + 1) |
| 173 | 6-methylpyridin-3-yl | —CH₃ | —H | —F | CH₂NHC(O)OCH₃ | 584.1 (M + 23)<br>561.9 (M + 1) |
| 174 | 6-hydroxypyridin-3-yl | —CH₃ | —H | —F | CH₂NHC(O)OCH₃ | 561.9 (M − 1) |
| 175 | 5-cyclopropylisoxazol-3-yl | —CH₃ | —H | —F | CH₂NHC(O)OCH₃ | 600.0 (M + 23)<br>577.9 (M + 1) |

TABLE 5-continued

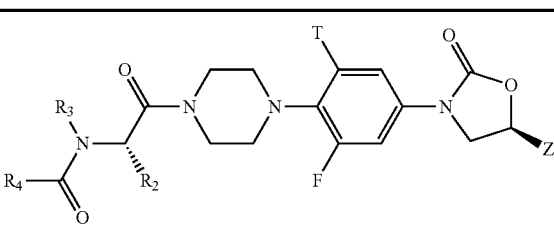

| S. No. | R⁴ | R² | R³ | T | Z | ESIMS |
|---|---|---|---|---|---|---|
| 176 | 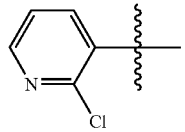 [SMILES: *c1cccnc1Cl] 2-chloropyridin-3-yl | —CH₃ | —H | —F | 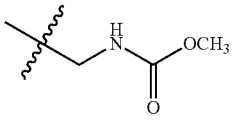 [SMILES: *CNC(=O)OC] methyl carbamate CH₂ | 604.0 (M + 23) 581.9 (M + 1) |
| 177 | 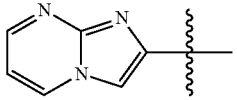 [SMILES: *c1cn2cccnc2n1] imidazo[1,2-a]pyrimidin-2-yl | —CH₃ | —H | —F | 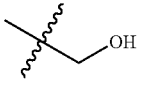 [SMILES: *CO] CH₂OH | 552.4 (M + 23) 530.1 (M + 1) |
| 178 | 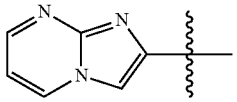 [SMILES: *c1cn2cccnc2n1] imidazo[1,2-a]pyrimidin-2-yl | —CH₃ | —H | —F | 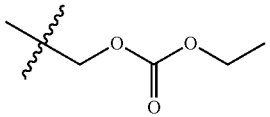 [SMILES: *COC(=O)OCC] ethyl carbonate CH₂ | 625.0 (M + 23) 603.0 (M + 1) |
| 179 | 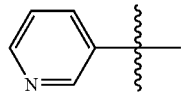 pyridin-3-yl | —CH₃ | —H | —F | 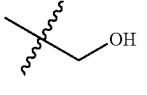 CH₂OH | 513.0 (M + 23) 490.9 (M + 1) |
| 180 | 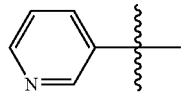 [SMILES: *c1cccnc1] pyridin-3-yl | —CH₃ | —H | —F | 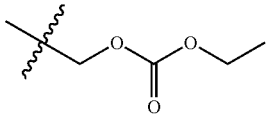 [SMILES: *COC(=O)OCC] ethyl carbonate CH₂ | 585.0 (M + 23) 563.0 (M + 1) |
| 181 | 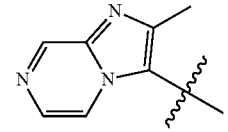 2-methylimidazo[1,2-a]pyrazin-3-yl | —CH₃ | —H | —F | 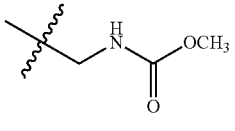 [SMILES: *CNC(=O)OC] methyl carbamate CH₂ | 640.0 (M + 39) 623.9 (M + 23) 601.8 (M + 1) |
| 182 | 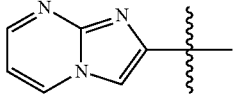 [SMILES: *c1cn2cccnc2n1] imidazo[1,2-a]pyrimidin-2-yl | —CH₃ | —H | —F | 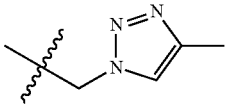 [SMILES: *Cn1cc(C)nn1] 4-methyl-1,2,3-triazol-1-yl-methyl | 617.9 (M + 23) 595.7 (M + 1) |
| 183 | 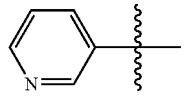 pyridin-3-yl | —CH₃ | —H | —F | 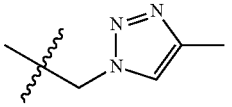 [SMILES: *Cn1cc(C)nn1] 4-methyl-1,2,3-triazol-1-yl-methyl | 577.9 (M + 23) 555.5 (M + 1) |
| 184 | 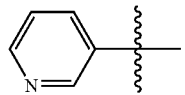 [SMILES: *c1cccnc1] pyridin-3-yl | —CH₃ | —H | —F | 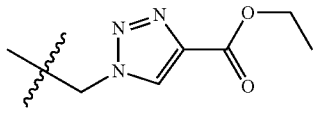 [SMILES: *Cn1cc(C(=O)OCC)nn1] ethyl 1,2,3-triazole-4-carboxylate | 636.1 (M + 23) 613.9 (M + 1) |
| 185 | 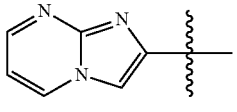 [SMILES: *c1cn2cccnc2n1] imidazo[1,2-a]pyrimidin-2-yl | —CH₃ | —H | —F | 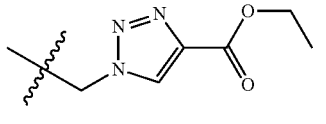 ethyl 1,2,3-triazole-4-carboxylate | 654.0 (M + 1) |

TABLE 5-continued

| S. No. | R⁴ | R² | R³ | T | Z | ESIMS |
|---|---|---|---|---|---|---|
| 186 | isoxazol-5-yl | —CH₃ | —H | —F | CH₂-(1,2,3-triazol-1-yl) (with methyl) | 569.8 (M + 39)<br>553.9 (M + 23)<br>531.8 (M + 1) |
| 187 | pyrimidin-2-yl | —CH₃ | —H | —F | CH₂-(1,2,3-triazol-1-yl) (with methyl) | 564.0 (M + 23)<br>541.6 (M + 1) |
| 188 | imidazo[1,2-a]pyrimidin-2-yl | —CH(CH₃)C₂H₅ | —H | —F | CH₂-NHC(O)OCH₃ (with methyl) | 652.0 (M + 23)<br>629.9 (M + 1) |

TABLE 6

| S. No. | Compound | ESIMS |
|---|---|---|
| 1 | imidazo[1,2-a]pyrazine-2-carboxamide linked via -NH-CH₂CH₂-C(O)- to piperazine-phenyl(F)-oxazolidinone-CH₂-NHC(O)OCH₃ | 607.4 (M + 39)<br>591.4 (M + 23)<br>569.5 (M + 1) |
| 2 | imidazo[1,2-a]pyrazine-2-carboxamide linked via -NH-CH₂-C(O)- to homopiperazine-phenyl(F)-oxazolidinone-CH₂-NHC(O)OCH₃ | 610.0 (M + 23)<br>588.0 (M + 1) |
| 3 | imidazo[1,2-a]pyrazine-2-carboxamide linked via -NH-CH₂-C(O)- to homopiperazine-phenyl(2,6-diF)-oxazolidinone-CH₂-NHC(O)OCH₃ | 610.0 (M + 23)<br>587.9 (M + 1) |

TABLE 6-continued

| S. No. | Compound | ESIMS |
|---|---|---|
| 4 | | 610.0 (M + 23)<br>587.9 (M + 1) |
| 5 | | 625.9 (M + 39)<br>610.0 (M + 23)<br>587.9 (M + 1) |
| 6 | | 623.9 (M + 23)<br>601.8 (M + 1) |
| 7 | | 584.0 (M + 23)<br>562.0 (M + 1) |
| 8 | | 600.1 (M + 39)<br>584.0 (M + 23)<br>561.7 (M + 1) |
| 9 | | 640.1 (M + 39)<br>623.9 (M + 23)<br>602.0 (M + 1) |
| 10 | | 569.9 (M + 23)<br>547.7 (M + 1) |

TABLE 6-continued

| S. No. | Compound | ESIMS |
|---|---|---|
| 11 | | 547.5 (M + 1) |
| 12 | | 610.2 (M + 23)<br>588.0 (M + 1) |

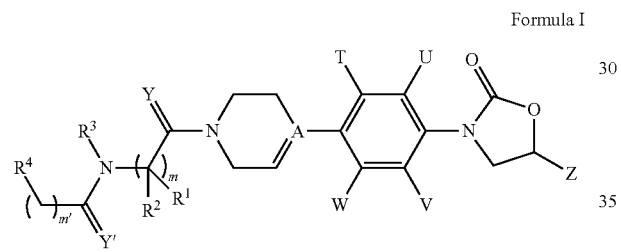

The invention claimed is:
1. A compound of Formula I,

Formula I its tautomeric forms, stereoisomers polymorphs, salts or solvates thereof, wherein:
'---' is independently a single bond or absent;
when '---' is a single bond, 'A' represents carbon atom and when '---' is absent, 'A' is CH or N;
Y and Y' are same or different and independently represent O or S;
$R^1$ and $R^2$ are same or different and independently represent hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{1}$-$C_{12}$alkoxy, $C_{1-12}$ haloalkoxy, $C_1$-$C_6$alkoxyC$_1$-$C_6$alkyl, $C_1$-$C_6$alkoxyC$_1$-$C_6$alkoxyC$_1$C$_3$alkyl, $C_{3-20}$cycloalkyl, heterocyclyl, aryl, heteroaryl, —(CH$_2$)$_n$-cycloalkyl, —(CH$_2$)$_n$-heterocyclyl, —(CH$_2$)$_n$-aryl, —(CH$_2$)$_n$-heteroaryl, —(CH$_2$)$_n$C(=Y)NR$^5$R$^6$, —(CH$_2$)$_n$C(=Y)OR$^5$, —(CH$_2$)$_n$NR$^5$R$^6$, —(CH$_2$)$_n$OC(=Y)R$^5$, —(CH$_2$)$_n$OC(=Y)OR$^5$, —(CH$_2$)$_n$OC(=Y)NR$^5$R$^6$, —(CH$_2$)$_n$N(R$^5$)C(=Y)OR$^6$, —(CH$_2$)$_n$N(R$^5$)C(=Y)NR$^5$R$^6$, —(CH$_2$)$_n$NR$^5$C(=Y)R$^6$, —(CH$_2$)$_n$C(=Y)R$^5$, —(CH$_2$)$_n$YR$^5$ wherein each methylene group may be substituted by one or more halogen atoms), —C(=Y)NR$^5$R$^6$, —OC(=Y)R$^5$, —OC(=Y)NR$^5$R$^6$, —C(=Y)OR$^5$, —OR$^5$, —OC(=Y)OR$^5$, —SR$^5$, —NO$_2$, —NR$^5$R$^6$, —N(R$^5$)C(=Y)R$^6$, —N(R$^5$)—C(=Y)OR$^6$, or —N(R$^5$)C(=Y)NR$^5$R$^6$, each of which may be optionally substituted at any available position by one or more substituents R$^a$; or
$R^1$ and $R^2$ can together with the carbon atom to which they are attached form a 3 to 10 membered monocyclic ring, partially unsaturated or saturated, which may contain from one to three heteroatoms independently selected from O, S or N; the ring thus formed may be fused with one or two rings independently selected from the group comprising an aryl ring, a cycloalkyl ring, a heterocyclyl ring or monocyclic heteroaryl ring; the ring thus formed can be optionally substituted at any available position by one or more substituents R$^a$;
$R^3$ represents hydrogen, $C_{1-12}$ alkyl, $C_{2-12}$alkenyl, $C_{2-12}$ alkynyl, $C_{1-12}$ haloalkyl, $C_{2-12}$ haloalkenyl, $C_{2-12}$ haloalkynyl, $C_1$-$C_6$alkoxyC$_1$-$C_6$alkyl, $C_1$-$C_6$alkoxyC$_1$-$C_6$alkoxyC$_1$-$C_3$alkyl, $C_{3-20}$cycloalkyl, heterocyclyl, aryl, heteroaryl, —(CH$_2$)$_n$-cycloalkyl, —(CH$_2$)$_n$-heterocyclyl, —(CH$_2$)$_n$-aryl, —(CH$_2$)$_n$-heteroaryl, —(CH$_2$)$_n$YR$^5$, —(CH$_2$)$_n$C(=Y)R$^5$, —(CH$_2$)$_n$NR$^5$R$^6$, —(CH$_2$)$_n$C(=Y)NR$^5$R$^6$, —(CH$_2$)$_n$C(=Y)OR$^5$, —(CH$_2$)$_n$OC(=Y)R$^5$, —(CH$_2$)$_n$OC(=Y)OR$^5$, —(CH$_2$)$_n$NR$^5$C(=Y)R$^6$, —(CH$_2$)$_n$N(R$^5$)C(=Y)OR$^6$, —(CH$_2$)$_n$N(R$^5$)C(=Y)NR$^5$R$^6$, —(CH$_2$)$_n$OC(=Y)NR$^5$R$^6$, or —(CH$_2$)$_n$N(R$^5$)C(=Y)NR$^5$R$^6$, (wherein each methylene group may be substituted by one or more halogen atoms), each of which may be optionally substituted at any available position by one or more substituents R$^a$;
$R^4$ represents aryl, heteroaryl, or —C(=Y)R$^5$, each of which may be optionally substituted at any available position by one or more substituents R$^a$;
with the proviso that when m is equal to 2 or 3, then $R^4$ cannot be phenyl substituted with substituents selected from —OH, —OC$_{1-4}$alkyl, —NH$_2$, aminoacyl, —CH$_2$—NH$_2$ and aminoacylalkyl;
Z represents $C_{1-12}$alkyl, $C_{2-12}$alkenyl, $C_{2-12}$ alkynyl, $C_{2-12}$ haloalkenyl, $C_{2-12}$ haloalkynyl, $C_{1-12}$ haloalkoxy, $C_1$-$C_6$alkoxyC$_1$-$C_6$alkoxyC$_1$-$C_3$alkyl, —$C_{3-20}$cycloalkyl, heterocyclyl, aryl, heteroaryl, —(CH$_2$)$_n$-cycloalkyl, —(CH$_2$)$_n$-heterocyclyl, —(CH$_2$)$_n$-aryl, —(CH$_2$)$_n$-heteroaryl, —(CH$_2$)$_n$—NCS, —C(=Y)R$^5$, —C(=Y)OR$^6$, —C(=Y)NR$^5$R$^6$, —OC(=Y)OR$^5$, —(CH$_2$)$_n$OP(=O)R$^5$R$^6$, —(CH$_2$)$_n$NHP(=O)R$^5$R$^6$, —(CH$_2$)$_n$OC(=Y)OR$^5$, —(CH$_2$)$_n$C(=Y)R$^5$, —(CH$_2$)$_n$C(=Y)NR$^5$R$^6$, or —(CH$_2$)$_n$C(=Y)OR$^5$, each of which may be optionally substituted at any available position by one or more substituents R$^a$;

T, U, V and W are same or different and independently represent hydrogen or halogen;

$R^5$ and $R^6$ are same or different and are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-8}$ cycloalkyl, heterocyclyl, aryl, heteroaryl, aryloxy, —$(CH_2)_n$-cycloalkyl, —$(CH_2)_n$-heterocyclyl, —$(CH_2)_n$-aryl, —$(CH_2)_n$-heteroaryl, each of which may be optionally substituted at any available position with halogen, hydroxyl, $C_{1-12}$ alkyl, $C_{2-12}$ alkenyl, $C_{2-12}$ alkynyl, $C_{1-12}$ alkoxy, $C_{1-12}$ alkylcarbonyl, $C_{1-12}$ alkoxycarbonyl, $C_{3-8}$ cycloalkyl, $C_{1-12}$ haloalkyl, $C_{1-12}$ haloalkoxy, $C_{2-12}$ haloalkenyl, aryl, heterocyclyl, heteroaryl, —$(CH_2)_n$-aryl, —$(CH_2)_n$-heterocyclyl, —$(CH_2)_n$-heteroaryl, —$(CH_2)_n$-cycloalkyl, —CN, —$OR^7$, —$NO_2$, —$NR^7R^8$, —$N(R^7)C(=Y)R^8$, —$N(R^7)C(=Y)OR^8$, —$N(R^7)C(=Y)NR^7R^8$, —$C(=Y)R^7$, —$C(=Y)NR^7R^8$, —$OC(=Y)R^7$, —$OC(=Y)NR^7R^8$, —$C(=Y)OR^7$, —$OC(=Y)OR^7$, —$SR^7$, —$S(O)_dR^7$, —$SO_2NR^7R^8$, —$NR^7SO_2R^8$, —$OP(=O)R^7R^8$, —$NHP(=O)R^7R^8$, or —$P(=O)R^7R^8$; or $R^5$ and $R^6$ may be joined together along with the heteroatom to which they are joined to form a heterocyclic or heteroaryl ring which may additionally contain from one to three heteroatoms independently selected from O, S or N, the ring formed may optionally be substituted with one or more substituents selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_1$-$C_6$alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-8}$ cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, -$C_{1-12}$ alkylcarbonyl, -$C_{1-12}$ alkoxycarbonyl, —CN, —CF), —$OCF_3$ —$CH_2CF_3$; —$CF_2CF_3$, —$NO_2$, —$NR^7R^8$, —$N(R^7)C(=Y)R^8$, —$N(R^7)C(=Y)OR^8$, —$N(R^7)C(=Y)NR^7R^8$, —$C(=Y)R^7$, —$C(=Y)NR^7R^8$, —$OC(=Y)R^7$, —$OC(=Y)NR^7R^8$, —$OC(=Y)R^7$, —$C(=Y)OR^7$, —$SR^7$, —$S(O)_dR^7$, —$SO_2NR^7R^8$; —$NR^7SO_2R^8$, —$OP(=O)R^7R^8$, —$NHP(=O)R^7R^8$, or —$P(O)R^7R^8$; the ring thus formed may further be fused with 3 to 7 membered unsaturated or saturated ring, which may contain from one to three heteroatoms independently selected from O, S or N, the fused ring may optionally be substituted at any available position by one or more substituents $R^a$;

$R^a$ is independently selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, oxo, $C_{1-12}$ alkoxy, $C_1$-$C_6$alkoxy$C_1$-$C_6$ alkyl, $C_1$-$C_6$alkoxy$C_1$-$C_6$alkoxy$C_1$-$C_3$alkyl, $C_{1-12}$ haloalkoxy, $C_{3-8}$ cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, —$C_{1-12}$ alkylcarbonyl, —$C_{1-12}$ alkoxycarbonyl, —CN, —$YR^7$, —$(CH_2)_nYR^7$, —$NO_2$, =$NOR^7$, —$NR^7R^8$, —$N(R^7)C(=Y)R^8$, —$N(R^7)C(=Y)OR^8$, —$N(R^7)C(=Y)NR^7R^8$, —$C(=Y)R^7$, —$C(=Y)NR^7R^8$, —$OC(=Y)R^7$, —$OC(=Y)NR^7R^8$, —$C(=Y)OR^7$, —$OC(=Y)OR^7$, —$SR^7$, —$S(O)_dR^7$, —$SO_2NR^7R^8$, —$OP(=O)R^7R^8$, —$NHP(=O)R^7R^8$, —$P(O)R^7R^8$, —$(CH_2)_nCN$, —$YR^7$, —$(CH_2)_nYR^7$, —$NO_2$, =$NOR^7$, —$(CH_2)_nNR^7R^8$, —$(CH_2)_nN(R^7)C(=Y)R^8$, —$(CH_2)_nN(R^7)C(=Y)OR^8$, —$(CH_2)_nN(R^7)C(=Y)NR^7R^8$, —$(CH_2)_nC(=Y)R^7$, —$(CH_2)_nC(=Y)NR^7R^8$, —$(CH_2)_nOC(=Y)R^7$, —$(CH_2)_nOC(=Y)NR^7R^8$, —$(CH_2)_nC(=Y)OR^7$, —$(CH_2)_nOC(=Y)OR^7$, —$(CH_2)_nSR^7$, —$(CH_2)_nS(O)_dR^7$, —$(CH_2)_nSO_2NR^7R^8$, —$(CH_2)_nOP(=O)R^7R^8$, $(CH_2)_nNHP(=O)R^7R^8$, or —$(CH_2)_nP(O)R^7R^8$; each of which may optionally be substituted at any available position by one or more substituents selected from hydrogen, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, oxo, $C_1$-$C_{12}$ alkoxy, $C_{1-12}$ haloalkoxy, $C_1$-$C_6$alkoxy$C_1$-$C_6$alkyl, $C_1$-$C_6$alkoxy$C_1$-$C_6$alkoxy$C_1$-$C_3$alkyl, $C_{3-8}$ cycloalkyl, heterocyclyl, aryl, heteroaryl, —$(CH_2)_n$-cycloalkyl, —$(CH_2)_n$-heterocyclyl, —$(CH_2)_n$-aryl, —$(CH_2)_n$-heteroaryl, —$C_{1-12}$ alkylcarbonyl, —$C_{1-12}$ alkoxycarbonyl, —CN, —$OR^9$, —$(CH_2)_nOR^9$, —$CF_3$, —$NO_2$, —$NR^9R^{10}$, —$N(R^9)C(=Y)R^{10}$, —$N(R^9)C(=Y)OR^{10}$, —$N(R^9)C(=Y)NR^9R^{10}$, —$C(=Y)R^9$, —$C(=Y)NR^9R^{10}$, —$OC(=Y)R^9$, —$OC(=Y)NR^9R^{10}$, —$OC(=Y)OR^9$, —$C(=Y)OR^9$, —$SR^9$, —$S(O)_dR^9$, —$SO_2NR^9R^{10}$; —$NR^9SO_2R^{10}$, —$OP(=O)R^9R^{10}$, —$NHP(=O)R^9R^{10}$, —$P(O)R^9R^{10}$, —$(CH_2)_nCN$, —$OR^9$, —$(CH_2)_nOR^9$, —$CF_3$, —$NO_2$, —$(CH_2)_nNR^9R^{10}$, —$(CH_2)_nN(R^9)C(=Y)R^{10}$, —$(CH_2)_nN(R^9)C(=Y)OR^{10}$, —$(CH_2)_nN(R^9)C(=Y)NR^9R^{10}$, —$(CH_2)_nC(=Y)R^9$, —$(CH_2)_nC(=Y)NR^9R^{10}$, —$(CH_2)_nOC(=Y)R^9$, —$(CH_2)_nOC(=Y)NR^9R^{10}$, —$(CH_2)_nOC(=Y)OR^9$, —$(CH_2)_nC(=Y)OR^9$, —$(CH_2)_nSR^9$, —$(CH_2)_nS(O)_dR^9$, —$(CH_2)_nSO_2NR^9R^{10}$; —$(CH_2)_nNR^9SO_2R^{10}$, —$(CH_2)_nOP(=O)R^9R^{10}$, $(CH_2)_nNHP(=O)R^9R^{10}$, or —$(CH_2)_nP(O)R^9R^{10}$;

$R^7$ and $R^8$ are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{3-8}$ cycloalkyl, heterocyclyl, aryl, heteroaryl, —$(CH_2)_n$-cycloalkyl, —$(CH_2)_n$-heterocyclyl, —$(CH_2)_n$-aryl, or —$(CH_2)_n$-heteroaryl, each of which may be optionally substituted with halogen, hydroxyl or $C_{1-6}$ alkoxy, or $R^7$ and $R^8$ may be joined together along with the heteroatom to which they are attached to form a heterocyclic or heteroaryl ring which may contain from one to three heteroatoms independently selected from O, S or N, each of which may be optionally substituted with halogen, hydroxyl, $C_{1-6}$ alkyl or $C_{1-6}$ alkoxy; $R^9$ and $R^{10}$ are independently selected from hydrogen, $C_{1-12}$ alkyl, $C_{2-12}$ alkenyl, $C_{2-12}$ alkynyl, $C_{1-12}$ haloalkyl, $C_{2-12}$ haloalkenyl, $C_{3-8}$ cycloalkyl, heterocyclyl, aryl, heteroaryl, —$(CH_2)_n$-cycloalkyl, —$(CH_2)_n$-heterocyclyl, —$(CH_2)_n$-aryl, or —$(CH_2)_n$-heteroaryl, each of which may be optionally substituted with halogen, hydroxyl or $C_{1-6}$ alkoxy, or $R^9$ and $R^{10}$ may be joined together along with the heteroatom to which they are attached to form a heterocyclic or heteroaryl ring which may contain from one to three heteroatoms independently selected from O, S or N, each of which may be optionally substituted with halogen, hydroxyl, $C_{1-6}$ alkyl or $C_{1-6}$ alkoxy;

m is 1, 2, 3 or 4;
m' is 0, 1, 2, 3 or 4;
n is 1, 2, 3 or 4;
d is 1 or 2.

2. The compound according to claim 1 having the Formula Ia, wherein,

Formula Ia

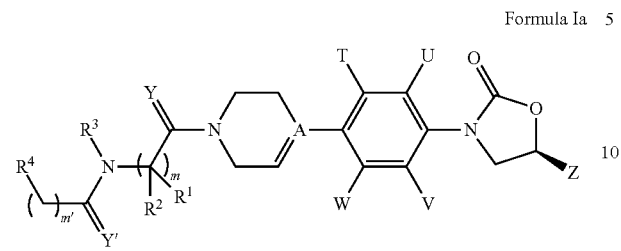

R$^1$, R$^2$, R$^3$, R$^4$, Y, Y', A, T, U, V, W, Z, m and m' are as defined in claim 1; its tautomeric forms, stereoisomers, polymorphs, salts or solvates thereof.

3. The compound according to claim 1 having the Formula Ib, wherein,

Formula Ib

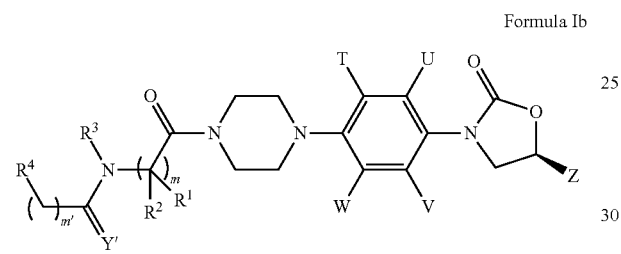

R$^1$, R$^2$, R$^3$, R$^4$, T, U, V, W, Z, m, m' are as defined in claim 1; its tautomeric forms, stereoisomers, polymorphs, salts or solvates thereof.

4. The compound according to claim 1, wherein R$^1$ and R$^2$ are independently selected from hydrogen, C$_{1-12}$ alkyl, C$_{2-12}$ alkenyl, C$_{2-12}$ alkynyl, C$_{3-8}$ cycloalkyl or aryl, each of which may optionally be substituted at any available position by one or more substituents R$^a$ as defined in claim 1 or R$^1$ and R$^2$ together with the carbon atom to which they are attached form a 3 to 10 membered monocyclic ring, partially unsaturated or saturated, which may contain from one to three heteroatoms independently selected from O, S or N, the ring thus formed may be fused with one or two rings independently selected from the group comprising an aryl ring, a cycloalkyl ring, a heterocyclyl ring or monocyclic heteroaryl ring; the ring thus formed is optionally substituted at any available position by one or more substituents R$^a$ as defined in claim 1.

5. The compound according to claim 1, wherein R$^3$ is selected from hydrogen, C$_{1-12}$ alkyl, C$_{2-12}$ alkenyl or C$_{2-12}$ alkynyl, each of which may be optionally substituted at any available position by one or more substituents R$^a$ as defined in claim 1.

6. The compound according to claim 1, wherein R$^4$ is selected from

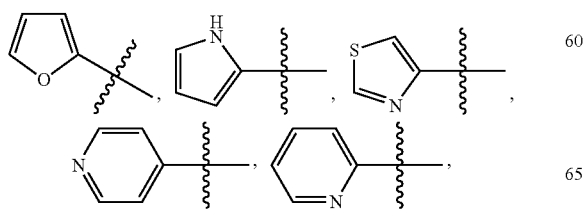

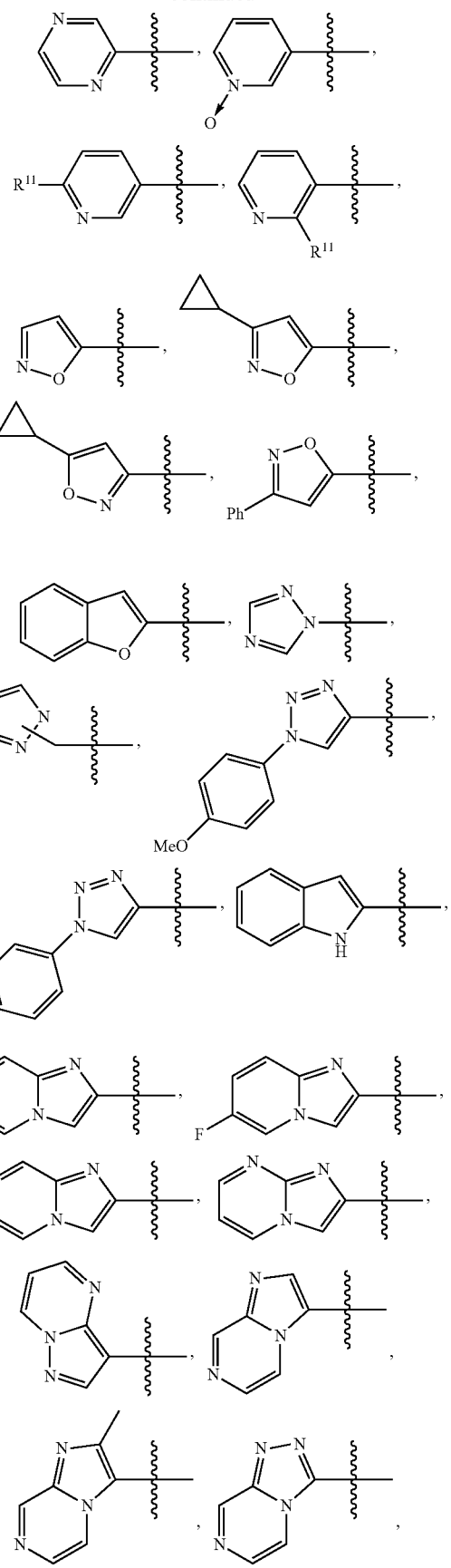

-continued

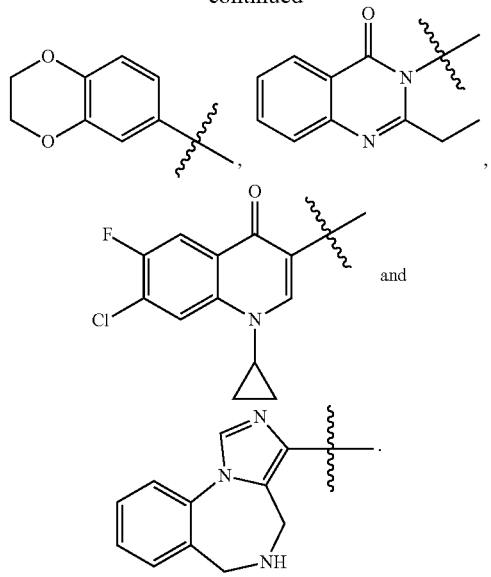

wherein R[11] is selected from —H, —CH₃, —OH, —F,

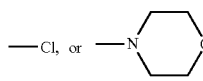

—Cl, or wherein R[12] is selected from —H, —CH₃, —OH, —Cl, or —F.

7. The compound according to claim 1, wherein T and W independently represent fluorine and U and V both represent hydrogen.

8. The compound according to claim 1, wherein m is selected from 1 or 2 and m' is 0.

9. The compound according to claim 1, wherein Z represents —CH₂-triazole, which may be optionally substituted at any available position by one or more substituents R[a] as defined in claim 1.

10. The compound according to claim 9, wherein Z is selected from:

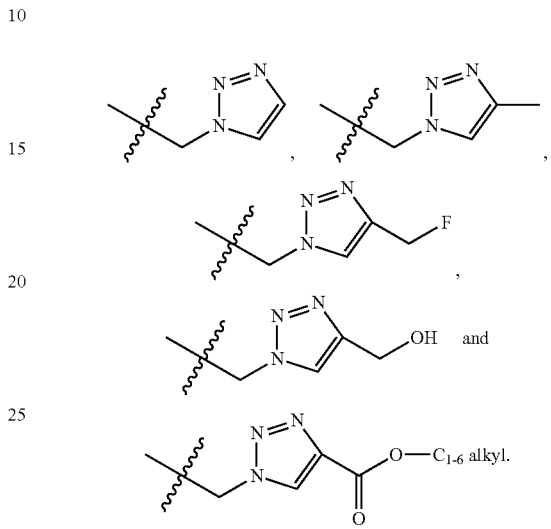

11. A compound which is selected from the group comprising of:

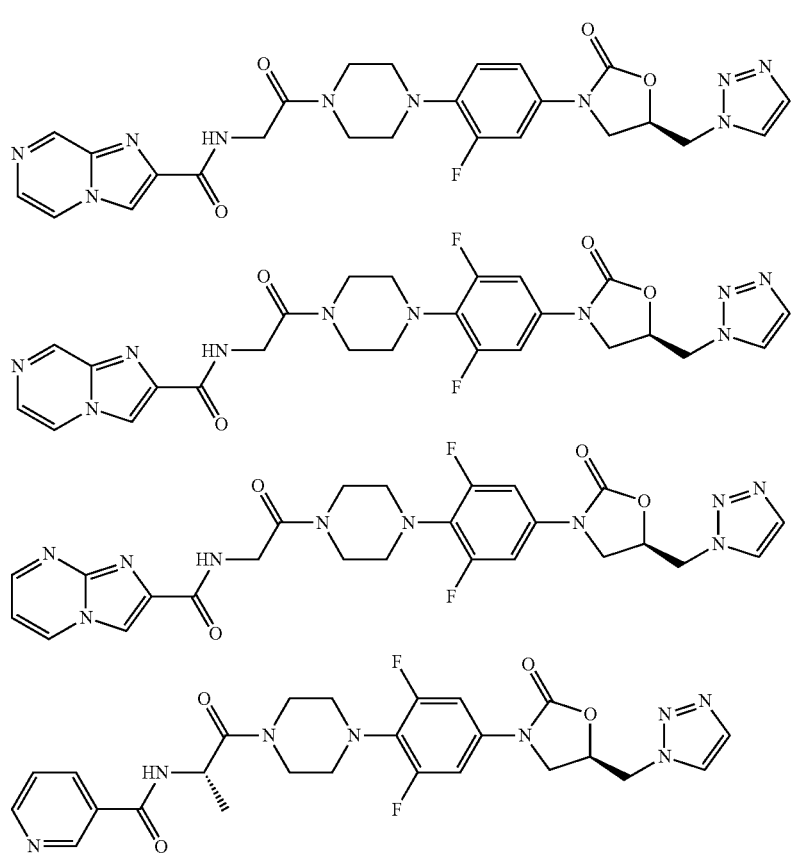

-continued
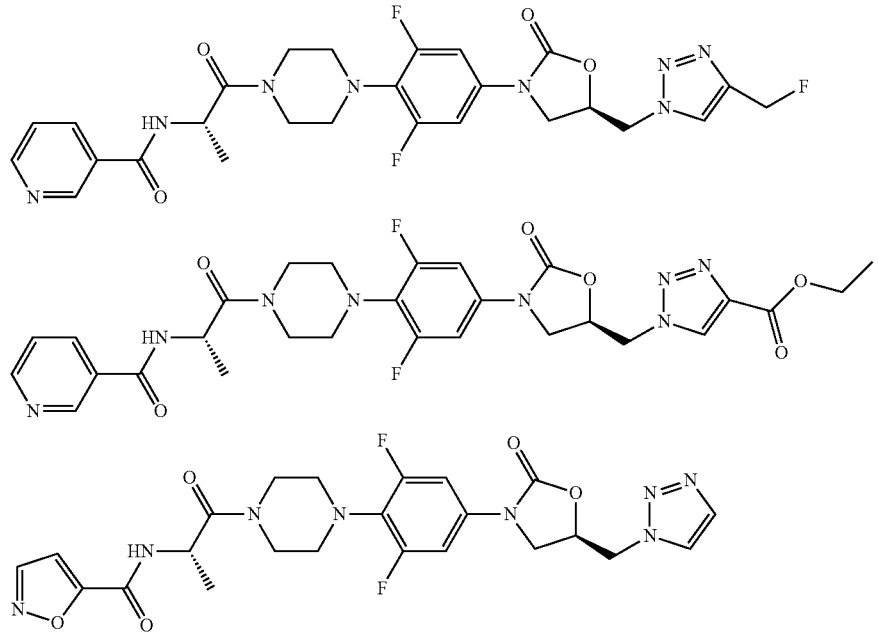
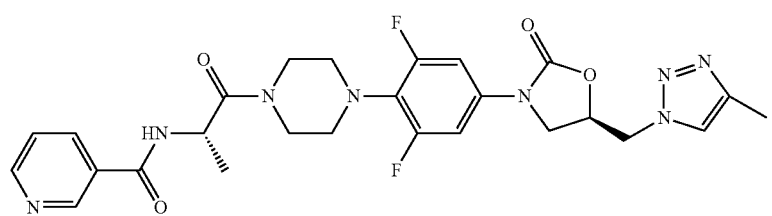
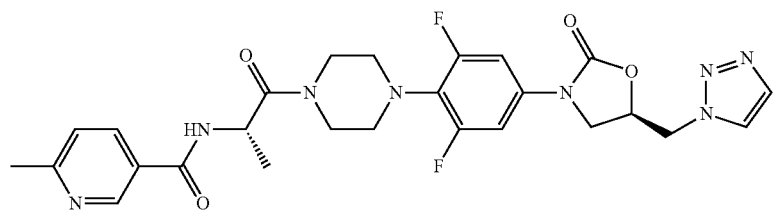
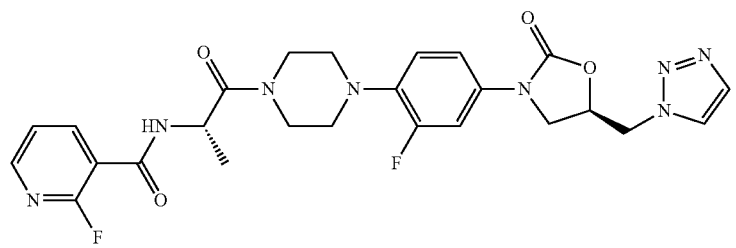
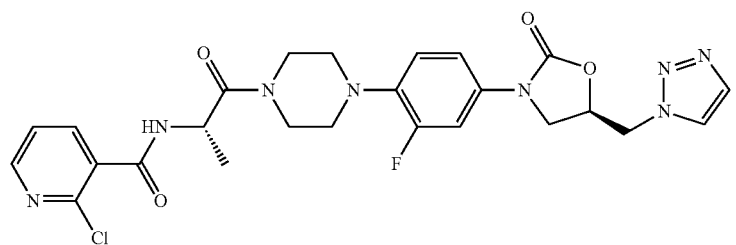

-continued
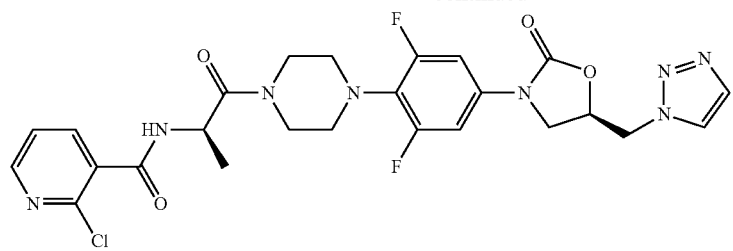
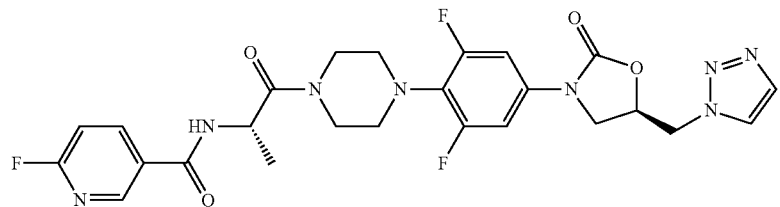
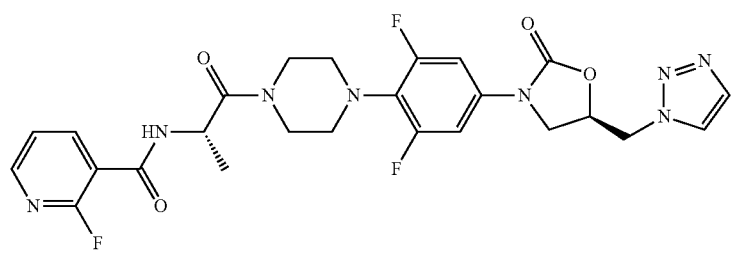
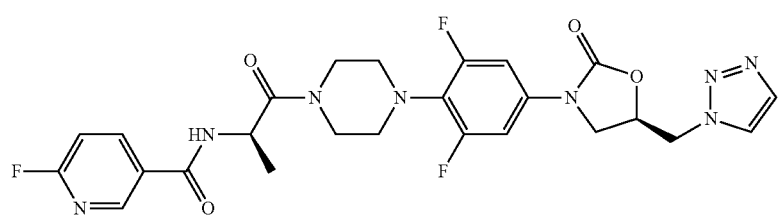
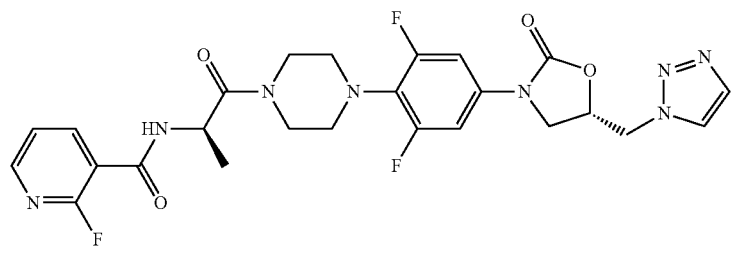
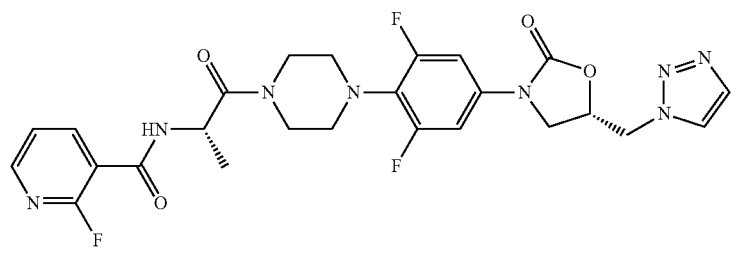
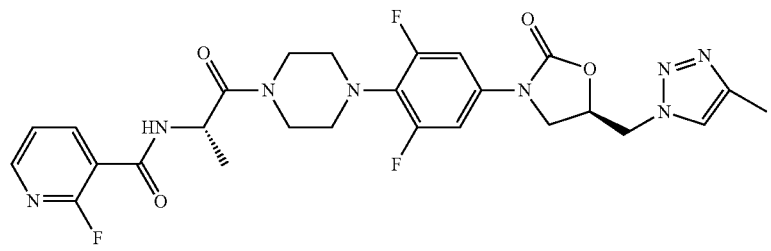

-continued
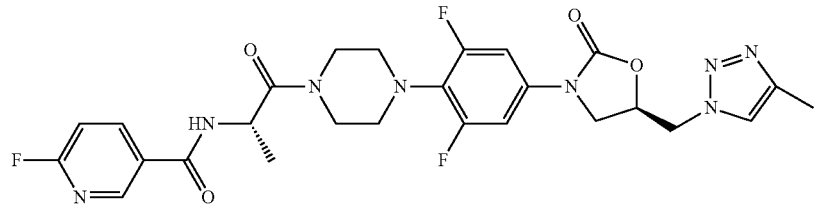
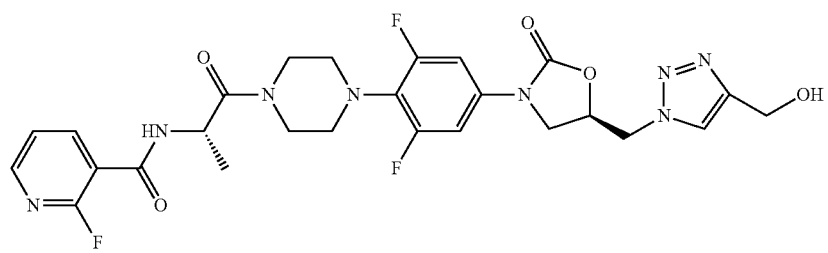
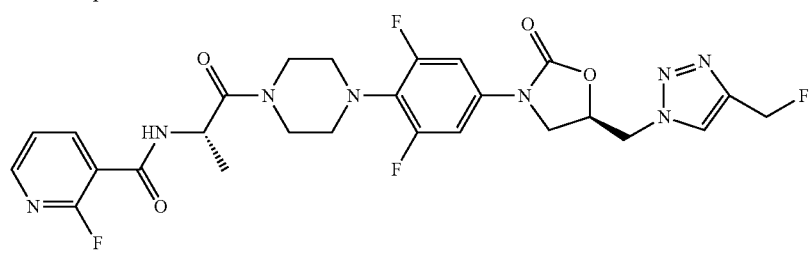
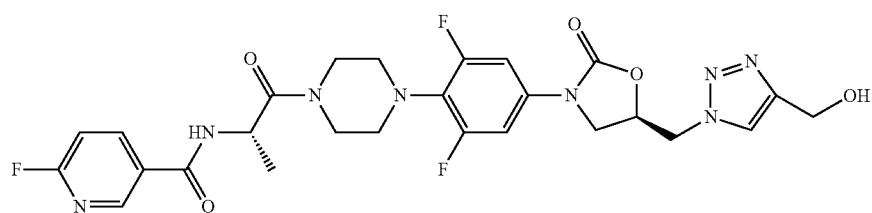
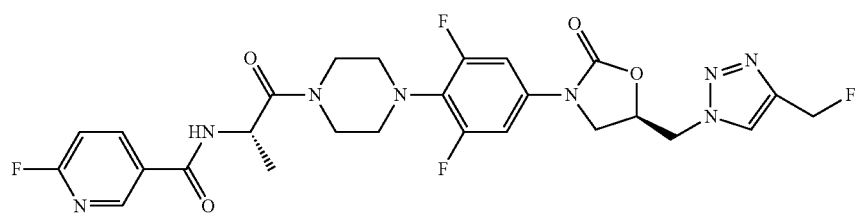
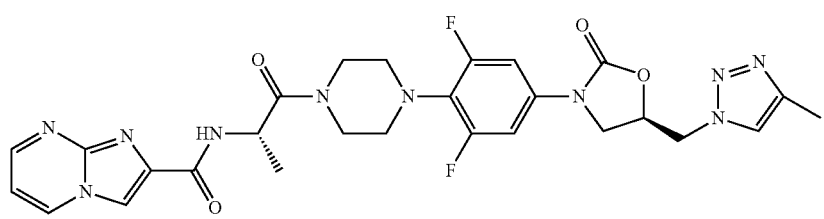
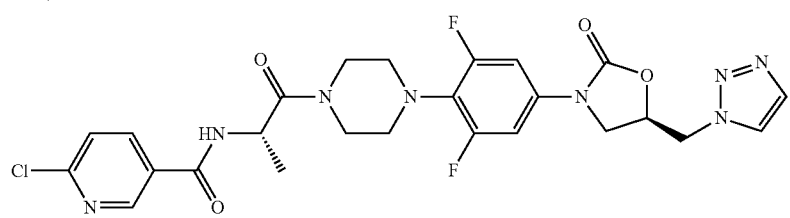

-continued
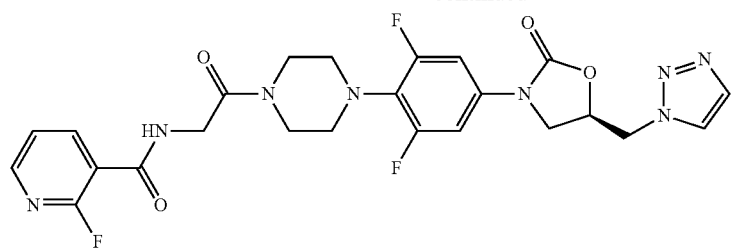
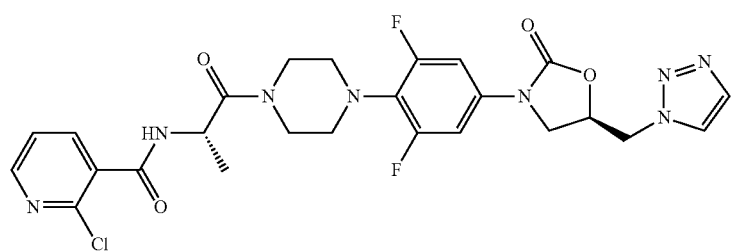
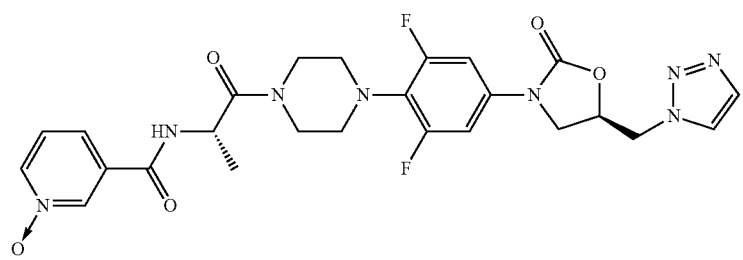
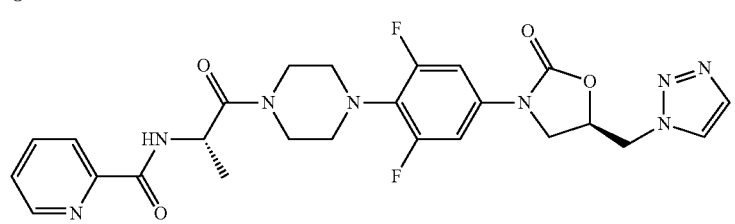
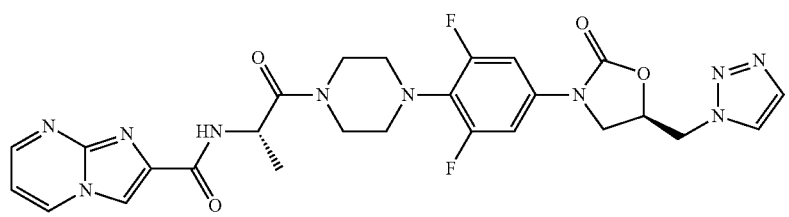
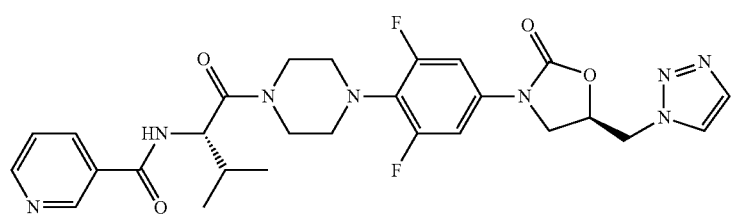
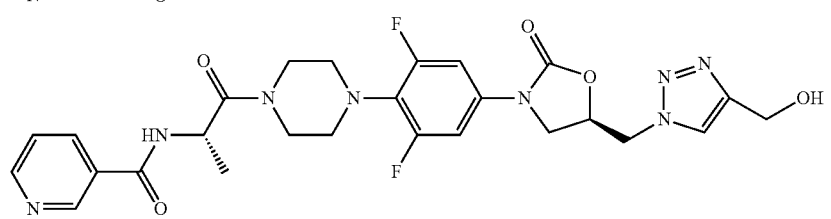

-continued

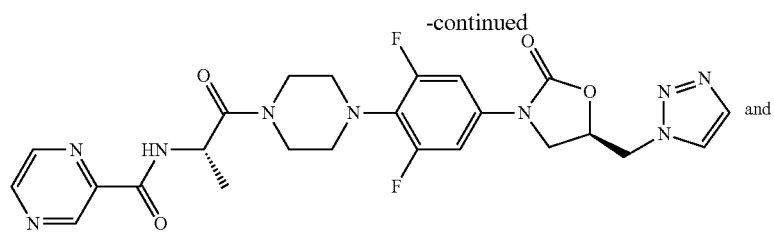

and

12. A pharmaceutical composition comprising a therapeutically effective amount of a compound of Formula I according to claim 1 or its tautomeric forms, stereoisomers, polymorphs, salts or solvates thereof.

13. A method for the amelioration of bacterial infections in a subject in need thereof, that comprises administering a therapeutically effective amount of compound of Formula I according to claim 1.

14. A method according to claim 13, wherein the bacterial infection is caused by multi drug resistant species of *Staphylococcus, Streptococcus, Enterococcus, Bacterioides, Clostridia, H. influenza, Moraxella, Mycobacterium tuberculosis* as well as Linezolid resistant species of *Staphylococcus* and *Enterococcus*.

* * * * *